United States Patent [19]

Takaya et al.

[11] Patent Number: 4,649,146

[45] Date of Patent: Mar. 10, 1987

[54] THIAZOLE DERIVATIVES AND PHARMACEUTICAL COMPOSITION COMPRISING THE SAME

[75] Inventors: Takao Takaya, Kawanishi; Hisashi Takasugi, Osaka, both of Japan

[73] Assignee: Fujisawa Pharmaceutical Co., Ltd., Osaka, Japan

[21] Appl. No.: 574,517

[22] Filed: Jan. 27, 1984

[30] Foreign Application Priority Data

Jan. 31, 1983 [GB] United Kingdom ............... 8302591
Sep. 26, 1983 [GB] United Kingdom ............... 8325684

[51] Int. Cl.$^4$ .................. A61K 31/47; C07D 417/04
[52] U.S. Cl. ..................... 514/307; 514/310;
544/256; 546/118; 546/121; 546/144; 546/146;
546/147; 546/148; 546/192; 546/193; 546/194;
546/209; 546/256; 546/270; 546/271; 546/280;
548/188; 548/191; 548/194; 548/200
[58] Field of Search ............... 548/200; 546/144, 146;
514/307, 310; 544/143

[56] References Cited

U.S. PATENT DOCUMENTS

| 2,866,777 | 12/1958 | Leshin | 546/143 |
| 4,063,925 | 12/1977 | Konotsune et al. | 546/144 |
| 4,499,094 | 2/1985 | Dubroeucq et al. | 546/144 |
| 4,532,250 | 7/1985 | Stout et al. | 546/144 |

*Primary Examiner*—Glennon H. Hollrah
*Assistant Examiner*—James H. Turnipseed
*Attorney, Agent, or Firm*—Oblon, Fisher, Spivak, McClelland & Maier

[57] ABSTRACT

The invention relates to novel pharmaceutical compounds for treatment for ulcer of the formula:

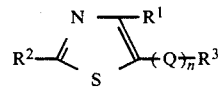

wherein
$R^1$ is lower alkyl, carboxy, hydroxymethyl, halomethyl, lower alkylthiomethyl or hydroxyiminomethyl,
$R^2$ is hydrogen, hydroxy, lower alkyl, pyridyl, amino, lower alkylamino, pyridylamino or guanidino optionally substituted with dimethylaminomethylene,
$R^3$ is dihydroisoquinolyl which may be substituted with halogen, lower alkyl, lower alkoxy, carboxy, hydroxy, pyridyl, amino, lower alkylamino, pyridylamino or guanidino,
Q is —CO—, and
n is an integer of 0 or 1, and
pharmaceutically acceptable salts thereof.

9 Claims, No Drawings

THIAZOLE DERIVATIVES AND PHARMACEUTICAL COMPOSITION COMPRISING THE SAME

This invention relates to new thiazole derivatives. More particularly, this invention relates to new thiazole derivatives and pharmaceutically acceptable salts thereof which have pharmacological activities, processes for preparation thereof, a pharmaceutical composition comprising the same and method of use thereof.

Accordingly, one object of this invention is to provide the new and useful thiazole derivatives and pharmaceutically acceptable salts thereof.

Another object of this invention is to provide processes for preparation of the thiazole derivatives and pharmaceutically acceptable salts thereof.

A further object of this invention is to provide a pharmaceutical composition comprising said thiazole derivative or a pharmaceutically acceptable salt thereof.

Still further object of this invention is to provide a method of using said thiazole derivative or a pharmaceutically acceptable salt thereof for therapeutic treatment of heart disease and ulcer of human being and animals.

Some thiazole derivatives having a cardiotonic activity have been known as described in Japan Kokai No. 134417/1982.

An intensive study undertaken by the inventors of this invention has resulted in the development of novel thiazole derivatives having a superior cardiotonic activity.

The object thiazole derivatives of this invention are novel and represented by the following general formula [I]:

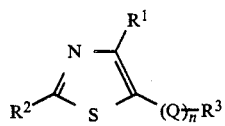

wherein
$R^1$ is lower alkyl, carboxy, a derivative of carboxy, hydroxymethyl, halomethyl, lower alkylthiomethyl, hydroxyiminomethyl or alkenyl which may be substituted with lower alkoxycarbonyl, pyridyl or cyano,
$R^2$ is hydrogen, hydroxy, lower alkyl, pyridyl, amino, lower alkylamino, pyridylamino, arylamino, acylamino, N-(lower)alkyl-N-acylamino, guanidino optionally substituted with dimethylaminomethylene, or ar(lower)alkylamino optionally substituted with lower alkoxy,
$R^3$ is lower alkyl, halo(lower)alkyl or N-containing unsaturated heterocyclic group which may be substituted with halogen, lower alkyl, lower alkoxy, carboxy, a derivative of carboxy, hydroxy, pyridyl, amino, lower alkylamino, pyridylamino, arylamino, acylamino, N-(lower)alkyl-N-acylamino, guanidino, N-oxide or ar(lower)alkylamino optionally substituted with lower alkoxy,
Q is —CO—, and
n is an integer of 0 or 1,
provided that when both of $R^1$ and $R^3$ are lower alkyl then n is an integer of 1 and $R^2$ is lower alkyl, pyridyl, amino, lower alkylamino, pyridylamino, arylamino, acylamino, N-(lower)alkyl-N-acylamino, guanidino optionally substituted with dimethylaminomethylene, or ar(lower)alkylamino optionally substituted with lower alkoxy, and when $R^1$ is lower alkyl and $R^3$ is halo(lower)alkyl then n is an integer of 1.

As to object compound [I], the following points are to be noted. That is, the moieties of "2-aminothiazole" and "2-hydroxythiazole" in the object compound [I] can be alternatively represented by its tautomers i.e. "2-imino-4-thiazoline" and "2-oxo-4-thiazoline", respectively, and both of the said moieties are in the state of tautomeric equilibrium as represented by the following equilibriums.

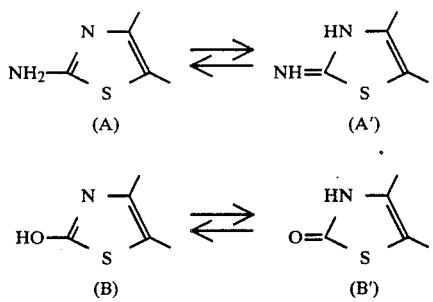

These types of tautomerism have been well known in the arts, and it is obvious to a person skilled in the arts that both of the tautomeric isomers are equilibrated and lie in the reciprocally convertible state, and accordingly it is to be understood that both of such isomers are included within the same category of the object compound [I]. In the present specification, however the object compound [I] including the group of such tautomeric isomers is represented by one of the expressions, i.e. "2-aminothiazole" and the formula:

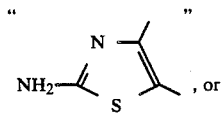, or

"2-hydroxythiazole" and the formula:

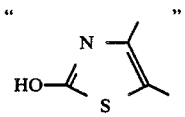

only for the convenient sake.

The object compound [I] of the present invention can be prepared by the following processes.

Process 1

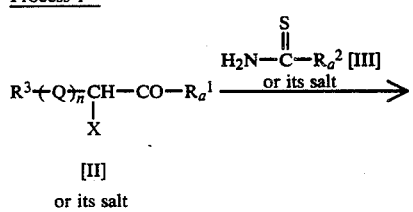

4,649,146
-continued
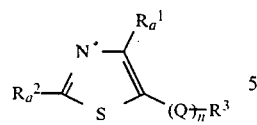
[Ia] or its salt
Process 2
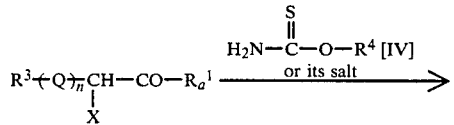
[II] or its salt
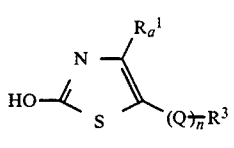
[Ib] or its salt
Process 3
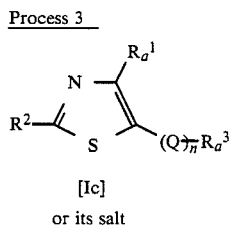
[Ic] or its salt → [Id] or its salt
Process 4
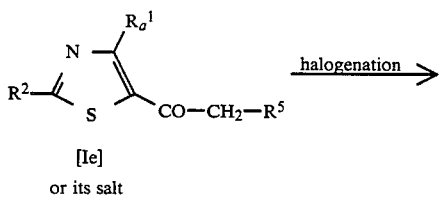
[Ie] or its salt
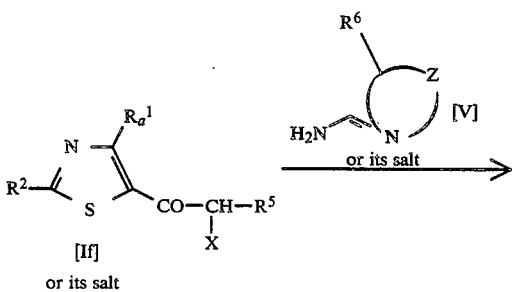
[If] or its salt
Process 5
[If] or its salt
-continued
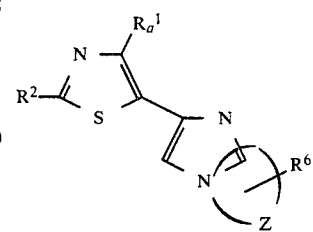
[Ig] or its salt
Process 6
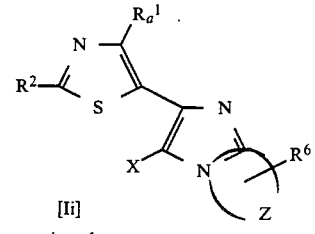
[Ih] or its salt
[Ii] or its salt
Process 7
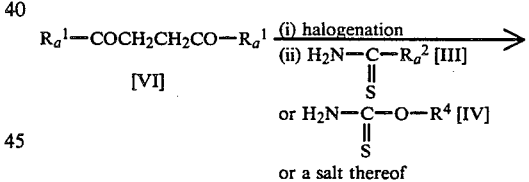
[VI]
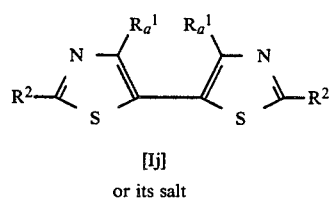
[Ij] or its salt
Process 8
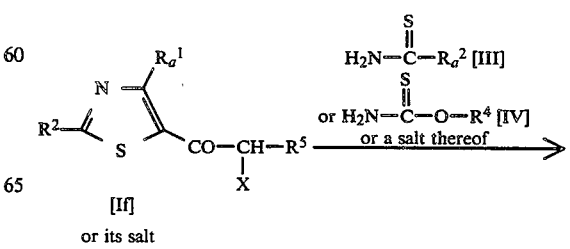
[If] or its salt -continued

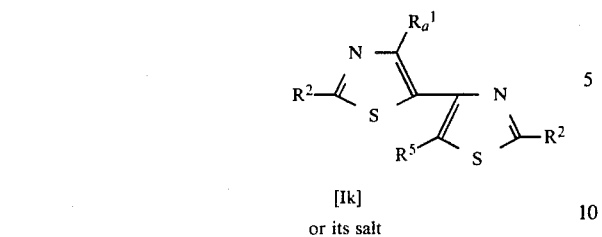

[Ik] or its salt

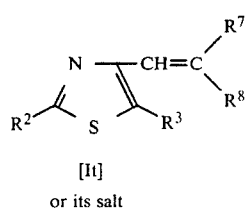

[It] or its salt

Process 9

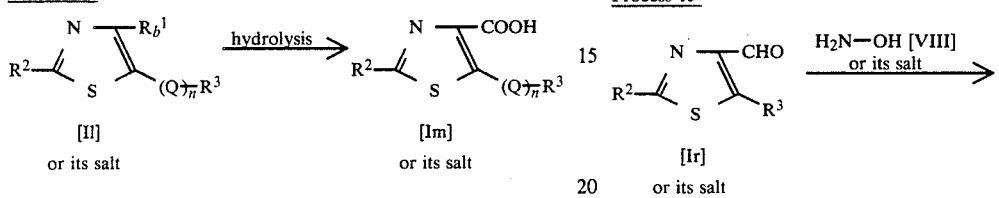

[Il] or its salt

[Im] or its salt

Process 15

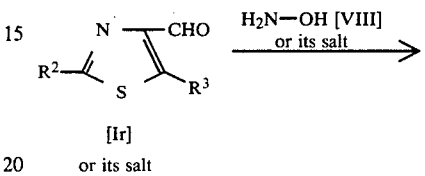

[Ir] or its salt

Process 10

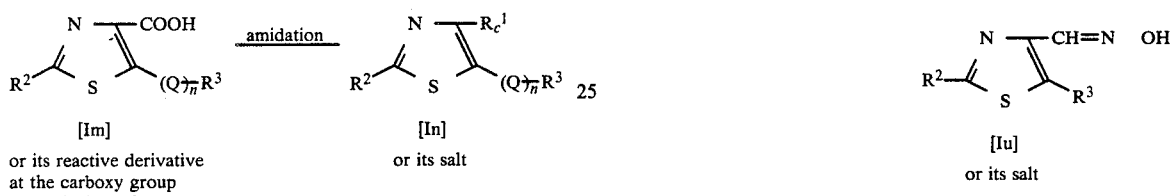

[Im] or its reactive derivative at the carboxy group or a salt thereof

[In] or its salt

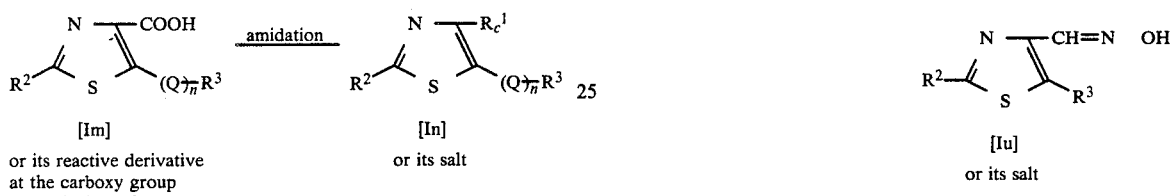

[Iu] or its salt

Process 11

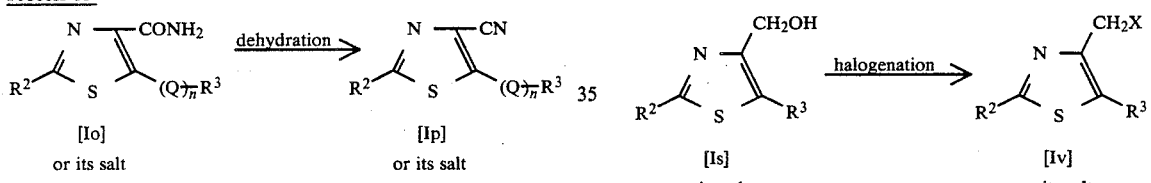

[Io] or its salt

[Ip] or its salt

Process 16

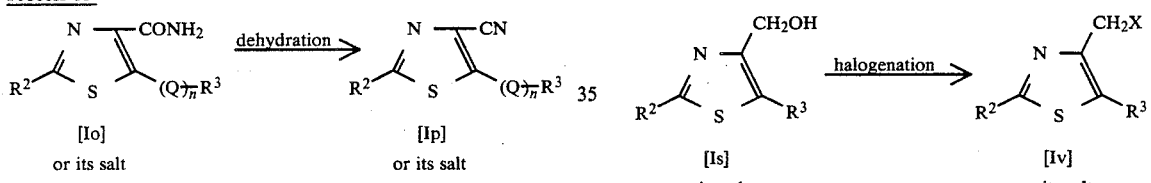

[Is] or its salt

[Iv] or its salt

Process 12

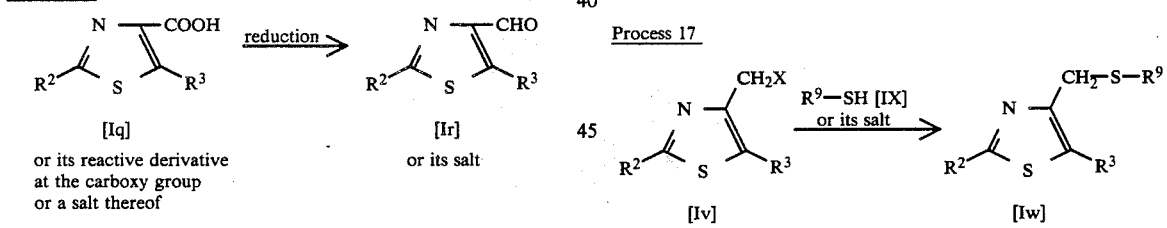

[Iq] or its reactive derivative at the carboxy group or a salt thereof

[Ir] or its salt

Process 17

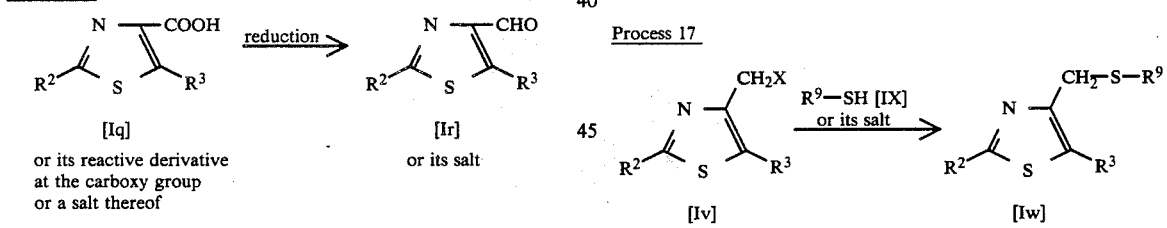

[Iv] or its salt

[Iw] or its salt

Process 13

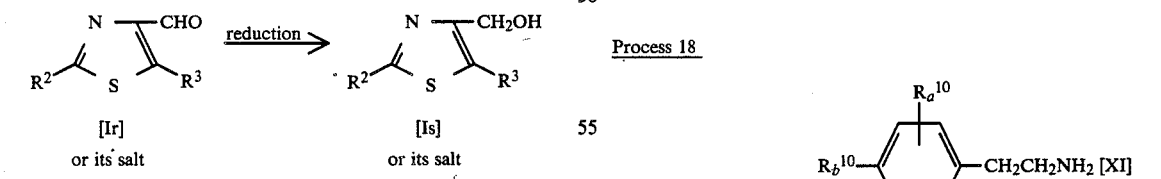

[Ir] or its salt

[Is] or its salt

Process 18

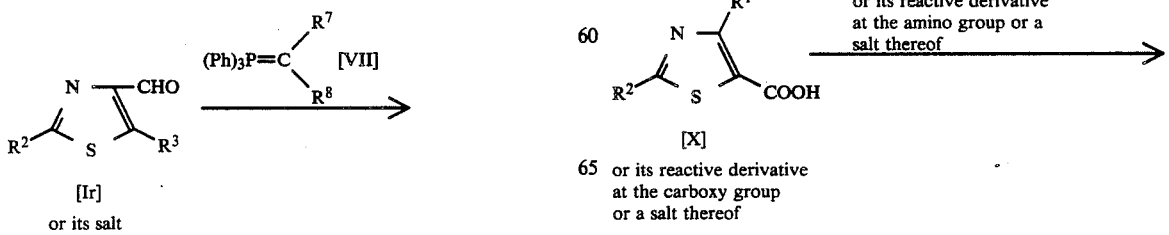

Process 14

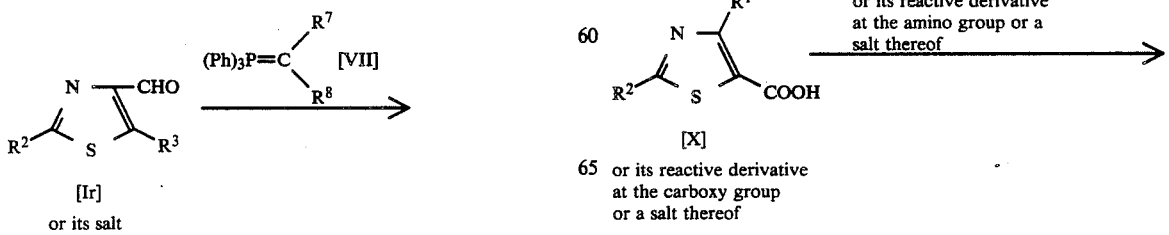

[Ir] or its salt

[X] or its reactive derivative at the carboxy group or a salt thereof

-continued

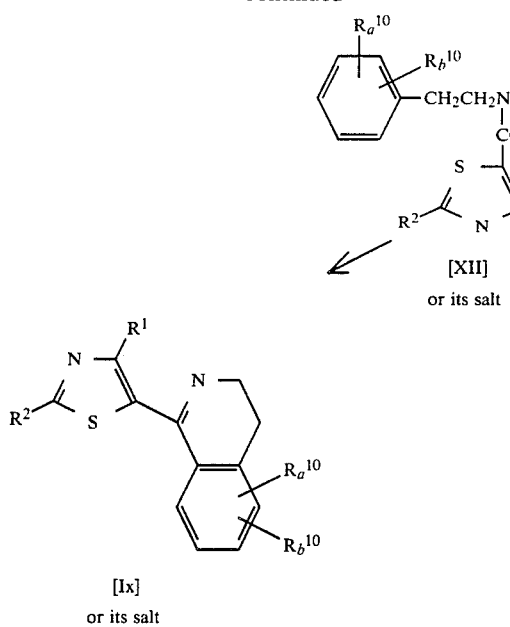

[XII]
or its salt

[Ix]
or its salt

Process 19

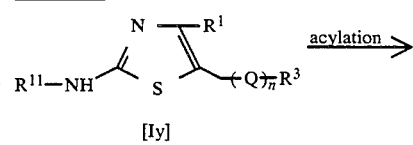

[Iy]
or its reactive derivative
at the amino group
or a salt thereof

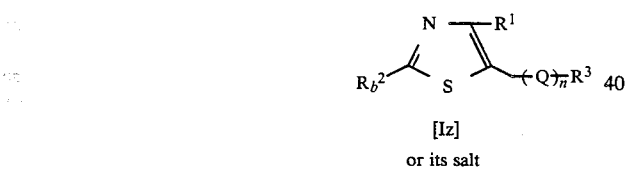

[Iz]
or its salt

Process 20

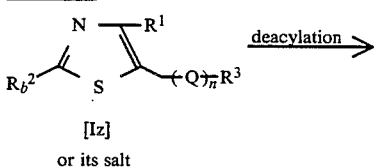

[Iz]
or its salt

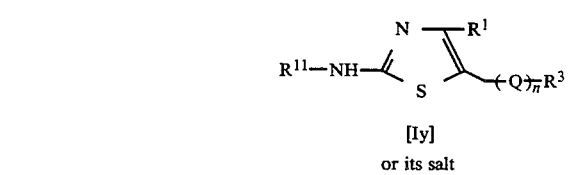

[Iy]
or its salt

Process 21

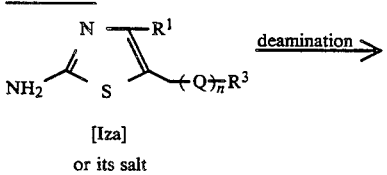

[Iza]
or its salt

-continued

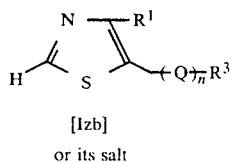

[Izb]
or its salt wherein
R¹, R², R³, Q and n are each as defined above,
$R_a^1$ is lower alkyl or a derivative of carboxy,
$R_b^1$ is protected carboxy,
$R_c^1$ is substituted or unsubstituted carbamoyl,
$R_a^2$ is hydrogen, lower alkyl, pyridyl, amino, lower alkylamino, pyridylamino, arylamino, acylamino, N-(lower)alkyl-N-acylamino, guanidino or ar(-lower)alkylamino oprionally substituted with lower alkoxy,
$R_b^2$ is acylamino or N-(lower)alkyl-N-acylamino,
$R_a^3$ is N-containing unsaturated heterocyclic N-oxide group which may be substituted with halogen, lower alkyl, lower alkoxy, carboxy, a derivative of carboxy, hydroxy, pyridyl amino, lower alkylamino, pyridylamino, arylamino, acylamino, N-(lower)alkyl-N-acylamino, guanidino or ar(lower-)alkylamino optionally substituted with lower alkoxy,
$R_b^3$ is N-containing unsaturated heterocyclic group which may be substituted with halogen, lower alkyl, lower alkoxy, carboxy, a derivative of carboxy, hydroxy, pyridyl, amino, lower alkylamino, pyridylamino, arylamino, acylamino, N-(lower)alkyl-N-acylamino, guanidino or ar(lower)alkylamino optionally substituted with lower alkoxy,
R⁴ is a protective group of hydroxy,
R⁵ is hydrogen or lower alkyl,
R⁶ is hydrogen, amino, lower alkyl or halogen,
R⁷ is hydrogen or lower alkyl,
R⁸ is hydrogen, lower alkyl, lower alkoxycarbonyl, pyridyl or cyano,
R⁹ is lower alkyl,
$R_a^{10}$ and $R_b^{10}$ are each hydrogen or lower alkoxy,
R¹¹ is hydrogen or lower alkyl,
X is halogen, and
Z is taken together with the adjacent C=N group to form an unsaturated heterocyclic ring which may contain additional N and/or S atom(s),
provided that when both of R¹ and R³ are lower alkyl then n is an integer of 1 and R² is lower alkyl, pyridyl, amino, lower alkylamino, pyridylamino, arylamino, acylamino, N-(lower)alkyl-N-acylamino, guanidino optionally substituted with dimethylaminomethylene, or ar(lower)alkylamino optionally substituted with lower alkoxy, and when R¹ is lower alkyl and R³ is halo(lower)alkyl then n is an integer of 1.

In the above and subsequent description of the present specification, suitable examples and illustrations for the various definitions to be included within the scope of the invention are explained in detail as follows:

It is to be noted, however, that the definitions of $R_a^1$, $R_b^1$ and $R_c^1$ are included in the scope of the definition of R¹, that the definitions of $R_a^2$ and $R_b^2$ are included in the scope of the definition of R², and that the definitions of $R_a^3$ and $R_b^3$ are also included in the scope of the definition of R³. Accordingly, the suitable examples and illustrations for $R_a^1$ to $R_c^1$, $R_a^2$ to $R_b^2$ and $R_a^3$ to $R_b^3$ are to be referred to those for R¹, R² and R³, respectively.

The term "lower" is intended to mean 1 to 6 carbon atom(s) unless otherwise indicated.

Suitable examples of lower alkyl for $R^1$, $R^2$, $R^3$, $R^5$, $R^6$, $R^7$, $R^8$, $R^9$ and $R^{11}$ may be a straight or branched one such as methyl, ethyl, propyl, isopropyl, butyl, isobutyl, tert-butyl, pentyl, hexyl or the like.

Suitable examples of lower alkyl moiety of lower alkylthiomethyl for $R^1$, N-(lower)alkyl-N-acylamino for $R^2$, lower alkylamino for $R^2$, and halo(lower)alkyl for $R^3$ are the same as exemplified above.

Accordingly, suitable examples of lower alkylthiomethyl for $R^1$ may be methylthiomethyl, ethylthiomethyl, propylthiomethyl, isopropylthiomethyl, butylthiomethyl, pentylthiomethyl, hexylthiomethyl or the like.

Suitable examples of lower alkylamino for $R^2$ may be methylamino, ethylamino, propylamino, isopropylamino, butylamino, pentylamino, hexylamino or the like.

Suitable derivative of the carboxy group for $R^1$ may include protected carboxy, substituted or unsubstituted carbamoyl, cyano, formyl and the like.

Suitable examples of the protected carboxy may be an esterified carboxy group or the like.

Suitable ester moiety of the abovementioned esterified carboxy group includes lower alkyl esters [e.g. methyl ester, ethyl ester, propyl ester, isopropyl ester, butyl ester, isobutyl ester, tert-butyl ester, pentyl ester, tert-pentyl ester, hexyl ester, etc.], lower cycloalkyl(lower)alkyl esters [e.g. 1-cyclopropylethyl ester, etc.], lower alkenyl esters [e.g. vinyl ester, allyl ester, etc.], lower alkynyl esters [e.g. ethynyl ester, propynyl ester, etc.], lower alkoxyalkyl esters [e.g. methoxymethyl ester, ethoxymethyl ester, isopropoxymethyl ester, 1-methoxyethyl ester, 1-ethoxyethyl ester, etc.], lower alkylthioalkyl esters [e.g. methylthiomethyl ester, ethylthiomethyl ester, ethylthioethyl ester, isopropylthiomethyl ester, etc.], mono- (or di- or tri-) halo(lower)alkyl ester [e.g. 2-iodoethyl ester, 2,2,2-trichloroethyl ester, etc.], lower alkanoyloxy(lower)alkyl ester [e.g. acetoxymethyl ester, propionyloxymethyl ester, butyryloxymethyl ester, valeryloxymethyl ester, pivaloyloxymethyl ester, hexanoyloxymethyl ester, 2-acetoxyethyl ester, 2-propionyloxyethyl ester, etc.], lower alkanesulfonyl(lower)alkyl ester [e.g. mesylmethyl ester, 2-mesylethyl ester, etc.], ar(lower)alkyl esters such as phenyl(lower)alkyl esters which may optionally have 1 to 4 appropriate substituent(s), for example, nitro, hydroxy, lower alkoxy, etc. [e.g. benzyl ester, 4-methoxybenzyl ester, 4-nitrobenzyl ester, phenethyl ester, trityl ester, benzhydryl ester, bis(methoxyphenyl)methyl ester, 3,4-dimethoxybenzyl ester, etc.], aryl esters such as phenyl esters which may optionally have one or more substituent(s) such as halogen, lower alkoxy, etc. [e.g. phenyl ester, tolyl ester, tert-butylphenyl ester, xylyl ester, mesityl ester, cumenyl ester, 4-chlorophenyl ester, 4-methoxyphenyl ester, etc.], tri(lower)alkylsilyl esters [e.g. trimethylsilyl ester, etc.], and lower alkylthio esters [e.g. methylthio ester, ethylthio ester, etc.].

The substituted carbamoyl may include mono (or di)substituted carbamoyl.

Suitable substituent(s) in said substituted carbamoyl may be the aforementioned lower alkyl, ar(lower)alkyl [e.g. benzyl, benzhydryl, trityl, phenethyl, 2-(3,4-dimethoxyphenyl)ethyl, etc.], aryl [e.g. phenyl, tolyl, xylyl, 4-chlorophenyl, naphthyl, etc.], lower cycloalkyl [e.g. cyclopentyl, cyclohexyl, etc.], aryloxy(lower)alkyl [e.g. 3-[3-(pyrrolidin-1-ylmethyl)phenoxy]propyl, etc.] or pyrrolidinyl(lower)alkyl [e.g. (1-ethylpyrrolidin-2-yl)methyl, etc.]. And further, the substituted carbamoyl may be piperazine-carbonyl group optionally substituted with piperonyl group.

Suitable examples of alkenyl for $R^1$ may be vinyl, 1-propenyl, 1-butenyl, 1-pentenyl, 1-hexenyl or the like. These alkenyl groups may be substituted with the aforementioned lower alkyl, lower alkoxycarbonyl [e.g. methoxycarbonyl, ethoxycarbonyl, propoxycarbonyl, hexyloxycarbonyl, etc.], pyridyl or cyano. Suitable examples of the alkenyl group having such substituent(s) may be 2-methoxycarbonylvinyl, 2-pyridylvinyl, 2-cyanovinyl, 2-methyl-1-propenyl or the like.

Suitable examples of arylamino for $R^2$ may be anilino, naphthylamino or the like. The aryl moiety of said arylamino group may be substituted with halogen [e.g. chloro, bromo, etc.], lower alkoxy [e.g. methoxy, ethoxy, propoxy, isopropoxy, butoxy, pentyloxy, hexyloxy, etc.], carboxy or the like.

Suitable examples of ar(lower)alkyl moiety of ar(lower)alkylamino for $R^2$ may be benzyl, benzhydryl, trityl, phenethyl, 3-phenylpropyl or the like. Accordingly, suitable examples of the ar(lower)alkylamino group may be benzylamino, benzhydrylamino, tritylamino, phenethylamino or the like. The aryl moiety of said ar(lower)alkylamino group may be substituted with lower alkoxy [e.g. methoxy, ethoxy, propoxy, butoxy, etc.]. Suitable examples of ar(lower)alkylamino group having such substituent(s) may be 3,4-dimethoxybenzylamino, 4-methoxyphenethyl or the like.

Suitable examples of the acyl moiety of acylamino and N-(lower)alkyl-N-acylamino for $R^2$ may be lower alkanoyl [e.g. formyl, acetyl, propionyl, butyryl, pivaloyl, valeryl, hexanoyl, etc.], aroyl [e.g. benzoyl, naphthoyl, etc.] or the like.

Accordingly, suitable examples of N-(lower)alkyl-N-acylamino for $R^2$ may be N-methylformamido, N-ethylformamido, N-hexylformamido, N-methylacetamido, N-ethylacetamido, N-methylpropionamido, N-methylhexanamido or the like.

Suitable halogen for $R^6$ and X, and the halogen moiety of halomethyl for $R^1$ and halo(lower)alkyl for $R^3$ may be chlorine, bromine, iodine or fluorine.

The halo(lower)alkyl for $R^3$ includes mono(or di or tri)halo(lower)alkyl group. Accordingly, suitable examples of halo(lower)alkyl may be chloromethyl, bromomethyl, iodomethyl, fluoromethyl, 1-chloroethyl, 1-bromoethyl, 2-chloroethyl, 2-bromoethyl, 3-chloropropyl, 4-chlorobutyl, 5-chloropentyl, 6-chlorohexyl, dichloromethyl, dibromomethyl, 1,2-dichloroethyl, 1,2-dibromoethyl, 1-bromo-2-chloroethyl, trichloromethyl, tribromomethyl or the like.

Suitable protective group of hydroxy for $R^4$ may be lower alkyl [e.g. methyl, ethyl, propyl, etc.], substituted or unsubstituted ar(lower)alkyl [e.g. benzyl, p-nitrobenzyl, etc.], substituted or unsubstituted aryl [e.g. phenyl, p-nitrophenyl, etc.], metal salt [e.g. sodium salt, potassium salt, barium salt, lead salt, etc.], quaternary ammonium salt [e.g. ammonium salt, trimethylammonium salt, benzyltrimethylammonium salt, etc.], or the like.

Suitable examples of lower alkoxycarbonyl for $R^8$ may be the same as those exemplified for the substituent of alkenyl group for $R^1$.

Suitable examples of lower alkoxy for $R_a^{10}$ and $R_b^{10}$ may be methoxy, ethoxy, propoxy, isopropoxy, butoxy, pentyloxy, hexyloxy or the like.

The N-containing unsaturated heterocyclic group for $R^3$ may include unsaturated monocyclic or polycyclic groups containing at least one nitrogen atom.

Suitable N-containing unsaturated heterocyclic group may be;

unsaturated 3- to 8-membered (preferably 5- or 6-membered) monocyclic heterocyclic group containing 1 to 4 nitrogen atom(s) [e.g. pyrrolyl, pyrrolinyl, imidazolyl, pyrazolyl, pyridyl, dihydropyridyl, pyrimidinyl, pyrazinyl, pyridazinyl, triazolyl (e.g. 4H-1,2,4-triazolyl, 1H-1,2,3-triazolyl, 2H-1,2,3-triazolyl, etc.), tetrazolyl (e.g. 1H-tetrazolyl, 2H-tetrazolyl, etc.), etc.], unsaturated fused heterocyclic groups containing 1 to 4 nitrogen atom(s) [e.g. indolyl, isoindolyl, indolidinyl, benzimidazolyl, quinolyl, isoquinolyl, 3,4-dihydroisoquinolyl, indazolyl, benzotriazolyl, imidazopyridyl, imidazopyrimidinyl, imidazopyrazinyl, purinyl, pteridinyl, carbazolyl, etc.], unsaturated 3- to 8-membered (preferably 5- or 6-membered) monocyclic heterocyclic groups containing 1 to 2 oxygen atom(s) and 1 to 3 nitrogen atom(s) [e.g. oxazolyl, isoxazolyl, oxadiazolyl (e.g. 1,2,4-oxadiazolyl, 1,3,4-oxadiazolyl, 1,2,5-oxadiazolyl, etc.) etc.], unsaturated fused heterocyclic groups containing 1 to 2 oxygen atom(s) and 1 to 3 nitrogen atom(s) [e.g. benzoxazolyl, benzoxadiazolyl, etc.], unsaturated 3- to 8-membered (preferably 5- or 6-membered) monocyclic heterocyclic groups containing 1 or 2 sulfur atom(s) and 1 to 3 nitrogen atom(s) [e.g. thiazolyl, isothiazolyl, thiadiazolyl (e.g. 1,2,3-thiadiazolyl, 1,2,4-thiadiazolyl, 1,3,4-thiadiazolyl, 1,2,5-thiadiazolyl, etc.), dihydrothiazinyl, etc.], unsaturated fused heterocyclic groups containing 1 to 2 sulfur atom(s) and 1 to 3 nitrogen atom(s) [e.g. benzothiazolyl, benzisothiazolyl, benzothiadiazolyl, imidazothiazolidinyl, etc.], or the like.

The abovementioned heterocyclic groups may have one or more substituent(s) selected from the groups consisting of carboxy, hydroxy, pyridyl, amino, lower alkoxy, pyridylamino, arylamino, guanidino, N-oxide, lower alkyl, a derivative of carboxy, lower alkylamino, acylamino, N-(lower)alkyl-N-acylamino, halogen and ar(lower)alkylamino optionally substituted with lower alkoxy.

Suitable examples of heterocyclic group having such substituent(s) may be monocyclic heterocyclic group [e.g. 2-aminopyridin-5-yl, 2-methylpyridin-5-yl, 2-chloropyridin-4-yl, pyridin-N-oxide-2-yl, pyridin-N-oxide-3-yl, pyridin-N-oxide-4-yl, 3-ethoxycarbonylpyridin-4-yl, 2-aminothiazol-4-yl, 2-anilinothiazol-4-yl, 2-methylthiazol-4-yl, 2-guanidinothiazol-4-yl, 2-hydroxythiazol-4-yl, 2-(4-pyridyl)thiazol-4-yl, 2-amino-4-methylthiazol-5-yl, 2-amino-4-ethoxycarbonylthiazol-5-yl, 2-anilino-4-ethoxycarbonylthiazol-5-yl, 2-methylamino-4-methylthiazol-5-yl, 2-(4-pyridyl)-4-methylthiazol-5-yl, 2-hydroxy-4-methoxycarbonylthiazol-5-yl, 2-hydroxy-4-ethoxycarbonylthiazol-5-yl, etc.], fused heterocyclic group [e.g. 3-chooroimidazo[1,2-a]-pyridin-2-yl, 6-chloroimidazo[1,2-a]pyridin-2-yl, 3-methylimidazo[1,2-a]pyridin-2-yl, 5-methylimidazo[1,2-a]pyridin-2-yl, 7-methylimidazo[1,2-a]pyridin-2-yl, 8-methylimidazo[1,2-a]pyridin-2-yl, 5-aminoimidazo[1,2-a]pyridin-2-yl, 6-chloroimidazo[1,2-a]pyrimidin-2-yl, 6-methylimidazo[1,2-a]pyrimidin-2-yl, imidazo[1,2-a]pyrimidine-8-oxide-2-yl, 3,4-dihydro-6,7-dimethoxyisoquinolin-1-yl, etc.] or the like.

Suitable unsaturated heterocyclic ring which may contain additional N and/or S atom(s) for Z includes the N-containing unsaturated heterocyclic groups as exemplified for $R^3$, and preferably it may be 5- or 6-membered monocyclic heterocyclic ring containing 1 to 4 nitrogen atom(s) such as imidazole, pyrazole, pyridine, pyradine, pyrimidine, pyridazine, thiazolidine or the like.

The abovementioned heterocyclic ring is substituted with amino and optionally substituted with the additional amino, halogen or lower alkyl represented by $R^6$.

Suitable examples of the compound [V] having such substituent(s) may be 2-aminoimidazole, 2-amino-1-methylimidazole, 3-aminopyrazole, 3-amino-1-methylpyrazole, 2-aminopyridine, 2,6-diaminopyridine, 2-amino-5-chloropyridine, 2-amino-6-chloropyridine, 2-amino-4,5-dichloropyridine, 2-amino-3-methylpyridine, 2-amino-4,6-dimethylpyridine, 2-aminopyradine, 2,5-diaminopyradine, 2-amino-5-methylpyradine, 2-amino-5-chloropyradine, 2-aminopyrimidine, 2,4-diaminopyrimidine, 2-amino-4-methylpyrimidine, 2-amino-5-chloropyrimidine, 3-aminopyridazine, 3-amino-6-methylpyridazine, 3-amino-6-chloropyridazine, 2-aminothiazole, 2-amino-3,4-dihydrothiazole or the like.

Suitable pharmaceutically acceptable salts of the object compounds [I] are conventional non-toxic salts and include an organic acid salt [e.g. formate, acetate, trifluoroacetate, maleate, tartrate, methanesulfonate, benzenesulfonate, toluenesulfonate, etc.], an inorganic acid salt [e.g. hydrochloride, hydrobromide, sulfate, phosphate, etc.], a salt with an amino acid [e.g. arginine, glutamic acid, ornithine, etc.], a metal salt such as an alkali metal salt [e.g. sodium salt, potassium salt, etc.] and an alkaline earth metal salt [e.g. calcium salt, magnesium salt, etc.], an ammonium salt, an organic base salt [e.g. trimethylamine salt, triethylamine salt, pyridine salt, picoline salt, dicyclohexylamine salt, N,N'-dibenzylethylenediamine salt, etc.], and the like.

In this respect, it is to be noted that the compounds [Ia] to [Izb] are included within the scope of the compound [I], and accordingly the suitable salts of these compounds [Ia] to [Izb] are to be referred to those as exemplified for the object compounds [I] in the above.

The processes for preparing the object compounds [I] and salts thereof are explained in detail in the following.

Process 1

The object compound [Ia] and its salt can be prepared by reacting the compound [II] or its salt with the compound [III] or its salts.

Suitable salts of the compounds [II] and [III] may be the same as those exemplified for the compound [I].

Suitable examples of the compound [III] may be thiocarbamoyl derivatives such as thiourea, N-(lower)alkylthiourea [e.g. N-methylthiourea, N-ethylthiourea, N-propylthiourea, N-isopropylthiourea, N-hexylthiourea, etc.], N-arylthiourea [e.g. N-phenylthiourea, N-(3,4-dimethoxyphenyl)thiourea, N-tolylthiourea, etc.], N-acylthiourea [e.g. N-formylthiourea, N-acetylthiourea, N-benzoylthiourea, etc.], N-pyridylthiourea [e.g. N-(4-pyridyl)thiourea, N-(3-pyridyl)thiourea, N-(2-pyridyl)-thiourea, etc.], thioformamide, lower alkanecarbthioamide [e.g. thioacetamide, propanecarbthioamide, butanecarbthioamide, pentanecarbthioamide, hexanecarbthioamide, etc.], guanidinocarbthioamide, thionicotinamide, thioisonicotinamide, or the like.

This reaction is usually carried out in a conventional solvent such as water, methanol, ethanol, isopropyl alcohol, tetrahydrofuran, dioxane, chloroform, methylene chloride, dimethylacetamide, dimethylformamide or any other organic solvent which does not adversely influence the reaction. Among these solvents, hydrophilic solvents may be used in a mixture with water.

The reaction temperature is not critical, and the reaction is usually carried out at ambient temperature or under warming or heating.

Process 2

The object compound [Ib] and its salt can be prepared by reacting the compound [II] or its salt with the compound [IV] or its salts.

Suitable salts of the compounds [II] and [IV] may be the same as those exemplified for the compound [I].

Suitable examples of the compound [IV] may be thiocarbamate derivatives such as O-(lower)alkyl thiocarbamate [e.g. O-methyl thiocarbamate, O-ethyl thiocarbamate, O-propyl thiocarbamate, O-isopropyl thiocarbamate, O-hexyl thiocarbamate, etc.], substituted or unsubstituted O-ar(lower)alkyl thiocarbamate [e.g. O-benzyl thiocarbamate, O-p-nitrobenzyl thiocarbamate, etc.], substituted or unsubstituted O-aryl thiocarbamate [e.g. O-phenyl thiocarbamate, O-p-nitrophenyl thiocarbamate, etc.], thiocarbamate salt [e.g. sodium thiocarbamate, barium thiocarbamate, ammonium thiocarbamate, etc.], or the like.

This reaction is carried out substantially in the same manner as Process 1, and therefore the reaction mode and reaction conditions [e.g. solvent, reaction temperature, etc.] of this process are to be referred to those as explained in Process 1.

Process 3

The object compound [Id] and its salt can be prepared by reducing the compound [Ic] or its salt.

The reaction including chemical reduction and catalytic reduction, may be carried out in a conventional manner.

Suitable reducing agents to be used in chemical reduction are a metal [e.g. tin, zinc, iron, etc.], a combination of such metal and/or metallic compound [e.g. chromium chloride, chromium acetate, etc.] and an organic or inorganic acid [e.g. formic acid, acetic acid, propionic acid, trifluoroacetic acid, p-toluenesulfonic acid, hydrochloric acid, hydrobromic acid, etc.], a metal hydride compound such as aluminum hydride compound [e.g. lithium aluminum hydride, sodium aluminum hydride, aluminum hydride, lithium trimethoxyaluminum hydride, lithium tri-t-butoxyaluminum hydride, etc.], borohydride compound [e.g. sodium borohydride, lithium borohydride, sodium cyanoborohydride, tetramethylammonium borohydride, borane, diborane, etc.], a phosphorus compound [e.g. phosphorus trichloride, phosphorus tribromide, triphenylphosphine, triethylphosphine, etc.] and the like.

Suitable catalysts to be used in catalytic reduction are conventional ones such as platinum catalyst [e.g. platinum plate, spongy platinum, platinum black, colloidal platinum, platinum oxide, platinum wire, etc.], palladium catalyst [e.g. spongy palladium, palladium black, palladium oxide, palladium on carbon, colloidal palladium, palladium on barium sulfate, palladium on barium carbonate, etc.], nickel catalyst [e.g. reduced nickel, nickel oxide, Raney nickel, etc.], cobalt catalyst [e.g. reduced cobalt, Raney cobalt, etc.], iron catalyst [e.g. reduced iron, Raney iron, etc.], copper catalyst [e.g. reduced copper, Raney copper, Ullman copper, etc.], or the like.

The reduction is usually carried out in a solvent. A suitable solvent to be used may be water, alcohol [e.g. methanol, ethanol, propanol, etc.] or any other conventional organic solvent such as diethyl ether, dioxane, tetrahydrofuran, etc. or a mixture thereof. Additionally, the aforementioned liquid acids to be used in chemical reduction can also be used as a solvent.

The reaction is preferably carried out under somewhat milder conditions such as under cooling to warming.

In this process, the N-oxide moiety of N-containing heterocyclic group for $R_a{}^3$ is reduced to tertiary amine, and in case that the compound [Ic] has protected carboxy group or formyl for $R_a{}^1$, such groups may be simultaneously reduced to formyl or hydroxymethyl group according to the kind of the reducing agent to be used in this process.

Process 4

The object compound [If] and its salt can be prepared by halogenating the compound [Ie] or its salt.

Suitable halogenating agent of this reaction may include conventional ones as used in halogenation of aliphatic carbonyl group, for example, halogen [e.g. chlorine, bromine, iodine, etc.], sulfuryl halide [e.g. sulfuryl chloride, sulfuryl bromide, etc.], N-halosuccinimide [e.g. N-chlorosuccinimide, N-bromosuccinimide, etc.], pyridinium hydrohalide perhalide [e.g. pyridinium hydrobromide, perbromide, pyridinium hydrochloride perchloride, etc.], quarternary ammonium perhalide [e.g. phenyltrimethylammonium perbromide, etc.], ω-trihaloacetophenone [e.g. ω-tribromoacetophenone, etc.], cupric or potassium bromide, selenium oxychloride, or the like. These halogenating agents may be selected according to the kine of the starting compound [Ie] to be used.

This reaction is usually carried out in a conventional solvent such as chloroform, methylene chloride, carbon tetrachloride, acetic acid, a mixture of hydrogen halide [e.g. hydrogen bromide, hydrogen chloride, etc.] and acetic acid, water, dimethylformamide or the like.

The reaction temperature is not critical, and the reaction is usually carried out at ambient temperature or under warming or heating.

Thus obtained compound [If] and its salt can be optionally converted to the other object compound [Ig] or [Ik] or salt thereof as explained in the following process 5 or Process 8, respectively.

Process 5

The object compound [Ig] and its salts can be prepared by reacting the compound [If] or its salt with the compound [Iv] or its salt.

Suitable salts of the compound [V] may be the same as those exemplified for the compound [I].

This reaction is usually carried out in a conventional solvent such as water, methanol, ethanol, tetrahydrofuran, acetonitrile, 1,2-dimethoxyethane, methylene chloride, chloroform, dimethylacetamide, dimethylformamide, dimethyl sulfoxide or any other organic solvent which does not adversely influence the reaction.

The reaction temperature is not critical, and the reaction is usually carried out at ambient temperature or under warmining or heating.

In this process, in case that the group $R^2$ of the compound [If] is acrylamino or N-(lower)alkyl-N-acylamino and a protic solvent [e.g. methanol, ethanol, etc.] is used as a reaction solvent, the acyl moiety of the group $R^2$ may be simultaneously removed in this reaction.

Process 6

The object compound [Ii] and its salt can be prepared by halogenating the compound [Ih] or its salt.

This reaction may be carried out substantially in the same manner as Process 4, and therefore the reaction mode and reaction conditions [e.g. halogenating agent, solvent, reaction temperature, etc.] of this reaction are to be referred to those as explained in Process 4.

Process 7

The object compound [Ij] and its salt can be prepared by halogenating the compound [VI] (step 1), and then reacting the reaction product with the compound [III] or [IV] or a salt thereof (step 2).

Suitable salts of the compounds [III] and [IV] may be the same as those exemplified for the compound [I].

In this process, the step 1 and the step 2 are carried out in substantially the same manner as those of Process 4, and Process 1 or Process 2, respectively. Therefore, the reaction mode and reaction conditions [e.g. halogenating agent, solvent, reaction temperature, etc.] of this process are to be referred to those Processes.

Process 8

The object compound [Ik] and its salt can be prepared by reacting the compound [If] or its salt with the compound [III] or [IV] or a salt thereof.

Suitable salts of the compounds [III] and [IV] may be the same as those exemplified for the compound [I].

This reaction is carried out in substantially the same manner as those of Process 1 or Process 2, and thereofre the reaction mode and reaction conditions of this process are to be referred to those Processes.

Process 9

The object compound [Im] and its salt can be prepared by hydrolyzing the compound [Il] or its salt This reaction is usually carried out in the presence of an acid or a base.

Suitable acid includes an inorganic acid [e.g. hydrochloric acid, hydrobromic acid, sulfuric acid, etc.], an organic acid [e.g. formic acid, acetic acid, trifluoroacetic acid, propionic acid, benzenesulfonic acid, p-toluenesulfonic acid, etc.], an acidic ion exchange resins and the like.

Suitable base includes an inorganic base such as alkali or alkaline earth metal hydroxide or the corresponding carbonate or bicarbonate [e.g. sodium hydroxide, potassium hydroxide, sodium carbonate, potassium carbonate, lithium carbonate, sodium bicarbonate, calcium hydroxide, magnesium hydroxide, etc.], ammonium hydroxide or the like; an organic base such as an alkoxide or phenoxide of the above metal [e.g. sodium ethoxide, sodium methoxide, lithium phenoxide, etc.], an amine such as mono-, di- or trialkylamine [e.g. methylamine, ethylamine, propylamine, isopropylamine, butylamine, N,N-dimethyl-1,3-propanediamine, trimethylamine, triethylamine, etc.], unsubstituted, mono- or disubstituted arylamine [e.g. aniline, N-methylaniline, N,N-dimethylaniline, etc.], a heterocyclic base [e.g. pyrrolidine, morpholine, N-methylmorpholine, N-methylpiperidine, N,N'-dimethylpiperazine, pyridine, etc.], hydrazines [e.g. hydrazine, methylhydrazine, ethylhydrazine, etc.] or the like; a basic ion-exchange resin and the like.

This reaction is usually carried out in a solvent which does not adversely influence the reaction such as water, hydrophilic solvent such as alcohol [e.g. methanol, ethanol, propanol, etc.], acetone, N,N-dimethylformamide, tetrahydrofuran, dioxane, dimethyl sulfoxide, etc. or a mixture thereof, and other hydrophobic solvent such as benzene, diethyl ether, etc. may also be used as a solvent. In case that the acid or base to be used in this reaction is liquid, it can also be used as a solvent.

The reaction temperature is not critical, and the reaction is usually carried out at ambient temperature or under warming or heating.

Process 10

The object compound [In] and its salt can be prepared by subjecting the compound [Im] or its reactive derivative at the carboxy group or a salt thereof to amidation reaction.

This reaction is usually carried out in a conventional manner for instance, by heating the ammonium or amine salt of the compound [Im], by reacting the compound [Im] or its reactive derivative at the carboxy group or a salt thereof with ammonia or amine or its reactive derivative at the amino group or a salt thereof, or the like.

Suitable examples of the amine to be used in this reaction may include primary or secondary amine optionally having suitable substituent(s). The substituent of said amine may be the same ones as exemplified for the substituted carbamoyl for $R^1$.

Suitable reactive derivatives at the amino group of the amine include conventional ones used in amidation, for example, Schiff's base type imino or its tautomeric enamine type isomer formed by reaction of the imine with a carbonyl compound, a silyl derivative formed by reaction of the amine with a silyl compound such as trimethylsilylacetamide, bis(trimethylsilyl)acetamide or the like, a derivative formed by reaction of the amine with phosphorus trichloride or phosgene, and the like.

Suitable salts of the amine may be the same as those exemplified for the compound [I].

Suitable reactive derivatives at the carboxy group of the compound [Im] may include an acid halide, an acid anhydride, an ester, an activated amide, an activated ester and the like.

Suitable examples of such reactive derivatives may be an ester such as lower alkyl ester [e.g. methyl ester, ethyl ester, propyl ester hexyl ester, etc.], acid chloride, an acid azide, a mixed acid anhydride with an acid such as substituted phosphoric acid [e.g. dialkylphosphoric acid, phenylphosphoric acid, etc.], aliphatic carboxylic acid [e.g. pivalic acid, acetic acid, trichloroacetic acid, etc.] or the like, a symmetrical acid anhydride, an activated amide with imidazole, triazole or dimethylpyrazole, an activated ester with N-hydroxysuccinimide, N-hydroxyphthalimide or 1-hydroxy-6-chlorobenzotriazole, and the like.

The reactive derivatives of the compound [Im] and amine can be selected according to the kinds of the compound [Im] and amine, respectively.

When the compound [Im] is used in a free acid form or its salt form in the reaction, the reaction is preferably carried out in the presence of a conventional condensing agent such as N,N'-dicyclohexylcarbodiimide, N-cyclohexyl-N'-morpholinoethylcarbodiimide, N-ethyl-N'-(3-dimethylaminopropyl)carbodiimide, thionyl chloride, oxalyl chloride, lower alkoxycarbonyl halide [e.g. ethyl chloroformate, isobutyl chloroformate, etc.], 1-(p-chlorobenzenesulfonyloxy)-6-chloro-1H-benzotriazole, or the like.

The reaction is usually carried out in a conventional solvent such as water, acetone, dioxane, chloroform, methylene chloride, ethylene chloride, tetrahydrofuran, ethyl acetate, N,N-dimethylformamide, pyridine or any other organic solvent which does not adversely influence the reaction. Among these solvents, hydrophilic solvents may be used in a mixture with water.

The reaction may be preferably carried out in the presence of an inorganic or an organic base such as an alkali metal hydroxide [e.g. sodium hydroxide, potassium hydroxide, etc.], an alkali metal carbonate [e.g. sodium carbonate, potassium carbonate, etc.], an alkali metal bicarbonate [e.g. sodium bicarbonate, potassium bicarbonate, etc.], tri(lower)alkylamine [e.g. trimethylamine, triethylamine, etc.], pyridine or its derivative [e.g. picoline, lutidine, 4-dimethylaminopyridine, etc.], or the like. In case that the base or the condensing agent to be used as liquid, it can also be used as a solvent.

The reaction temperature is not critical, and the reaction is usually carried out under cooling, at ambient temperature or under warming or heating.

Process 11

The object compound [Ip] and its salt can be prepared by dehydrating a compound [Io] or its salt.

Suitable examples of the dehydrating agent may be an acid anhydride [e.g. acetic anhydride, trifluoroacetic anhydride, benzoic anhydride, etc.], phosphorus compound [e.g. phosphorus pentoxide, phosphorus pentachloride, phosphorus oxychloride, etc.], thionyl chloride, toluenesulfonyl chloride, dicyclohexylcarbodiimide, or the like.

This reaction is preferably conducted in the presence of a base. Suitable examples of the base may be pyridine, triethylamine, N-methylmorpholine, N,N-dimethylaniline or the like.

This reaction is usually carried out in a solvent such as methylene chloride, chloroform, carbon tetrachloride, benzene, dimethylformamide or any other organic solvent which does not adversely influence the reaction. In case that the dehydrating agent or base is liquid, it can also be used as a solvent.

The reaction temperature is not critical, and the reaction can be usually carried out under cooling, at ambient temperature or under warming or heating.

Process 12

The object compound [Ir] and its salt can be prepared by reducing the compound [Ig] or its reactive derivative at the carboxy group or a salt thereof.

Suitable reactive derivatives at the carboxy group of the compound [Ig] may be the aforementioned esterified carboxy and acid halide, or the like.

This reaction may be carried out substantially in the same manner as Process 3, and therefore the reaction mode and reaction conditions [e.g. reducing agent, solvent, reaction temperature, etc.] of this reaction are to be referred to those as explained in Process 3.

Process 13

The object compound [Is] and its salt can be prepared by reducing the compound [Ir] or its salt.

This reaction may be carried out substantially in the same manner as Process 3, and thereofore the reaction mode and reaction conditions [e.g. reducing agent, solvent, reaction temperature, etc.] of this reaction are to be referred to those as explained in Process 3.

Process 14

The object compound [It] and its salt can be prepared by reacting a compound [Ir] or its salt with a compound [VII].

This reaction is what is called "Wittig reaction".

This reaction is usually carried out in a conventional solvent such as benzene, toluene, hexane, heptane, methylene chloride, tetrahydrofuran, water or a mixture thereof.

The reaction temperature is not critical, and the reaction is usually carried out under cooling, at ambient temperature or under warming.

The starting compound [VII] to be used in this process can be prepared by a conventional manner, for example, by reacting a compound of the formula:

wherein $R^7$ and $R^8$ are each as defined above, and Y is halogen, with a strong base such as organometal compound [e.g. butyl lithium, phenyllithium, etc.], alkali metal hydride [e.g. sodium hydride, potassium hydride, etc.], alkali metal amide [e.g. sodium amide, potassium diisopropylamide, etc.], alkali metal alkoxide [e.g. sodium methoxide, potassium tert-butoxide, etc.] or the like. Thus obtained compound [VII] can be isolated from a reaction mixture by a conventional manner, but it can be used in this process without isolation.

Process 15

The object compound [Iu] and its salt can be prepared by reacting the compound [Ir] or its salt with the compound [VIII] or its salt.

Suitable salts of the compound [VIII] may be the same as those exemplified for the compound [I].

This reaction is usually carried out in a conventional solvent such as methanol, ethanol, propanol, tetrahydrofuran, dioxane, dimethylformamide or any other organic solvent which does not adversely influence the reaction.

In case that a salt of the compound [VIII] is used in this reaction, the reaction is preferably carried out in the presence of a conventional base.

The reaction temperature is not critical, and the reaction is usually carried out at ambient temperature or under warming or heating.

Process 16

The object compound [Iv] and its salt can be prepared by halogenating a compound [Is] or its salt.

Suitable halogenating agents may include conventional ones as used in the replacement of hydroxy group by halogen, for example, thionyl halide [e.g. thionyl chloride, thionyl bromide, etc.], hydrogen halide [e.g. hydrogen chloride, hydrogen bromide, etc.], phosphorus halide [e.g. phosphorus tribromide, phosphorus trichloride, phosphorus pentachloride, etc.] or the like.

This reaction can be carried out in the presence or absence of a solvent. Suitable solvent to be used in this reaction may be chloroform, methylene chloride, carbon tetrachloride, benzene, toluene or any other organic solvent which does not adversely influence the reaction.

In case that the above-mentioned halogenating agent is liquid, it can also be used as a solvent.

The reaction temperature is not critical, and the reaction is usually carried out at ambient temperature or under warming or heating.

Process 17

The object compound [Iw] and its salt can be prepared by reacting a compound [Iv] or its salt with a compound [IX] or its salt.

Suitable salts of the compound [IX] may be the same as those exemplified as base salts of the object compound [I].

This reaction is usually carried out in a solvent such as methanol, ethanol, propanol, tetrahydrofuran, dioxane, dimethylformamide or any other organic solvent which does not adversely influence the reaction.

In case that a free form of the compound [IX] is used in this reaction, the reaction is preferably carried out in the presence of a conventional base.

The reaction temperature is not critical, and the reaction is usually carried out at ambient temperature or warming or heating.

Process 18

(i) Preparation of the intermediate compound [XII]

The intermediate compound [XII] and its salt can be prepared by reacting a compound [X] or its reactive derivative at the carboxy group or a salt thereof with a compound [XI] or its reactive derivative at the amino group or a salt thereof.

This reaction may be carried out substantially in the same manner as Process 10, and therefore the reaction mode and reaction conditions [e.g. reactive derivatives, solvent, reaction temperature, etc.] of this reaction are to be referred to those as explained in Process 10.

(ii) Preparation of the object compound [Ix]

The object compound [Ix] and its salt can be prepared by cyclodehydrating a compound [XII] or its salt. This reaction is what is so-called [Bischler-Napieralski reaction".

Suitable cyclodehydrating agents may be a conventional dehydrating agents such as phosphorus compound [e.g. phosphorus oxychloride, phosphorus pentoxide, phosphorus pentachloride, polyphosphoric acid, polyphosphate ester, etc.], anhydrous zinc chloride or the like.

This reaction is usually carried out in a solvent such as chloroform, benzene, toluene, xylene, nitrobenzene, tetralin or any other organic solvent which does not adversely influence the reaction. The selection of the solvent is dependent upon a reaction temperature.

The reaction temperature is not critical, and the reaction is usually carried out under heating or refluxing.

Process 19

The object compound [Iz] and its salt can be prepared by acylating a compound [Iy] or its reactive derivative at the amino group or a salt thereof.

This reaction may be carried out substantially in the same manner as Process 10, and therefore the reaction mode and reaction conditions [e.g. reactive derivatives, solvent, reaction temperature, etc.] of this reaction are to be referred to those as explained in Process 10.

Process 20

The object compound [Iy] and its salt can be prepared by deacylating a compound [Iz] or its salt.

Suitable method for this deacylation reaction may include conventional one such as hydrolysis and the like.

Hydrolysis is preferably carried out in the presence of an acid.

Suitable acid may be an inorganic acid [e.g. hydrochloric acid, hydrobromic acid, sulfuric acid, etc.], an organic acid [e.g. formic acid, acetic acid, trifluoroacetic acid, propionic acid, benzenesulfonic acid, p-toluenesulfonic acid, etc.], an acidic ion-exchange resin and the like. In case that the organic acid such as trifluoroacetic acid and p-toluenesulfonic acid is used in this reaction, the reaction is preferably carried out in the presence of cation trapping agents [e.g. anisole, etc.].

The acid suitable for this hydrolysis can be selected according to the kinds of the acyl group to be removed.

The hydrolysis is usually carried out in a conventional solvent which does not adversely influence the reaction such as water, methanol, ethanol, propanol, tert-butyl alcohol, tetrahydrofuran, N,N-dimethylformamide, dioxane or a mixture thereof, and further the above-mentioned acids can also be used as a solvent when they are in liquid.

The reaction temperature of this hydrolysis is not critical, and the reaction is usually carried out under cooling, at ambient temperature or under heating.

Process 21

The object compound [Izb] and its salts can be prepared by subjecting the compound [Iza] or its salt to a deamination reaction.

The deamination reaction is carried out in accordance with a conventional method such as reduction of diazonium salts of the compound [Iza] by a reducing agent (Method A), reaction of the compound [Iza] with a nitrous acid ester under heating (Method B), or the like.

Method A

Diazonium salt of the compound [Iza] can be prepared by reacting the compound [Iza] with nitrous acid or $NO^+$-donor such as a mixture of an alkali metal nitrite [e.g. sodium nitrite, potassium nitrite, etc.] and an acid [e.g. hydrochloric acid, sulfuric acid, etc.], nitrous acid ester [e.g. ethyl nitrite, amyl nitrite, isoamyl nitrite, etc.], nitrosyl compound [e.g. nitrosylsulfuric acid, etc.], or the like.

This reaction is usually carried out in a conventional solvent such as water, acetic acid, propionic acid, tetrahydrofuran, ethanol, dioxane, dimethylformamide, or the like. The reaction temperature is not critical, and the reaction can be carried out at any temperature from cooling to heating. The reaction temperature and solvent may be selected according to the kind of the agent to be used. Thus obtained diazonium salt is successively reduced in the next step without isolation.

The reduction of diazonium salt of the compound [Iza] is usually carried out in the same solvent at that of the abovementioned step.

Suitable reducing agents for this reaction may be hydrophosphorus acid, sodium borohydride, formaldehyde, hydrazine, ethanol, zinc metal, or the like.

The reaction temperature is not critical, and the reaction is preferably carried out under cooling or at ambient temperature.

Method B

The deamination of the compound [Iza] by Method B is usually carried out in a conventional solvent such as tetrahydrofuran, acetic acid, propionic acid, dioxane, ethanol, dimethylformamide, or the like.

Suitable nitrous acid ester may be isoamyl nitrite, amyl nitrite or the like.

The reaction temperature is not critical, and the reaction is preferably carried out under heating.

The starting compounds [II] include known compounds described in Journal of the American Chemical Society, Vol. 67, 395 (1945), etc., and new compounds.

The new compounds [II] can be prepared by following method.

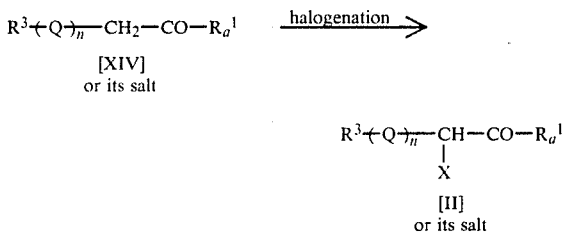

wherein $R_a^1$, $R^3$, X, Q and n are each as defined before.

The compound [II] and its salt can be prepared by halogenating the compound [XIV] or its salt.

Suitable salts of the compounds [II] and [XIV] may be the same as those exemplified for the compound [I].

This reaction is carried out in substantially the same manner as that of Process 4.

It is to be noted that each of the object compound [I] and the starting compound [II] include one or more stereoisomers due to asymmetric carbon atom or double bond in the molecule, and all of such isomers of the compound [I] and [II] are included within the scope of this invention.

The new thiazole derivatives [I] and pharmaceutically acceptable salts thereof possess a cardiotonic activity and antiulcer activity and are useful for a therapeutic treatment of heart disease [e.g. cardiac insufficiency, etc.] and ulcer.

For the purpose of showing pharmaceutical activity of the thiazole derivatives [I], pharmacological test date are illustrated in the following.

[A] CARDIOTONIC ACTIVITY (1) Effect on Spontaneous Contraction of Isolated Guinea Pig Atria Test method:

An atrial strip was removed from male Hartley strain guinea pigs weighing 500–560 g, and suspended in an organ bath containing Tyrode's solution. The bath fluid was maintained at 30° C. and aerated with a gas mixture of 95% $O_2$ and 5% $CO_2$. The atrium was connected to a strain gauge under an initial tension of 0.4–0.6 g and spontaneous atrial contraction was recorded isometrically.

Test compound was dissolved in distilled water and added to the organ bath, and contractile force and heart rate after after dosing were compared with those during the predosing period. Experiments were conducted with 3 separate preparations for each concentration.

Test results were represented in terms of percentage of contractile force changes (C.F.C.) calculated by following formula.

$$C.F.C. (\%) = \left( \frac{\text{contractile force after dosing}}{\text{contractile force before dosing}} - 1 \right) \times 100$$

| Test Compound (Example No.) | Test results: Concentration (g/ml) | C.F.C. (%) |
|---|---|---|
| Example 2 | $10^{-6}$ | 2.6 |
|  | $10^{-5}$ | 29.2 |
|  | $10^{-4}$ | 139.5 |
| Example 3-(2) | $10^{-6}$ | 3.7 |
|  | $10^{-5}$ | 24.0 |

| Test Compound (Example No.) | Test results: Concentration (g/ml) | C.F.C. (%) |
|---|---|---|
| Example 3-(3) | $10^{-5}$ | 24.0 |
| Example 4 | $10^{-6}$ | 27.0 |
|  | $10^{-5}$ | 53.3 |
| Example 5-(2) | $10^{-5}$ | 15.0 |
| Example 6 | $10^{-5}$ | 26.4 |
| Example 9 | $10^{-5}$ | 39.3 |
| Example 34 | $10^{-6}$ | 18.8 |
|  | $10^{-5}$ | 34.3 |
| Example 35 | $10^{-6}$ | 20.7 |
|  | $10^{-5}$ | 42.9 |
| Example 38 | $10^{-5}$ | 21.6 |
| Example 39 | $10^{-5}$ | 51.7 |
| Example 42 | $10^{-5}$ | 30.8 |
| Example 53 | $10^{-6}$ | 3.5 |
|  | $10^{-5}$ | 22.2 |
| Example 54 | $10^{-5}$ | 23.1 |
| Example 64 | $10^{-5}$ | 30.2 |
| Example 77-(1) | $10^{-6}$ | 1.6 |
|  | $10^{-5}$ | 20.9 |
| Example 80 | $10^{-5}$ | 16.7 |
|  | $10^{-4}$ | 35.3 |
| Example 81 | $10^{-6}$ | 4.0 |
|  | $10^{-5}$ | 17.7 |
| Example 84 | $10^{-6}$ | 4.0 |
|  | $10^{-5}$ | 20.3 |
|  | $10^{-4}$ | 17.1 |
| Example 91 | $10^{-5}$ | 31.8 |
| Example 95 | $10^{-6}$ | 29.7 |
|  | $10^{-5}$ | 49.7 |
| Example 100 | $10^{-6}$ | 24.0 |
|  | $10^{-5}$ | 52.6 |
| Example 102 | $10^{-5}$ | 31.9 |
| Example 122 | $10^{-5}$ | 36.8 |
| Amrinone* | $10^{-6}$ | 4.8 |
|  | $10^{-5}$ | 16.5 |
|  | $10^{-4}$ | 15.4 |

*Known compound actually used as cardiotonic medicine.

(2) Effect on Blood Pressure in Anesthetized Dogs

Test Method:

Mongrel dogs of either sex were anesthetized with sodium pentobarbital, 35 mg/kg, i.p. The animals were allowed to breathe spontaneously. The left carotid artery was isolated and a catheter (USCI, #8F) filled with heparinized saline was inserted and advanced into the left ventricle. The catheter was connected to a pressure transducer (Nihonkohden, MPU-0.5A) to measure the left ventricular pressure from which dp/dt max was derived by analog computing. To measure the systemic blood pressure the left femoral artery was cannulated. The blood pressure pulse was used to trigger a heart rate meter. Another catheter was positioned in the vena cava through right femoral vein for injection of drugs. Systemic blood pressure, left ventricular pressure, dp/dt max and heart rate were recorded simultaneously on a polygram (Nihonkohden, RJG-4008).

Test compound was dissolved in distilled water (0.2 ml/kg) or dimethyl sulfoxide (0.04 ml/kg) and injected into the femoral vein. The parameters after dosing were compared with those during the predosing period.

Test results were represented in terms of percentage of dp/dt max changes (dp/dt M.C) calculated by following formula.

$$dp/dt\ M.C\ (\%) = \left( \frac{dp/dt \text{ max after dosing}}{dp/dt \text{ max before dosing}} - 1 \right) \times 100$$

| Test Compound (Example No.) | Test results: Dose (mg/kg) | dp/dt M.C (%) |
|---|---|---|
| Example 3-(1) | 1.0 | 82.0 |
| Example 3-(3) | 0.1 | 39.0 |
|  | 1.0 | 204.0 |
| Example 6 | 0.1 | 65.0 |
|  | 1.0 | 80.0 |
| Example 10 | 0.1 | 13.0 |
|  | 1.0 | 128.0 |
| Example 35 | 1.0 | 119.0 |
| Example 121 | 0.1 | 69.0 |
|  | 1.0 | 96.0 |
| Amrinone | 0.1 | 9.0 |
|  | 1.0 | 80.0 |

[B] ANTIULCER ACTIVITY

(1) Gastric Secretion in Heidenhain Pouch Dogs

Beagle dogs, weighing about 8–13 kg, were used for the study on gastric secretion. The animals were surgically provided with a vagally denervated Heidenhain pouch. One month or more later, the dogs were fasted overnight Gastric secretion was stimulated by an intravenous infusion of tetragastrin (10 μg/kg/hr). Gastric samples were collected at 15 min intervals. After its volume was almost constant, test compound suspended in 0.1% methylcellulose solution was injected intravenously (0.2 ml/kg). Acid concentration was determined by tritrating an aliquot to pH 7.0 with 0.1N sodium hydroxide solution using automatic titration (Hiranuma RAT-11 Type). Total acid output was calculated by multiplying total volume of gastric samples by acid concentration, and percentage change of total acid output was calculated by comparing with predosing value of test compound.

| Test Compound (Example No.) | Test results: Dose (mg/kg) | Inhibition (%) |
|---|---|---|
| Example 38 | 1 | 95.1 |
| Example 56 | 1 | 47.5 |

(2) Inhibition of Stress Ulcer

Five male Sprague-Dawley rats, aged 7 weeks and weighing about 200 g were used per group for the study on stress ulcer after the fast for 24 hours. Each animal was immobilized in a restrain cage and immersed to a level of the xiphoid in a water bath kept 22° C. The test compound suspended in 0.1% methylcellulose solution was administered orally (5 ml/kg) just before the immobilization. Seven hours later, the animals were sacrificed and their stomachs were removed. The stomach was then fixed with 2% formalin. The area of ulcers was measured for each animal. The mean area (mm$^2$) in the test animals was compared with that in the control animals.

| Test Compound (Example No.) | Test results: Dose (mg/kg) | Inhibition (%) |
|---|---|---|
| Example 2 | 32 | 82.7 |
| Example 3-(1) | 32 | 93.6 |
| Example 8 | 32 | 87.5 |
| Example 12 | 32 | 89.1 |
| Example 16 | 32 | 89.2 |
|  | 10 | 18.5 |
| Example 17 | 32 | 88.4 |
| Example 18 | 32 | 97.7 |
|  | 10 | 44.5 |
| Example 37 | 32 | 85.5 |
| Example 39 | 32 | 82.7 |
| Example 84 | 32 | 85.4 |
| Example 89 | 32 | 84.6 |
| Example 113 | 32 | 88.9 |
| Example 117 | 32 | 81.9 |

(3) Inhibition on Ethanol Ulcer

Five male Sprague-Dawley rats, aged 7 weeks and weighing about 200 g, were used per group for the study on ethanol ulcer after the fast for 24 hours.

Test compound was suspended in 0.1% methylcellulose aqueous solution, and the suspension (5 ml/kg) was orally given to each rat.

The control group was given a vehicle, i.e. 0.1% methylcellulose aqueous solution (5 ml/kg), alone in the same way.

Absolute ethanol (5 ml/kg) was orally administered 30 minutes after dosing with test compound, and one hour later, the rats were sacrificed and their stomachs were removed. The area of ulcers of each rat was measured. The mean area (mm$^2$) in the medicated group was compared with that in the control group.

| Test Compound (Example No.) | Test results: Dose (mg/kg) | Inhibition (%) |
|---|---|---|
| Example 2 | 32 | 98.2 |
|  | 10 | 93.4 |
|  | 3.2 | 82.9 |
| Example 3-(1) | 32 | 89.7 |
|  | 10 | 96.2 |
|  | 3.2 | 76.7 |
| Example 28 | 32 | 98.5 |
| Example 37 | 10 | 92.4 |
| Example 39 | 32 | 100.0 |
|  | 10 | 93.0 |
|  | 3.2 | 87.8 |

As being apparent from the above test results, the object compounds [I] of the present invention are useful as cardiotonic medicines and antiulcer medicines.

For therapeutic administration, the object compound [I] of the present invention and pharmaceutically acceptable salts thereof are used in a form of the conventional pharmaceutical preparation in admixture with a conventional pharmaceutically acceptable carrier such as an organic or inorganic solid or liquid excipient which is suitable for oral, parenteral or external administration. The pharmaceutical preparation may be compounded in a solid form such as capsule, tablet, dragee or suppository, or in a liquid form such as solution, suspension or emulsion. If needed, there may be included in the above preparation auxiliary substance, stabilizing agent, wetting or emulsifying agent, buffer or any other commonly used additives.

The effective ingredient may usually be administered with a unit dose of 0.05 mg/kg to 500 mg/kg, 1 to 4 times a day. However, the above dosage may be increased or decreased according to age, weight, conditions of the patient or the administering method.

The following preparation and examples are given only for the purpose of illustrating the present invention in more detail.

Preparation 1

A solution of sulfuryl chloride (2.84 g) in methylene chloride (5 ml) was dropwise added to a solution of ethyl 4-(2-pyridyl)-2,4-dioxobutyrate (4.42 g) in methylene chloride (60 ml) at 8° C. to 25° C. After the mixture was stirred for 30 minutes at ambient temperature, diethyl ether (60 ml) was added thereto. The precipitated crystals were collected by filtration, washed with diethyl ether and dried to give ethyl 3-chloro-4-(2-pyridyl)-2,4-dioxo-butyrate hydrochloride (5.6 g).

IR (Nujol): 1750, 1660, 1615 cm$^{-1}$

EXAMPLE 1

To a solution of thiourea (4.5 g) and sodium acetate (5 g) in a mixture of tetrahydrofuran (50 ml) and water (15 ml) was added ethyl 3-chloro-4-(2-pyridyl)-2,4-dioxobutyrate hydrochloride (5.6 g). After the mixture was stirred at 45° C. to 50° C. for 2 hours, water (50 ml) was added thereto. The resulting mixture was acidified to pH 1.0 with 10% hydrochloric acid. The precipitate was collected by filtration. The precipitate was added to a mixture of water and ethyl acetate, and adjusted to pH 6.0 with 10% potassium carbonate. The separated ethyl acetate layer was washed with brine, dried over magnesium sulfate, and evaporated in vacuo. The residue was recrystallized from a mixture of ethyl acetate and tetrahydrofuran to give ethyl 2-amino-5-(2-pyridinecarbonyl)-4-thiazolecarboxylate (1.1 g).

mp 143°–144° C. IR (Nujol): 3300, 3260, 3060, 1730, 1705, 1690, 1590, 1550 cm$^{-1}$, NMR (DMSO-d$_6$, δ): 1.37 (3H, t, J=7 Hz), 4.42 (2H, q, J=7 Hz), 7.93 (1H, m), 8.50 (1H, m), 8.87 (1H, m), 8.87 (1H, s) Mass. 277 (M$^+$)

EXAMPLE 2

To a solution of 1-(3-pyridyl)-2-propanone (3.4 g) in methylene chloride (30 ml) was dropwise added a solution of sulfuryl chloride (4.0 g) in methylene chloride (5 ml) at 20° C. to 28° C. under stirring and the mixture was stirred at ambient temperature for 30 minutes. The resulting mixture was added to a solution of thiourea (4.2 g) in a mixture of tetrahydrofuran (50 ml) and water (20 ml) and the mixture was adjusted to pH 7.0 to 7.5 with 20% aqueous potassium carbonate. After being stirred at ambient temperature for 2 hours, the mixture was evaporated in vacuo. The residue was dissolved in a mixture water and ethyl acetate, and the mixture was acidified to pH 1.0 with 10% hydrochloric acid. The separated aqueous layer was adjusted to pH 7.5 with 20% aqueous potassium carbonate and extracted with ethyl acetate. The ethyl acetate layer was washed with brine and dried over magnesium sulfate. The solvent was evaporated in vacuo. The residue was washed with a mixture of diethyl ether and ethyl acetate, and recrystallized from tetrahydrofuran to give 2-amino-4-methyl-5-(3-pyridyl)thiazole (1.9 g). mp 190°–191° C.

IR (Nujol): 3230, 1660, 1585, 1530 cm$^{-1}$ NMR (DMSO-d$_6$, δ): 2.23 (3H, s), 7.17 (2H, s), 7.47 (1H, dd, J=5, 8 Hz), 7.80 (1H, dt, J=8, 2 Hz), 8.48 (1H, dd, J=2, 8 Hz), 8.63 (1H, d, J=2 Hz) Mass. 191 (M$^+$)

EXAMPLE 3

The following compounds were obtained according to the substantially same manner as that of Example 2.

(1) 2-Amino-4-methyl-5-(4-pyridyl)thiazole mp 210° C. (dec.) (from ethyl acetate)

IR (Nujol): 3250, 3130, 1610, 1540, 1500 cm$^{-1}$ NMR (DMSO-d$_6$, δ): 2.33 (3H, s), 7.32 (2H, dd, J=2, 4 Hz), 8.48 (2H, dd, J=2, 4 Hz), 7.05 (2H, br. s) Mass. 191 (M$^+$)

(2) 2-Methylamino-4-methyl-5-(3-pyridyl)thiazole mp 152°–153° C. (from ethyl acetate-diethyl ether)

IR (Nujol): 3180, 1640, 1580, 1540 cm$^{-1}$ NMR (DMSO-d$_6$, δ): 2.33 (3H, s), 2.87 (3H, s), 7.37 (1H, dd, J=5, 8 Hz), 7.73 (1H, dt, J=8, 2 Hz), 8.40 (1H, dd, J=2, 8 Hz), 8.55 (1H, d, J=2 Hz) Mass. 205 (M$^+$)

(3) 2-Methylamino-4-methyl-5-(4-pyridyl)thiazole mp 155°–156.5° C. (from ethyl acetate-diethyl ether)

IR (Nujol): 3200, 1605, 1590, 1540, 1520 cm$^{-1}$ NMR (DMSO-d$_6$, δ): 2.38 (3H, s), 2.90 (3H, d, J=4 Hz), 7.32 (2H, dd, J=2, 4 Hz), 7.50 (1H, m), 8.52 (2H, dd, J=2, 4 Hz)

EXAMPLE 4

A solution of sulfuryl chloride (5.4 g) in methylene chloride (5 ml) was added to a solution of 1-(4-pyridyl)-2-propanone (5.4 g) in methylene chloride (50 ml) at 20° C. to 37° C. with stirring and the mixture was stirred at 30° C. to 35° C. for 30 minutes. The reaction mixture was evaporated in vacuo and the residue was dissolved in dimethylacetamide (20 ml). To the resulting solution was added N-phenylthiourea (11 g) and stirred at ambient temperature for 4 hours. The reaction mixture was poured into a mixture of water and ethyl acetate and the resulting mixture was acidified to pH 0.6 with 10% hydrochloric acid. The separated aqueous layer was adjusted to pH 7.5 with 20% aqueous potassium carbonate and extracted with ethyl acetate. The extract was washed with brine and dried over magnesium sulfate. The solvent was removed in vacuo to give a crystalline residue, which was recrystallized from a mixture of ethyl acetate and diethyl ether to afford 2-anilino-4-methyl-5-(4-pyridyl)-thiazole (0.94 g). mp 168°–170° C.

IR (Nujol): 3250, 3200, 1630, 1600, 1570, 1535, 1510 cm$^{-1}$ NMR (DMSO-d$_6$, δ): 2.42 (3H, s), 6.83–7.8 (5H, m), 7.36 (1H, dd, J=2, 4 Hz), 8.53 (1H, dd, J=2, 4 Hz), 10.37 (1H, s)

EXAMPLE 5

The following compounds were obtained according to the substantially same manner as that of Example 4.

(1) 2-Anilino-4-methyl-5-(3-pyridyl)thiazole mp 177.5°–179.5° C. (from ethyl acetate)

IR (Nujol): 3260, 3200, 1625, 1600, 1570, 1520 cm$^{-1}$ NMR (D$_2$O+DCl, δ): 2.27 (3H, s), 7.48 (5H, s), 8.22 (1H, dd, J=5, 8 Hz), 8.72 (1H, dt, J=2, 8 Hz), 8.88 (1H, dd, J=2, 5 Hz), 8.97 (1H, d, J=2 Hz)

(2) 2-(4-Pyridyl)-4-methyl-5-(3-pyridyl)thiazole mp 113°–114° C. (from diethyl ether-ethyl acetate)

IR (Nujol): 1660, 1600, 1560, 1520 cm$^{-1}$ NMR (DMSO-d$_6$, δ): 2.50 (3H, s), 7.53 (1H, dd, J=5, 8 Hz), 7.83 (2H, dd, J=2, 4 Hz), 7.98 (1H, dt, J=2, 8 Hz), 8.62 (1H, dd, J=2, 5 Hz), 8.70 (2H, dd, J=2, 4 Hz), 8.77 (1H, d, J=2 Hz)

EXAMPLE 6

A solution of sulfuryl chloride (2.02 g) in methylene chloride (20 ml) was dropwise added to a solution of 1-(4-pyridyl)-2-butanone (4.9 g) in methylene chloride (75 ml) at 20° to 25° C. with stirring, which was continued under the same condition for 10 minutes. N-Methythiourea (1.35 g) was added thereto and the mixture was stirred at ambient temperature for 2 hours. After addition of methylene chloride (150 ml), the mixture was stirred for 60 minutes. The resulting precipitate was collected by filtration, dried under reduced pressure for 30 minutes and dissolved in water (50 ml). The aqueous solution was adjusted to pH 6.5 with 20% aqueous potassium carbonate and allowed to stand at 5° C. for 3 hours. The resultant precipitate was collected by filtration, washed with water (300 ml×2) and dried over phosphorus pentoxide under reduced pressure to give a yellow powder (1.65 g). The powder was dissolved in hot ethyl acetate (70 ml) and treated with active carbon (200 mg). After removal of the active carbon using cellite, the filtrate was concentrated to the volume of 30 ml at 50° C. under reduced pressure. The resulting crystalline product was collected by filtration, washed with cold ethyl acetate (500 ml×2) and dried under reduced pressure to give 4-ethyl-2-methylamino-5-(4-pyridyl)-thiazole (950 mg). mp 146°–149° C.

IR (Nujol): 3380, 3200, 3100, 1665, 1590, 1545, 1530 cm$^{-1}$ NMR (D$_2$O+DCl, δ): 1.39 (3H, t, J=7 Hz), 3.01 (2H, q, J=7 Hz), 3.26 (3H, s), 8.0–8.3 (2H, m), 8.9–9.1 (2H, m)

EXAMPLE 7

2-Ethylamino-4-ethyl-5-(4-pyridyl)thiazole (0.9 g) was obtained according to substantially the same manner as that of Example 6 from 1-(4-pyridyl)-2-butanone (1.49 g) and N-ethylthiourea (1.56 g). mp 126°–128° C.

IR (Nujol): 3200, 3080, 1580, 1540, 1520, 1330, 1050, 990, 820 cm$^{-1}$ NMR (D$_2$O+DCl, δ): 1.42 (6H, t, J=7 Hz), 3.03 (2H, q, J=7 Hz), 3.62 (2H, q, J=7 Hz), 8.0–8.3 (2H, m), 8.7–9.1 (2H, m)

EXAMPLE 8

2-Ethylamino-4-methyl-5-(4-pyridyl)thiazole (1.5 g) was obtained according to substantially the same manner as that of Example 6 from 1-(4-pyridyl)-2-propanone (2.0 g) and N-ethylthiourea (1.87 g). mp 129°–131° C.

IR (Nujol): 3200, 3100, 1600, 1580, 1545, 1525, 1410, 1330, 1310, 985, 808 cm$^{-1}$ NMR (D$_2$O+DCl, δ): 1.42 (3H, t, J=7 Hz), 2.66 (3H, s), 3.58 (2H, q, J=7 Hz), 8.0–8.3 (2H, m), 8.7–9.1 (2H, m)

EXAMPLE 9

4-Methyl-2-(2-pyridylamino)-5-(4-pyridyl)thiazole (1.1 g) was obtained according to substantially the same manner as that of Example 6 from 1-(4-pyridyl)-2-propanone (1.35 g) and N-(2-pyridyl)thiourea (1.53 g). mp 235°–238° C. (dec.)

IR (Nujol): 3150, 1610, 1590, 1520, 1475, 1400, 1295, 1215, 1150, 995, 825 cm$^{-1}$ NMR (D$_2$O+DCl, δ) 2.70 (3H, s), 7.2–7.6 (2H, m), 7.9–8.5 (4H, m), 8.6–9.0 (2H, m)

EXAMPLE 10

2-(3,4-dimethoxybenzylamino)-4-methyl-5-(4-pyridyl)thiazole (1.3 g) was obtained according to substantially the same manner as that of Example 6 from 1-(4-pyridyl)-2-propanone (1.35 g) and N-(3,4-dimethoxybenzyl)thiourea (2.26 g). mp 134°–135° C.

IR (Nujol): 3180, 3050, 1585, 1550, 1518, 1428, 1410, 1330, 1305, 1255, 1235, 1142 cm$^{-1}$ NMR (D$_2$O+DCl, δ): 3.71 (3H, s), 3.90 (3H, s), 3.96 (3H, s), 4.68 (2H, s), 7.0–7.3 (3H, s), 8.0–8.3 (2H, m), 8.8–9.1 (2H, m)

EXAMPLE 11

A solution of sulfuryl chloride (2.7 g) in methylene chloride (10 ml) was added to a mixture of 1-(4-pyridyl)-pentan-2-one (3.3 g) in methylene chloride (40 ml) at 25° to 40° C. with stirring and the clear solution was stirred at ambient temperature for 30 minutes. The reaction mixture was evaporated to dryness in vacuo and the residue was dissolved in methanol (40 ml), to which was added N-methylthiourea (2.7 g). The resultant mixture was stirred at ambient temperature for 4 hours. The reaction mixture was evaporated in vacuo and the residue was dissolved in water (50 ml), washed with ethyl acetate (50 ml). The aqueous layer was adjusted to pH 7 with 20% aqueous potassium carbonate. The precipitate was collected by filtration and washed with water to give 2-methylamino-4-propyl-5-(4-pyridyl)thiazole (3.04 g).

mp 150°–151° C. IR (Nujol): 3300, 3100, 1580, 1545, 1530, 1400, 1330, 1310 cm$^{-1}$ NMR (D$_2$O+DCl, δ): 1.10 (3H, t, J=9 Hz), 1.1–1.9 (2H, m), 2.73 (2H, t, J=9 Hz), 3.04 (3H, s), 7.62 (2H, d, J=6 Hz), 8.58 (2H, d, J=6 Hz)

EXAMPLE 12

2-Amino-4-propyl-5-(4-pyridyl)thiazole (2.96 g) was obtained according to substantially the same manner as that of Example 11 from 1-(4-pyridyl)-pentan-2-one (4.17 g) and thiourea (2.2 g).

mp 210°–213° C. IR (Nujol): 3220, 1645, 1595, 1530, 1510, 1350, 1310, 1290, 1220, 990 cm$^{-1}$ NMR (D$_2$O+DCl, δ): 1.08 (3H, t, J=9 Hz), 1.6–2.1 (2H, m), 3.00 (2H, t, J=9 Hz), 8.23 (2H, d d., J=2 Hz, 6 Hz), 8.98 (2H, d d., J=2 Hz, 6 Hz)

EXAMPLE 13

4-Isopropyl-2-methylamino-5-(4-pyridyl)thiazole (2.16 g) was obtained according to substantially the same manner as that of Example 11 from 1-(4-pyridyl)-3-methyl-butan-2-one (4.01 g) and N-methylthiourea (2.7 g).

mp 156°–158° C. IR (Nujol): 3200, 3100, 1580, 1540, 1530, 1400, 1330, 1305 cm$^{-1}$ NMR (D$_2$O+DCl, δ): 1.38 (6H, d, J=7 Hz), 3.20 (3H, s), 3.1–3.7 (1H, m), 4.87 (3H, s), 8.08 (2H, d d., J=2 Hz, 6 Hz), 8.85 (2H, d d., J=2 Hz, 6 Hz)

EXAMPLE 14

2-Amino-4-isopropyl-5-(4-pyridyl)thiazole (3.68 g) was obtained according to substantially the same manner as that of Example 11 from 1-(4-pyridyl)-3-methyl-butan-2-one (4 g) and thiourea (2.2 g).

mp 266°–267° C. IR (Nujol): 3250, 3170, 1650, 1595, 1515, 1300 cm$^{-1}$ NMR (D$_2$O+DCl, δ): 1.43 (6H, d, J=8 Hz), 3.3–3.7 (1H, m), 8.14 (2H, d d., J=2 Hz, 6 Hz), 8.93 (2H, d d., J=2 Hz, 6 Hz)

EXAMPLE 15

2-Methylamino-4-methyl-5-(2-pyridyl)thiazole (1.8 g) was obtained according to substantially the same manner as that of Example 11 from 1-(2-pyridyl)acetone (2.03 g) and N-methylthiourea (2.7 g).

mp 279°–282° C. IR (Nujol): 3170, 1620, 1580, 1550, 1295, 1280 cm$^{-1}$ NMR (D$_2$O+DCl, δ): 2.46 (3H, s), 3.20 (3H, s), 8.0–9.0 (4H, m) Mass. 205 (M+)

EXAMPLE 16

2-Amino-4-methyl-5-(2-pyridyl)thiazole (1.35 g) was obtained according to substantially the same manner as that of Example 11 from 1-(2-pyridyl)acetone (2.03 g) and thiourea (2.28 g).

mp 256°–258° C. (dec.). IR (Nujol): 3450, 3400, 3200, 1655, 1620, 1580, 1305 cm$^{-1}$ NMR (D$_2$O+DCl, $\delta$): 2.43 (3H, s), 7.9–9.0 (4H, m) Mass. 191 (M+)

EXAMPLE 17

A solution of sulfuryl chloride (2.7 g) in methylene chloride (10 ml) was added to a mixture of 1-(4-pyridyl)-butan-2-one (3 g) in methylene chloride (50 ml) at 25° to 40° C. with stirring and the clear solution was stirred at ambient temperature for 30 minutes. The reaction mixture was evaporated to dryness in vacuo and to the residue, dissolved in methanol (50 ml), was added N-amidinothiourea (4.72 g). The mixture was stirred for 90 minutes at ambient temperature and for 2 hours under refluxing. The resultant reaction mixture was evaporated to give a residue, which was dissolved in water (50 ml). The aqueous solution was adjusted to pH 7 with aqueous potassium carbonate and extracted with a mixed solvent of chloroform and methanol (10:1). After drying the organic extract over magnesium sulfate, the solvent was removed under reduced pressure. The residue was subjected to column chromatography on silica gel (100 g) and eluted with a mixture of chloroform and methanol (30:1). The fractions containing the object compound were combined and concentrated under reduced pressure to give 2-guanidino-4-ethyl-5-(4-pyridyl)thiazole (0.46 g).

mp 259°–262° C. (dec.) IR (Nujol): 3450, 3240, 3060, 1660, 1590, 1540 cm$^{-1}$ NMR (D$_2$O+DCl, $\delta$): 1.36 (3H, t, J=8 Hz), 3.02 (2H, q, J=8 Hz), 8.08 (2H, d d., J=2 Hz, 5.5 Hz), 8.78 (2H, d d., J=2 Hz, 5.5 Hz) Mass. 247 (M+)

EXAMPLE 18

2-Guanidino-4-methyl-5-(3-pyridyl)thiazole (0.25 g) was obtained according to substantially the same manner as that of Example 17 from 1-(3-pyridyl)acetone (2.7 g) and N-amidinothiourea (4.72 g).

mp 201°–206° C. (dec.). IR (Nujol): 3450, 3320, 3130, 1650, 1595, 1310, 1245, 1005 cm$^{-1}$ NMR (D$_2$O+DCl, $\delta$): 2.46 (3H, s), 8.17 (1H, d.d., J=6 Hz, 8 Hz), 8.70 (1H, d d., J=2 Hz, 8 Hz), 8.82 (1H, d d., J=2 Hz, 6 Hz), 8.95 (1H, d, J=2 Hz) Mass. 233 (M+)

EXAMPLE 19

2-Guanidino-4-methyl-5-(2-pyridyl)thiazole (0.16 g) was obtained according to substantially the same manner as that of Example 17 from 1-(2-pyridyl)acetone (2.8 g) and N-amidinothiourea (1.18 g).

mp 166°–168° C. IR (Nujol): 3440, 3400, 3270, 3080, 1630, 1600, 1580, 1540, 1520, 1420, 1320, 1240 cm$^{-1}$ NMP (DMSO-d$_6$, $\delta$): 2.42 (3H, s), 6.8–7.1 (1H, m), 7.36 (1H, d, J=7 Hz), 7.5–7.8 (1H, m), 8.33 (1H, d d., J=2 Hz, 7 Hz) Mass. 233 (M+)

EXAMPLE 20

A solution of sulfuryl chloride (4.5 g) in methylene chloride (5 ml) was added to a solution of ethyl 3-(pyridine-N-oxide-4-yl)-2-oxo-propionate (6.3 g) in methylene chloride (100 ml) at 20° C. to 32° C. and the resulting mixture was stirred at ambient temperature for an hour. The reaction mixture was evaporated in vacuo. The residue was dissolved in dimethylacetamide (30 ml) and N-phenyl thiourea (12.4 g) was added thereto. The resulting mixture was stirred at ambient temperature for 7 hours and the reaction mixture was poured into diisopropyl ether (200 ml). The precipitate was collected by filtration and added to a mixture of water and ethyl acetate. The mixture was acidified to pH 1.0 with 10% hydrochloric acid. The precipitate was collected by filtration, washed successively with water and ethyl acetate and dried over phosphorus pentoxide to give ethyl 2-anilino-5-(pyridine-N-oxide-4-yl)-4-thiazolecarboxylate (2.1 g).

IR (Nujol): 1710, 1625, 1600, 1565, 1540, 1520 cm$^{-1}$ NMR (DMSO-d$_6$, $\delta$): 1.17 (3H, t, J=7 Hz), 2.22 (2H, q, J=7 Hz), 6.8–7.8 (5H, m), 7.42 (2H, d, J=7 Hz), 8.25 (2H, d, J=7 Hz), 10.6 (1H, s)

EXAMPLE 21

Ethyl 2-amino-5-(pyridine-N-oxide-4-yl)-4-thiazolecarboxylate was obtained according to the substantially same manner as that of Example 20. mp 258° C. (dec.)

IR (Nujol): 3220, 3100, 1715, 1625, 1550 cm$^{-1}$ NMR (DMSO-d$_6$, $\delta$): 1.27 (3H, t, J=7 Hz), 4.37 (2H, q, J=7 Hz), 8.00 (2H, d, J=7 Hz), 8.56 (2H, d, J=7 Hz)

EXAMPLE 22

A solution of sulfuryl chloride (8.1 g) in methylene chloride 85 ml) was added to a mixture of ethyl 3-(pyridine-N-oxide-4-yl)-2-oxo-propionate (12.6 g) and methylene chloride (200 ml) at 20° C. to 33° C. with stirring and the clean solution was stirred at ambient temperature for an hour. The reaction mixture was evaporated in vacuo to dryness and the residue was dissolved in ethanol (200 ml), to which was added N-methylthiourea (12.6 g). The resultant mixture was stirred at 60° C. to 70° C. for 10 hours. The reaction mixture was evaporated in vacuo and the residue was dissolved in water. The aqueous solution was adjusted to pH 8 with 20% aqueous potassium carbonate and extracted with chloroform. The organic extract was dried over magnesium sulfate. The solvent was removed in vacuo to give ethyl 2-methylamino-5-(pyridine-N-oxide-4-yl)-4-thiazolecarboxylate (9.9 g).

IR (Nujol) 3180, 1716, 1585, 1545 cm$^{-1}$ NMR (DMSO-d$_6$, $\delta$): 1.17 (3H, t, J=7 Hz), 2.90 (3H, d, J=4 Hz), 4.80 (2H, q, J=7 Hz), 7.45 (2H, dd, J=2, 4 Hz), 8.03 (1H, q, J=4 Hz), 8.20 (2H, dd, J=2, 4 Hz)

EXAMPLE 23

Ethyl 2-amino-5-(pyridine-N-oxide-2-yl)-4-thiazolecarboxylate (9.7 g) was obtained according to substantially the same manner as that of Example 22 from ethyl 3-(pyridine-N-oxide-2-yl)-2-oxo-propionate (10 g), sulfuryl chloride (4.05 ml) and thiourea (10.96 g). mp 225°–227° C.

IR (Nujol): 3250, 3100, 1715, 1620, 1540 cm$^{-1}$ NMR (DMSO-d$_6$, $\delta$): 1.1 (3H, t, J=6 Hz), 4.15(2H, q, J=6 Hz), 7.13–7.73(5H, m), 8.3(1H, m)

EXAMPLE 24

Ethyl 2-methylamino-5-(pyridine-N-oxide-2-yl)-4-thiazolecarboxylate (5.16 g) was obtained according to substantially the same manner as that of Example 22 from ethyl 3-(pyridine-N-oxide-2-yl)-2-oxo-propionate (10 g), sulfuryl chloride (4.05 ml) and N-methylthiourea (12.98 g). mp 128°–131° C.

IR (Nujol): 3200, 3100, 1720, 1600 cm$^{-1}$ NMR (DMSO-d$_6$, δ): 1.13 (3H, t, J=7 Hz), 2.87 (3H, d,J=4 Hz), 4.18 (2H, q, J=8 Hz), 7.2–7.6 (3H, m), 7.97 (1H, q, J=4 Hz), 8.3 (1H, d d, J=3, 4 Hz)

EXAMPLE 25

Ethyl 2-guanidino-5-(pyridine-N-oxide-4-yl)-4-thiazolecarboxylate (2.4 g) was obtained according to substantially the same manner as that of Example 22 from ethyl 3-(pyridine-N-oxide-4-yl)-2-oxo-propionate (4.18 g), sulfuryl chloride (1.62 ml) and 1-thiocarbamoylguanidine (4.73 g).

EXAMPLE 26

A solution of sulfuryl chloride (2.84 g) in methylene chloride (5 ml) was dropwise added to a solution of ethyl 4-(3-pyridyl)-2,4-dioxo-butyrate (4.42 g) in methylene chloride (40 ml) at 18° C. to 30° C. After being stirred at ambient temperature for one hour, the mixture was added to a solution of thiourea (4.56 g) in a mixture of tetrahydrofuran (50 ml) and water (10 ml). The resulting mixture was adjusted to pH 7.5 with 20% aqueous potassium carbonate and stirred for one hour, and then the solvent was removed in vacuo. To the residue was added a mixture of water and ethyl acetate, and the mixture is acidified to pH 1.0 with 10% hydrochloric acid. The separated aqueous layer was adjusted to pH 9.0 with 20% aqueous potassium carbonate and extracted with ethyl acetate. The extract was dried over magnesium sulfate and evaporated in vacuo. The residue was recrystallized from a mixture of ethyl acetate and tetrahydrofuran to give ethyl 2-amino-5-nicotinoyl-4-thiazolecarboxylate (0.9 g). mp 221° C. (dec.)

IR (Nujol): 3100, 1740, 1680, 1590, 1510 cm$^{-1}$ NMR (DMSO-d$_6$, δ): 1.33 (3H, t, J=7 Hz), 4.35 (2H, q, J=7 Hz), 7.50 (1H, dd, J=5, 8 Hz), 7.97 (1H, s), 8.30 (1H, dt, J=2, 8 Hz), 8.58 (1H, dd, J=5, 8 Hz), 9.22 (1H, d, J=2 Hz), 12.67–13.33 (1H, m) Mass. 277 (M+)

EXAMPLE 27

2-Amino-4-methyl-5-nicotinoylthiazole was obtained according to the substantially same manner as that of Example 26. mp 287°–288° C. (from ethyl acetatetetrahydrofuran)

IR (Nujol): 1670, 1575 cm$^{-1}$ NMR (DMSO-d$_6$, δ): 2.17 (3H, s), 7.50 (1H, dd, J=6, 8 Hz), 7.75 (1H, s), 8.22 (1H, dt, J=2, 8 Hz), 8.52 (1H, dd, J=2, 6 Hz), 9.12 (1H, d, J=2 Hz)

EXAMPLE 28

A solution of sulfuryl chloride (2.84 g) in methylene chloride (5 ml) was dropwise added to a solution of ethyl 4-(3-pyridyl)-2,4-dioxo-butyrate (4.42 g) in methylene chloride (40 ml) at 8° C. to 21° C. and the mixture was stirred at ambient temperature for 30 minutes. The precipitate was collected by filtration, washed with diethyl ether, and added to a solution of thiourea (4.5 g) and sodium acetate (5.0 g) in a mixture of tetrahydrofuran (50 ml) and water (15 ml). The resulting mixture was stirred at 25° C. to 50° C. for 2.5 hours. To the reaction mixture was added water (15 ml) and the mixture was acidified to pH 1.0 with 10% hydrochloric acid. The precipitate, collected by filtration and washed successively with water and ethyl acetate, was added to a mixture of water and ethyl acetate, and the mixture was adjusted to pH 5.0 with 20% aqueous potassium carbonate. The separated ethyl acetate layer was washed with brine, dried over magnesium sulfate, and evaporated in vacuo. The residue was recrystallized from a mixture of ethyl acetate and tetrahydrofuran to give ethyl 2-amino-5-(2-pyridinecarbonyl)-4-thiazolecarboxylate (1.1 g). mp 143°–144° C.

IR (Nujol): 3300, 3260, 3060, 1730, 1705, 1690, 1590, 1550 cm$^{-1}$ NMR (DMSO-d$_6$, δ): 1.37 (3H, t, J=7 Hz), 4.42 (2H, q, J=7 Hz), 7.93 (1H, m), 8.50 (1H, m), 8.57 (1H, m), 8.87 (1H, s), 8.87 (1H, m) Mass. 277 (M+)

EXAMPLE 29

To a solution of acetylacetone (30 g) in carbon tetrachloride (80 m) was dropwise added sulfuryl chloride (40.5 g) under ice-cooling with stirring and the mixture was stirred at ambient temperature for one hour. The reaction mixture was evaporated in vacuo and the residue was added to a solution of thiourea (45.6 g) in ethanol (200 ml). The resulting mixture was stirred at ambient temperature for 3 hours. The precipitate was collected by filtration.

The filtrate was concentrated in vacuo and the second crop of precipitate was collected by filtration.

The combined precipitate was added to water (400 ml) and the mixture was acidified to pH 1.0 with 10% hydrochloric acid. The resulting precipitate was collected by filtration, washed successively with water and ethyl acetate, and dried over phosphorus pentoxide to give 5-acetyl-2-amino-4-methylthiazole (35.0 g). mp 272° C. (dec.)

IR (Nujol): 3250, 1660, 1600 cm$^{-1}$ NMR (DMSO-d$_6$, δ): 2.50 (3H, s), 2.58 (3H, s), 5.87 (2H, br. s)

EXAMPLE 30

To a solution of ethyl 2,4-dioxo-valerate (39.2 g) in carbon tetrachloride (60 ml) was dropwise added sulfuryl chloride (33.5 g) under ice-cooling with stirring and the mixture was stirred at ambient temperature for one hour. The reaction mixture was evaporated in vacuo. The residue was added to a solution of thiourea (16.7 g) in ethanol (100 ml) and stirred at ambient temperature for 3 hours. To the mixture was added a solution of water (400 ml), ethyl acetate (500 ml) and tetrahydrofuran (100 ml), and the resulting mixture was adjusted to pH 8.0 with 20% potassium carbonate. The separated organic layer was washed with brine, dried over magnesium sulfate, and evaporated in vacuo. The residue was washed with diisopropyl ether to give ethyl 5-acetyl-2-amino-4-thiazolecarboxylate (32.7 g). mp 162°–164° C.

IR (Nujol): 3400, 3250, 3100, 1720, 1620 cm$^{-1}$ NMR (DMSO-d$_6$, δ): 1.30 (3H, t, J=7 Hz), 2.30 (3H, s), 4.32 (2H, q, J=7 Hz), 8.07 (2H, s)

EXAMPLE 31

To a solution of ethyl 2,4-dioxohexanate (51.7 g) in carbon tetrachloride (100 ml) was dropwise added sulfuryl chloride (41.1 g) at ambient temperature with stirring, which was continued at the same temperature for 3 hours. The reaction mixture was evaporated in vacuo and the residue was added to a solution of thiourea (45 g) in ethanol (200 ml). The mixture was stirred at ambient temperature for 4 hours. The resultant mixture was evaporated in vacuo and the residue was dissolved in a mixture of ethyl acetate and water. The separated organic layer was washed with 10% hydrochloric acid and brine and dried over magnesium sulfate. The solvent was evaporated in vacuo and the residue was washed with ether to give ethyl 2-amino-5-propionyl-4-thiazolecarboxylate (8.9 g).

mp 134°-135° C. IR (Nujol): 3400, 3250, 1730, 1620 cm$^{-1}$ NMR (DMSO-d$_6$, δ): 1.03 (3H, t, J=7 Hz), 1.32 (3H, t, J=7 Hz), 2.68 (2H, q, J=7 Hz), 4.35 (2H, q, J=7 Hz), 8.07 (2H, s)

EXAMPLE 32

To a solution of ethyl 2,4-dioxohexanoate (45 g) in carbon tetrachloride (100 ml) was dropwise added sulfuryl chloride (35.3 g) at 35° to 40° C. with stirring and the resultant mixture was stirred at the same temperature for 1.5 hours. The reaction mixture was evaporated in vacuo and the residue was added to a solution of N-methylthiourea (46.8 g) in ethanol (200 ml). The resultant mixture was stirred for 4 hours at 40° to 50° C. The reaction mixture was evaporated in vacuo and the residue was dissolved in a mixture of ethyl acetate and water. The separated organic layer was washed with 10% hydrochloric acid and brine successively and dried over magnesium sulfate. The solvent was evaporated in vacuo to afford a crystalline residue, which was recrystallized from a mixture of ethyl acetate and diethyl ether to give ethyl 2-methylamino-5-propionyl-4-thiazolecarboxylate (7.5 g). mp 84°-6° C.

IR (Nujol): 3200, 1725, 1630 cm$^{-1}$ NMR (DMSO-d$_6$, δ): 1.02 (3H, t, J=7 Hz), 1.32 (3H, t, J=7 Hz), 2.67 (2H, q, J=7 Hz), 2.87 (3H, d, J=5 Hz), 4.33 (2H, q, J=7 Hz), 8.68 (1H, q, J=5 Hz)

EXAMPLE 33

2-Methylamino-4-methyl-5-acetylthiazole (38.5 g) was obtained according to substantially the same manner as that of Example 32 from acetylacetone (50.06 g) and N-methylthiourea (67.6 g). mp 164°-165° C.

NMR (DMSO-d$_6$, δ): 2.36 (3H, s), 2.46 (3H, s), 2.86 (3H, d, J=2 Hz), 8.2-8.4 (3H, br.)

EXAMPLE 34

To a solution of 1-(3-pyridyl)-2-propanone (4.5 g) in methylene chloride (30 ml) was dropwise added a solution of sulfuryl chloride (4.6 g) in methylene chloride (5 ml) at 20° C. to 37° C. with stirring and the mixture was stirred at ambient temperature for 30 minutes. The reaction mixture was evaporated in vacuo and the residue was added to a solution of ethyl thiocarbamate (4.4 g) and triethylamine (13.2 g) in ethanol (40 ml). The resulting mixture was refluxed for 4.5 hours with stirring. The reaction mixture was evaporated in vacuo and the residue was dissolved in water. The solution was acidified to pH 1.0 with 10% hydrochloric acid and washed with ethyl acetate. The aqueous layer was adjusted to pH 7.5 with 20% aqueous potassium carbonate and extracted with ethyl acetate. The extract was washed with brine, dried over magnesium sulfate, and evaporated in vacuo. The residue was subjected to column chromatography on alumina and eluted with ethyl acetate. The fractions containing the desired compound were combined and evaporated in vacuo. The oily residue was dissolved in methanolic solution of hydrogen chloride and evaporated in vacuo. The residue was recrystallized from a mixture of methanol and diethyl ether to give 2-hydroxy-4-methyl-5-(3-pyridyl)thiazole hydrochloride (0.5 g). mp 185° C. (dec.)

IR (Nujol): 3360, 2450, 1660, 1608, 1550 cm$^{-1}$ NMR (DMSO-d$_6$, δ): 2.28 (3H, s), 8.00 (1H, dd, J=5, 8 Hz), 8.45 (1H, dd, J=2, 8 Hz), 8.67-8.93 (2H, m), 12.05 (1H, br. s) Mass. 192 (M$^+$)

EXAMPLE 35

A solution of sulfuryl chloride (6.75 g) in methylene chloride (5 ml) was added to a solution of 1-(4-pyridyl)-2-propanone (6.75 g) in methylene chloride (50 ml) at 20° C. to 37° C. with stirring and the mixture was further stirred at 30° C. to 35° C. for an hour. The reaction mixture was evaporated in vacuo. To the residue was added a solution of ethyl thiocarbamate (7.4 g) in ethanol (80 ml) and the resulting mixture was refluxed with stirring for 5 hours. The reaction mixture was evaporated in vacuo and the residue was dissolved in a mixture of water and ethyl acetate. The resulting mixture was acidified to pH 0.6 with 10% hydrochloric acid and the layers were separated. The separated aqueous layer was adjusted to pH 7.5 with 20% aqueous potassium carbonate and extracted with ethyl acetate. The extract was washed with brine, dried over magnesium sulfate and concentrated in vacuo to give a precipitate, which was washed with diisopropyl ether to afford 2-hydroxy-4-methyl-5-(4-pyridyl)thiazole (0.2 g). mp 266°-267° C. (dec.)

IR (Nujol): 1670, 1600, 1580 cm$^{-1}$ NMR (DMSO-d$_6$, δ): 2.23 (3H, s), 7.28 (2H, dd, J=2, 4 Hz), 8.55 (2H, dd, J=2, 4 Hz), 11.58 (1H, br s)

EXAMPLE 36

To a solution of ethyl 2,4-dioxo-valerate (47.5 g) in carbon tetrachloride (80 ml) was dropwise added sulfuryl chloride (40.5 g) under ice-cooling with stirring and the mixture was stirred at ambient temperature for one hour. The reaction mixture was evaporated in vacuo and the residue was added to a solution of ethyl thiocarbamate (32.6 g) in ethanol (100 ml). The mixture was refluxed for 3 hours with stirring. The reaction mixture was cooled and the precipitated crystals were collected by filtration, washed with diethyl ether, and recrystallized from a mixture of ethanol and diethyl ether to give ethyl 5-acetyl-2-hydroxy-4-thiazolecarboxylate (13.5 g).

The filtrate was evaporated in vacuo and the residue was triturated with a mixture of diethyl ether and diisopropyl ether to give the second crop of the desired compound (25.9 g). mp 105°-108° C.

IR (Nujol): 3130, 1740, 1680 (shoulder), 1650, 1560 cm$^{-1}$ NMR (DMSO-d$_6$, δ): 1.33 (3H, t, J=7 Hz), 2.40 (3H, s), 4.37 (2H, q, J=7 Hz)

EXAMPLE 37

A mixture of ethyl 2-amino-5-(pyridine-N-oxide-4-yl)-4-thiazolecarboxylate (3.0 g) and phosphorus trichloride (6.1 g) in methylene chloride (240 ml) was refluxed with stirring for 30 minutes. The reaction mixture was poured into ice-water and the resulting solution was adjusted to pH 7.0 with 20% aqueous potassium carbonate. The mixture was extracted with methylene chloride. The extract was washed with brine, dried over magnesium sulfate and evaporated in vacuo. The residue was recrystallized from a mixture of ethyl acetate and diethyl ether to give ethyl 2-amino-5-(4-pyridyl)-4-thiazolecarboxylate (1.15 g). mp 205°-206° C. (dec.)

IR (Nujol): 3200, 3080, 1715, 1620, 1595, 1540 cm$^{-1}$ NMR (DMSO-d$_6$, δ): 1.13 (3H, t, J=7 Hz), 4.15 (2H, q, J=7 Hz), 7.38 (2H, dd, J=2, 4 Hz), 7.50 (2H, s), 8.52 (2H, dd, J=2, 4 Hz) Mass. 249 (M$^+$)

EXAMPLE 38

Ethyl 2-anilino-5-(4-pyridyl)-4-thiazolecarboxylate was obtained according to the substantially same manner as that of Example 37. mp 167°–169° C. (from ethyl acetate-diethyl ether)

IR (Nujol): 3250, 3200, 1700, 1625, 1600, 1570, 1530 cm$^{-1}$ NMR (DMSO-d$_6$, δ): 1.15 (3H, t, J=7 Hz), 4.20 (2H, q, J=7 Hz), 6.83–7.83 (5H, m), 7.45 (2H, dd, J=2, 4 Hz), 8.62 (2H, dd, J=2, 4 Hz), 10.58 (1H, s) Mass. 325 (M+)

EXAMPLE 39

To a mixture of ethyl 2-methylamino-5-(pyridine-N-oxide-4-yl)-4-thiazolecarboxylate (9.9 g) in methylene chloride (300 ml) was added to phosphorus trichloride (19.4 g) at 15°–30° C. with stirring, which was continued under the same condition for an hour. The reaction mixture was poured into ice-water (300 ml) and the aqueous layer was separated. The aqueous solution was adjusted to pH 8.0 with 20% potassium carbonate and extracted with chloroform. The organic extract was washed with brine, dried over magnesium sulfate and evaporated in vacuo. The residue was recrystallized from a mixture of ethyl acetate and tetrahydrofuran to afford ethyl 2-methylamino-5-(4-pyridyl)-4-thiazolecarboxylate (5.8 g). mp 136°–138° C.

IR (Nujol): 3180, 3110, 1710, 1603, 1590 cm$^{-1}$ NMR (DMSO-d$_6$, δ): 1.17 (3H, t, J=7 Hz), 2.90 (3H, d, J=5 Hz), 4.20 (2H, q, J=7 Hz), 7.40 (2H, dd, J=2, 5 Hz), 8.05 (1H, q, J=4 Hz), 8.58 (2H, dd, J=2, 5 Hz)

EXAMPLE 40

Ethyl 2-amino-5-(2-pyridyl)-4-thiazolecarboxylate (3.26 g) was obtained according to substantially the same manner as that of Example 39 from ethyl 2-amino-5-(pyridine-N-oxide-2-yl)-5-thiazolecarboxylate (9.55 g) and phosphorus trichloride (12.56 g). mp 186°–187° C.

IR (Nujol): 3350, 3250, 3100, 1710, 1620 cm$^{-1}$ NMR (DMSO-d$_6$, δ): 1.2 (3H, t, J=7 Hz), 4.23(2H, q, J=7 Hz), 7.1–7.5(3H, m), 7.55(2H, dd, J=2, 5 Hz), 8.5(1H, dd, J=2, 5 Hz)

EXAMPLE 41

Ethyl 2-methylamino-5-(2-pyridyl)-4-thiazolecarboxylate (2.65 g) was obtained according to substantially the same manner as that of Example 39 from ethyl 2-methylamino-5-(pyridine-N-oxide-2-yl)-5-thiazolecarboxylate (5.16 g) and phosphorus trichloride (6.46 g). mp 120°–121° C.

IR (Nujol): 3180, 3100, 1710, 1570, 1510 cm$^{-1}$ NMR (DMSO-d$_6$, δ): 1.23 (3H, t, J=7 Hz), 2.87(3H, d J=5 Hz), 4.27(2H, q, J=7 Hz), 7.1–7.4(1H, m), 7.57–8.07(3H, m), 8.5(1H, dd, J=2, 5 Hz)

EXAMPLE 42

Ethyl 2-guanidino-5-(pyridine-N-oxide-4-yl)-4-thiazolecarboxylate (1.3 g) was added to a mixture of dimethylformamide (23 ml) and chloroform (23 ml). To the mixture was dropwise added a solution of phosphorus trichloride (2.36 g) in chloroform (13 ml) over a period of 5 minutes at −15° to −10° C. The mixture was stirred for 30 minutes under the same condition and for 30 minutes at 0° to 10° C. The reaction mixture was evaporated under reduced pressure to give a residue, and water (30 ml) was added thereto. The resulting mixture was adjusted to pH 10 with 20% aqueous potassium carbonate and extracted twice with chloroform (30 ml). The organic extract was dried over magnesium sulfate and evaporated under reduced pressure to give a residue, which was subjected to column chromatography on silica gel (120 g) eluting with a mixture of chloroform and methanol (40:1). The fractions containing the desired compound were combined and evaporated under reduced pressure to give a residue. The residue was recrystallized from chloroform to give ethyl 2-(3-dimethylaminomethylideneguanidino)-5-(4-pyridyl)-4-thiazolecarboxylate (0.6 g) as pale yellow needles. mp 203°–204° C.

IR (Nujol): 3300, 3140, 1715, 1615, 1595, 1420, 1320, 1225, 1190 cm$^{-1}$

NMR (DMSO-d$_6$, δ): 1.13 (3H, t, J=7 Hz), 3.04(3H, s), 3.14 (3H, s), 4.18 (2H, q, J=7 Hz), 7.42 (2H, d, J=6 Hz), 8.0 (2H, brs), 8.52 (1H, s), 8.58 (2H, d, J=6 Hz) Mass. 346 (M+)

EXAMPLE 43

A solution of sulfuryl chloride (b 5.7 g) in methylene chloride (5 ml) was added to a mixture of ethyl 3-(pyridine-N-oxide-4-yl)-2-oxo-propionate (6.3 g) in methylene chloride (100 ml) at 20° to 33° C. with stirring and the solution was stirred at ambient temperature for an hour. The reaction mixture was evaporated in vacuo and the residue was dissolved in ethanol (100 ml), to which O-ethyl thiocarbamate (6.3 g) was added. The resultant mixture was refluxed for 10 hours with stirring. The reaction mixture was evaporated in vacuo and the residue was dropwise added to diisopropyl ether (200 ml) with stirring and the solution was decanted. The oil residue was dissolved in methylene chloride (200 ml). To the solution was added phosphorus trichloride (8.1 g) at ambient temperature and the resultant mixture was refluxed for an hour with stirring. The reaction mixture was poured into ice-water and adjusted to pH 7.9 with 20% aqueous potassium carbonate. The organic layer was washed with brine, dried over magnesium sulfate and evaporated in vacuo. The residue was recrystallized from methylene chloride to give ethyl 2-hydroxy-5-(4-pyridyl)-4-thiazolecarboxylate (1.3 g). mp 204°–206° C.

IR (Nujol): 1710, 1602, 1580 cm$^{-1}$ NMR (DMSO-d$_6$, δ): 1.1 (3H, t, J=7 Hz), 4.17 (2H, q, J=7 Hz), 7.50 (2H, dd, J=2, 5 Hz), 8.65 (2H, dd, J=2, 5 Hz), 12.17 (1H, m) Mass. 250 (M+)

EXAMPLE 44

To a suspension of 2-amino-4-methyl-5-acetylthiazole (15.6 g) in 30% solution of hydrogen bromide in acetic acid (120 ml) was added pyridinium hydrobromide perbromide (36 g) at ambient temperature and the mixture was stirred at the same temperature for 5 hours. The precipitate was collected by filtration, washed with diisopropyl ether, and dried over calcium chloride to give 2-amino-4-methyl-5-(2-bromoacetyl)thiazole hydrobromide (26.8 g).

IR (Nujol): 1660, 1620, 1600, 1540 cm$^{-1}$

EXAMPLE 45

To a solution of ethyl 5-acetyl-2-amino-4-thiazolecarboxylate (12.9 g) in a mixture of 30% solution of hydrogen bromide in acetic acid (50 ml) and acetic acid (50 ml) was added pyridinium hydrobromide perbromide (21.1 g) at ambient temperature and stirred for one hour. The reaction mixture was poured into water and extracted with ethyl acetate. The extract was washed with brine, dried over magnesium sulfate, and evaporatec in vacuo. The residue was washed with diisopropyl ether to give ethyl 2-amino-5-(2-bromoacetyl)-4-thiazolecarboxylate (14.86 g). mp 164°–166° C. (dec.)

IR (Nujol): 3400–3200, 1725, 1620 cm$^{-1}$ NMR (DMSO-d$_6$, δ): 1.33 (3H, t, J=7 Hz), 4.33 (2H, q, J=7 Hz), 4.47 (2H, s), 8.08 (4H, br. s)

EXAMPLE 46

To a mixture of ethyl 5-acetyl-2-methylamino-4-thiazolecarboxylate (7.1 g), 30% acetic acid solution of hydrogen bromide (10 ml) and acetic acid (50 ml) was added pyridinium hydrobromide perbromide (9.9 g) at ambient temperature and stirred for 2.5 hours. The reaction mixture was poured into water (300 ml) and the precipitate was collected by filtration. The precipitate was dissolved in a mixture of ethyl acetate and water and the resultant mixture was adjusted to pH 7.0 with 20% aqueous potassium carbonate. The organic extract was washed with brine, dried over magnesium sulfate and evaporated in vacuo. The residue was washed with ethyl ether to give ethyl 5-(2-bromoacetyl)-2-methylamino-4-thiazolecarboxylate (6.6 g). mp 130°–131.5° C.

IR (Nujol): 3300, 3100, 1720, 1640, 1620, 1520 cm$^{-1}$ NMR (DMSO-d$_6$, δ): 1.30 (3H, t, J=7 Hz), 2.90 (3H, s), 4.32 (2H, q, J=7 Hz), 4.45 (2H, s), 8.85 (1H, m)

EXAMPLE 47

Ethyl 2-amino-5-(2-bromopropionyl)-4-thiazolecarboxylate (11.0 g) was obtained according to substantially the same manner as that of Example 46 from ethyl 2-amino-5-propionyl-4-thiazolecarboxylate (8.7 g) and pyridinium hydrobromide perbromide (12.8 g). mp 158°–160° C.

IR (Nujol): 3400, 3300, 1725, 1640, 1620 cm$^{-1}$ NMR (DMSO-d$_6$, δ): 1.16 (3H, t, J=7 Hz), 1.70 (3H, d, J=7 Hz), 4.32 (2H, q, J=7 Hz), 5.70 (1H, q, J=7 Hz)

EXAMPLE 48

To a solution of ethyl 2-methylamino-5-propionyl-4-thiazolecarboxylate (7.4 g) and 30% hydrogen bromide acetic acid (10 ml) in acetic acid (50 ml) was added pyridinium hydrobromide perbromide (13.0 g) at ambient temperature and the mixture was stirred for an hour. The reaction mixture was poured into water and extracted with ethyl acetate. The extract was washed with brine and dried over magnesium sulfate. The solvent was evaporated in vacuo to afford a crystalline residue, which was recrystallized from a mixture of ethyl acetate and diisopropyl ether to give ethyl 2-methylamino-5-(2-bromopropionyl)-4-thiazolecarboxylate (7.4 g).

mp 104°–106° C. IR (Nujol): 3200, 1735, 1633, 1600, 1510 cm$^{-1}$ NMR (DMSO-d$_6$, δ): 1.28 (3H, t, J=7 Hz), 1.68 (3H, d, J=7 Hz), 2.90 (3H, d, J=4 Hz), 4.32 (2H, q, J=7 Hz), 5.13 (2H, q, J=7 Hz), 8.80 (1H, m)

EXAMPLE 49

5-(Bromoacetyl)-2-(N-methylformamido)-4-methylthiazole (16.87 g) was obtained according to substantially the same manner as that of Example 48 from 5-acetyl-2-(N-methylformamido)-4-methylthiazole (16.18 g) and pyridinium hydrobromide perbromide (26.11 g). mp 80°–82° C.

NMR (DMSO-d$_6$, δ): 2.66 (3H, s), 3.6 (3H, s), 4.68 (2H, s), 8.92 (1H, s) IR (Nujol): 1685, 1665 cm$^{-1}$

EXAMPLE 50

A solution of bromine (19.2 g) in methylene chloride (10 ml) was dropwise added to a solution of 5-acetyl-2-hydroxyl-4-methylthiazol (15.7 g) in a mixture of methylene chloride (300 ml) and acetic acid (50 ml) at 40° C. to 44° C. with stirring. After being stirred at the same temperature for 30 minutes, the reaction mixture was poured into water (300 ml). The separated organic layer was washed with brine, dried over magnesium sulfate, and evaporated in vacuo. The residue was triturated with diisopropyl ether to give 5-(2-bromoacetyl)-2-hydroxy-4-methylthiazole (11.75 g). mp 162° C.

IR (Nujol): 1670, 1640, 1580 cm$^{-1}$ NMR (DMSO-d$_6$, δ): 2.43 (3H, s), 4.50 (2H, s)

EXAMPLE 51

A solution of bromine (10.8 g) in methylene chloride (5 ml) was dropwise added to a solution of ethyl 5-acetyl-2-hydroxy-4-thiazolecarboxylate (12.9 g) in a mixture of methylene chloride (150 ml) and acetic acid (10 ml) at 30° C. to 35° C. with stirring and the mixture was stirred at the same temperature for 30 minutes. An insoluble material was filtered off. The filtrate was washed with brine, dried over magnesium sulfate, and evaporated in vacuo. The residue was triturated with diisopropyl ether to give ethyl 5-(2-bromoacetyl)-2-hydroxy-4-thiazolecarboxylate (16.7 g). mp 105°–108° C.

IR (Nujol): 3130, 1735, 1685, 1660, 1560 cm$^{-1}$ NMR (DMSO-d$_6$, δ): 1.33 (3H, t, J=7 Hz), 4.38 (2H, q, J=7 Hz), 4.67 (2H, s)

EXAMPLE 52

A solution of 2-amino-4-methyl-5-(2-bromoacetyl)-thiazole hydrobromide (9.5 g) and 2-amino-3-methylpyridine (9.7 g) in dimethylacetamide (100 ml) was heated at 85° C. to 88° C. for 5 hours and the reaction mixture was evaporated in vacuo. To the residue was added water and the resulting mixture was acidified to pH 0.8 with 10% hydrochloric acid. The acidified solution was treated with charcoal and filtered. The filtrate was washed with ethyl acetate. The aqueous solution was adjusted to pH 9.0 with aqueous potassium carbonate and extracted with ethyl acetate. The extract was dried over magnesium sulfate and evaporated in vacuo. The residue was recrystallized from a mixture of ethyl acetate and tetrahydrofuran to give 2-(2-amino-4-methyl-5-thiazolyl)-8-methylimidazo[1,2-a]pyridine (1.6 g). mp 226° C. (dec.)

IR (Nujol): 3300, 3050, 1620, 1600, 1520 cm$^{-1}$ NMR (DMSO-d$_6$, δ): 2.33 (3H, s), 2.47 (3H, s), 6.78 (1H, dd, J=7 Hz), 7.00 (1H, d, J=7 Hz), 6.92 (2H, s), 7.93 (1H, s), 8.32 (1H, d, J=7 Hz)

EXAMPLE 53

A solution of 2-amino-4-methyl-5-(2-bromoacetyl)-thiazole hydrobromide (7.2 g), 2-aminopyrimidine (3.8 g) and triethylamine (11 ml) in ethanol (200 ml) was refluxed for 8 hours and the reaction mixture was evaporated in vacuo. To the residue was added water and the resulting mixture was acidified to pH 1.0 with 10% hydrochloric acid. The acidified solution was treated with charcoal and filtered. The filtrate was adjusted to pH 7.0 with 20% aqueous potassium carbonate. The resulting precipitate was collected by filtration, washed successively with water and ethyl acetate, and recrystallized from aqueous ethanol to give 2-(2-amino-4-methyl-5-thiazolyl)imidazo[1,2-a]pyrimidine (0.8 g). mp 285°–286° C. (dec.)

IR (Nujol): 3260, 3080, 1640, 1610, 1580 cm$^{-1}$ NMR (DMSO-d$_6$, δ): 2.38 (3H, s), 7.03 (1H, dd, J=4, 7 Hz), 7.03 (2H, s), 7.77 (1H, s), 8.45 (1H, dd, J=4, 2 Hz), 8.88 (1H, dd, J=7, 2 Hz) Mass. 231 (M+)

EXAMPLE 54

2-(2-Amino-4-methyl-5-thiazolyl)-6-chloroimidazo[1,2-a]pyridine was obtained according to the substantially same manner as that of Example 53. mp 237°–238° C. (dec.) (from aqueous tetrahydrofuran)

IR (Nujol): 3260, 3150, 1625, 1580, 1510 cm$^{-1}$ NMR (DMSO-d$_6$, δ): 2.40 (3H, s), 7.27 (1H, dd, J=2, 10 Hz), 7.62 (1H, d, J=10 Hz), 7.58 (1H, s), 8.75 (1H, d, j=2 Hz) Mass. 264 (M+)

EXAMPLE 55

A solution of ethyl 2-amino-5-(2-bromoacetyl)-4-thiazolecarboxylate (2.93 g) and 2-amino-3-methyl-pyridine (3.24 g) in 1,2-dimethoxyethane (100 ml) was refluxed for 3 hours. The resulting mixture was evaporated in vacuo. To the residue was added water and ethyl acetate, and the resulting mixture was acidified to pH 0.5 with conc. hydrochloric acid. The separated aqueous layer was adjusted to pH 7.0 with 20% aqueous potassium carbonate and extracted with ethyl acetate. The extract was washed with brine, dried over magnesium sulfate, and evaporated in vacuo. The residue was recrystallized from a mixture of ethyl acetate and tetrahydrofuran to give 2-(2-amino-4-ethoxycarbonyl-5-thiazolyl)-8-methylimidazo[1,2-a]pyridine (2.4 g). mp 243°–245° C. (dec.)

IR (Nujol): 3400, 3250, 3100, 1683, 1623, 1530 cm$^{-1}$ NMR (DMSO-d$_6$, δ): 1.33 (3H, t, J=7 Hz), 2.48 (3H, s), 4.33 (2H, q, J=7 Hz), 6.83 (1H, q, J=7 Hz), 7.07 (1H, d, J=7 Hz), 7.35 (2H, s), 8.50 (1H, d, J=7 Hz), 8.68 (1H, s)

EXAMPLE 56

2-(2-Amino-4-ethoxycarbonyl-5-thiazolyl)-6-chloroimidazo[1,2-a]pyridine (1.55 g) was obtained according to substantially the same manner as that of Example 55 from ethyl 2-amino-5-(2-bromoacetyl)-4-thiazolecarboxylate (5.9 g) and 2-amino-5-chloropyridine (7.7 g). mp 277° C. (dec.)

IR (Nujol): 3300, 3240, 3100, 1710, 1620, 1540 cm$^{-1}$ NMR (DMSO-d$_6$, δ): 1.30 (3H, t, J=7 Hz), 4.30 (2H, q, J=7 Hz), 7.28 (1H, d, J=10 Hz), 7.35 (2H, s), 7.58 (1H, d, J=10 Hz), 8.70 (1H, s), 8.90 (1H, s)

EXAMPLE 57

2-(2-Amino-4-ethoxycarbonyl-5-thiazolyl)-7-methylimidazo[1,2-a]pyridine (1.8 g) was obtained according to substantially the same manner as that of Example 55 from ethyl 2-amino-5-(2-bromoacetyl)-4-thiazolecarboxylate (2.94 g) and 2-amino-4-methylpyridine (3.42 g). mp 278°–280° C.

IR (Nujol): 3250, 1710, 1620, 1535 cm$^{-1}$ NMR (DMSO-d$_6$, δ): 1.33 (3H, t, J=7 Hz), 2.33 (3H, s), 4.33 (2H, q, J=7 Hz), 6.73 and (1H, dd, J=2, 8 Hz), 7.33 (3H, br. s), 8.50 (1H, d, J=8 Hz), 8.62 (1H, s)

EXAMPLE 58

2-(2-Amino-4-ethoxycarbonyl-5-thiazolyl)-6-methylimidazo[1,2-a]pyridine (0.83 g) was obtained according to substantially the same manner as that of Example 55 from ethyl 2-amino-5-(2-bromoacetyl)-4-thiazolecarboxylate (2.94 g) and 2-amino-5-methylpyridine (3.24 g). mp 268°–271° C.

IR (Nujol): 3250, 1710, 1620, 1540 cm$^{-1}$ NMR (DMSO-d$_6$, δ): 1.30 (3H, t, J=7 Hz), 2.27 (3H, s), 4.28 (2H, q, J=7 Hz), 7.07 (1H, dd, J=2, 7 Hz), 7.23 (2H, s), 7.43 (1H, d, J=7 Hz), 8.40 (1H, d, J=2 Hz), 8.53 (1H, s)

EXAMPLE 59

2-(2-Amino-4-ethoxycarbonyl-5-thiazolyl)-5-methylimidazo[1,2-a]pyridine (1.0 g) was obtained according to substantially the same manner as that of Example 55 from ethyl 2-amino-5-(2-bromoacetyl)-4-thiazolecarboxylate (2.93 g) and 2-amino-6-methylpyridine (3.24 g). mp 234°–236° C.

IR (Nujol): 3250, 1705, 1620, 1535 cm$^{-1}$ NMR (DMSO-d$_6$, δ): 1.30 (3H, t, J=7 Hz), 2.60 (3H, s), 4.30 (2H, q, J=7 Hz), 6.78 (1H, m), 7.25 (2H, s), 7.03–7.60 (2H, m), 8.42 (1H, s)

EXAMPLE 60

2-(2-Amino-4-ethoxycarbonyl-5-thiazolyl)-3-methylimidazo[1,2-a]pyridine (1.6 g) was obtained according to substantially the same manner as that of Example 55 from ethyl 2-amino-5-(2-bromopropionyl)-4-thiazolecarboxylate (3.7 g) and 2-aminopyridine (3.4 g). mp 180°–182° C.

IR (Nujol): 3250, 3100, 1710, 1630, 1540 cm$^{-1}$ NMR (DMSO-d$_6$+DCl, δ): 1.10 (3H, t, J=7 Hz), 2.62 (3H, s), 4.24 (2H, q, J=7 Hz), 7.63 (1H, m), 8.10 (2H, br. s), 8.88 (1H, d, J=7 Hz)

EXAMPLE 61

2-(2-Amino-4-ethoxycarbonyl-5-thiazolyl)-3,7-dimethylimidazo[1,2-a]pyridine (0.9 g) was obtained according to substantially the same manner as that of Example 55 from ethyl 2-amino-5-(2-bromopropionyl)-4-thiazolecarboxylate (3.7 g) and 2-amino-4-methylpyridine (3.9 g). mp 226°–228° C.

IR (Nujol): 3250, 3100, 1710, 1615 1535 cm$^{-1}$ NMR (DMSO-d$_6$+DCl, δ): 1.15 (3H, t, J=7 Hz), 2.62 (6H, br. s), 4.24 (2H, q, J=7 Hz), 7.54 (1H, dd, J=2, 7 Hz), 7.88 (1H, d, J=2 Hz), 8.78 (1H, d, J=7 Hz)

EXAMPLE 62

2-(2-Amino-4-ethoxycarbonyl-5-thiazolyl)-3-methyl-6-chloroimidazo[1,2-a]pyridine (0.9 g) was obtained according to substantially the same manner as that of Example 55 from ethyl 2-amino-5-(2-bromopropionyl)-4-thiazolecarboxylate (3.2 g) and 2-amino-5-chloropyridine (4.0 g). mp 217°–219° C.

IR (Nujol): 3250, 1715, 1695, 1620, 1535 cm$^{-1}$ NMR (DMSO-d$_6$, δ): 1.13 (3H, t, J=7 Hz), 2.35 (3H, s), 4.17 (2H, q, J=7 Hz), 7.27 (1H, dd, J=2, 9 Hz), 7.37 (2H, s), 7.63 (1H, d, J=9 Hz), 8.57 (1H, d, J=2 Hz)

EXAMPLE 63

A solution of ethyl 5-(2-bromoacetyl)-2-methylamino-4-thiazolecarboxylate (2.5 g) and 2-aminopyridine (2.3 g) in acetonitrile (100 ml) was refluxed for 1.5 hours. The reaction mixture was evaporated in vacuo. To the residue was added water and ethyl acetate and the resulting mixture was acidified to pH 0.8 with 10% hydrochloric acid. The separated aqueous layer was adjusted to pH 7.0 with 20% aqueous potassium carbonate and extracted with a mixture of ethyl acetate and tetrahydrofuran. The organic extract was washed with brine, dried over magnesium sulfate and evaporated in vacuo. The residue was recrystallized from a mixture of ethyl acetate and tetrahydrofuran to give 2-(4-ethoxycarbonyl-2-methylamino-5-thiazolyl)imidazo[1,2-a]pyridine (1.5 g). mp 197°–200° C.

IR (Nujol): 1705, 1580 cm$^{-1}$ NMR (DMSO-d$_6$+DCl, δ): 1.26 (3H, t, J=7 Hz), 3.00 (3H, s), 4.34 (2H, q, J=7 Hz), 7.58 (1H, m), 8.04 (2H, m), 9.08 (1H, d, J=7 Hz)

EXAMPLE 64

2-(4-Ethoxycarbonyl-2-methylamino-5-thiazolyl)-7-methylimidazo[1,2-a]pyridine (2.8 g) was obtained according to substantially the same manner as that of Example 63 from ethyl 5-(2-bromoacetyl)-2-methylamino-4-thiazolecarboxylate (3.9 g) and 2-amino-4-methylpyridine (4.1 g). mp 210°–213° C.

IR (Nujol): 3170, 1705, 1640, 1585 cm$^{-1}$ NMR (DMSO-d$_6$+DCl, δ): 1.26 (3H, t, J=7 Hz), 2.60 (3H, s), 2.98 (3H, s), 4.32 (2H, q, J=7 Hz), 7.42 (1H, dd, J=2, 7 Hz), 7.82 (1H, d, J=2 Hz), 8.92 (1H, d, J=7 Hz)

EXAMPLE 65

A solution of ethyl 2-methylamino-5-(2-bromopropionyl)-4-thiazolecarboxylate (2.2 g) and 5-methyl-2-aminopyridine (2.6 g) in acetonitrile (80 ml) was refluxed for 2 hours. The reaction mixture was evaporated to afford a residue, which was dissolved in a mixture of 5% hydrochloric acid and ethyl acetate. The separated aqueous solution was adjusted to pH 8.0 with 20% potassium carbonate and extracted with ethyl acetate. The extract was washed with brine and dried over magnesium sulfate. The solvent was evaporated in vacuo to afford a crystalline residue, which was recrystallized from a mixture of ethyl acetate and diethyl ether to give 2-(4-ethoxycarbonyl-2-methylaminothiazol-5-yl)-3,6-dimethylimidazo[1,2-a]pyridine (1.3 g).

mp 225°–227° C. IR (Nujol): 3180, 1705, 1570, 1536 cm$^{-1}$ NMR (DMSO-d$_6$, δ): 1.10 (3H, t, J=7 Hz), 2.30 (3H, s), 2.33 (3H, s), 2.87 (3H, d, J=5 Hz), 4.17 (2H, q, J=7 Hz), 7.10 (1H, dd, J=2, 7 Hz), 7.47 (1H, d, J=7 Hz), 7.80 (1H, q, J=5 Hz), 8.08 (1H, d, J=2 Hz)

EXAMPLE 66

2-(4-Ethoxycarbonyl-2-methylaminothiazol-5-yl)-3-methylimidazo[1,2-a]pyridine (1.33 g) was obtained according to substantially the same manner as that of Example 65 from ethyl 5-(2-bromopropionyl)-2-methylamino-4-thiazolecarboxylate (2.28 g) and 2-aminopyridine (2.3 g). mp 183°–185° C.

EXAMPLE 67

2-(4-Ethoxycarbonyl-2-methylaminothiazol-5-yl)-3,7-dimethylimidazo[1,2-a]pyridine (1.3 g) was obtained according to substantially the same manner as that of Example 65 from ethyl 5-(2-bromopropionyl)-2-methylamino-4-thiazolecarboxylate (2.2 g) and 2-amino-4-methylpyridine (2.6 g).

IR (Nujol): 3180, 1710, 1640, 1585 cm$^{-1}$ NMR (DMSO-d$_6$, δ): 1.10 (3H, t, J=7 Hz), 2.30 (3H, s), 2.37 (3H, s), 2.88 (3H, d, J=5 Hz), 4.17 (2H, q, J=7 Hz), 6.78 (1H, dd, J=2, 7 Hz), 7.30 (1H, d, J=2 Hz), 7.77 (1H, q, J=5 Hz), 8.17 (1H, d, J=7 Hz)

EXAMPLE 68

2-[2-(N-Methylformamido)-4-methylthiazol-5-yl]-imidazo[1,2-a]pyridine hydrochloride (2.38 g) was obtained according to substantially the same manner as that of Example 65 from 5-(2-bromoacetyl)-2-(N-methylformamido)-4-methylthiazole (2.77 g) and 2-aminopyridine (2.82 g).

IR (Nujol): 1680, 1640, 1590, 1530 cm$^{-1}$

EXAMPLE 69

2-[2-(N-Methylformamido)-4-methylthiazol-5-yl]-8-methylimidazo[1,2-a]pyridine (1.5 g) was obtained according to substantially the same manner as that of Example 65 from 5-(2-bromoacetyl)-2-(N-methylformamido)-4-methylthiazole (2.77 g) and 2-amino-3-methylpyridine (3.24 g).

EXAMPLE 70

2-[2-(N-Methylformamido)-4-methylthiazol-5-yl]-7-methylimidazo[1,2-a]pyridine (6.5 g) was obtained according to substantially the same manner as that of Example 65 from 5-(2-bromoacetyl)-2-(N-methylformamido)-4-methylthiazole (8.1 g) and 2-amino-4-methylpyridine (9.48 g).

IR (Nujol): 1660, 1680, 1580 cm$^{-1}$ NMR (DMSO-d$_6$, δ): 2.37 (3H, s), 2.53 (3H, s), 3.53 (3H, s), 6.77 (1H, dd, J=2 Hz, 7 Hz), 7.33 (1H, m), 8.1 (1H, s), 8.42 (1H, d, J=7 Hz), 8.72 (1H, s)

EXAMPLE 71

2-[2-(N-Methylformamido)-4-methylthiazol-5-yl]-6-methylimidazo[1,2-a]pyridine (1.10 g) was obtained according to substantially the same manner as that of Example 65 from 5-(2-bromoacetyl)-2-(N-methylformamido)-4-methylthiazole (2.77 g) and 2-amino-5-methylpyridine (3.24 g).

EXAMPLE 72

2-[2-(N-Methylformamido)-4-methylthiazol-5-yl]-6-chloroimidazo[1,2-a]pyridine (8 g) was obtained according to substantially the same manner as that of Example 65 from 5-(2-bromoacetyl)-2-(N-methylformamido)-4-methylthiazole (5.5 g) and 2-amino-5-chloropyridine (7.56 g).

NMR (DMSO-d$_6$, δ): 2.73 (3H, s), 3.97 (3H, s), 8.07 (2H, br.), 8.4 (1H, s), 8.82 (1H, s), 8.88 (1H, s)

EXAMPLE 73

A mixture of 2-(N-methylformamido)-4-methyl-5-(2-bromoacetyl)thiazole (2.3 g), 2-amino-4,5-dihydrothiazole hydrochloride (3.3 g) and triethylamine (5.1 g) in ethanol (100 ml) was refluxed for 10 hours. The reaction mixture was evaporated in vacuo and to the residue was added a mixture of ethyl acetate and 5% hydrochloric acid. The separated aqueous solution was adjusted to pH 7.5 with 20% potassium carbonate and extracted with ethyl acetate. The extract was washed with brine and dried over magnesium sulfate. The solvent was evaporated in vacuo to afford a crystalline residue, which was recrystallized from a mixture of ethyl acetate and diethyl ether to give 2-(2-methylamino-4-methylthiazol-5-yl)imidazo[1,2-a]thiazolidine (0.7 g).

NMR (DMSO-d$_6$, δ): 2.23 (3H, s), 2.82 (3H, s), 3.68–4.4 (4H, m), 7.23 (1H, s)

EXAMPLE 74

2-(2-Methylamino-4-methylthiazol-5-yl)imidazo[1,2-a]pyrimidine (3.0 g) was obtained according to substantially the same manner as that of Example 73 from 5-(2-bromoacetyl)-2-(N-methylformamido)-4-methylthiazole (4.16 g) and 2-aminopyrimidine (4.28 g).

IR (Nujol): 1630, 1525, 1505 cm$^{-1}$ NMR (DMSO-d$_6$, δ): 2.37 (3H, s), 2.82 (3H, d, J=4 Hz), 6.97 (1H, dd, J=4,7 Hz), 7.33–7.53 (1H, m), 7.92 (1H, s), 8.42 (1H, dd, J=2,4 Hz), 8.83 (1H, dd, J=2, 7 Hz)

EXAMPLE 75

A solution of ethyl 2-amino-5-(2-bromoacetyl)-4-thiazolecarboxylate (5.9 g), 2-aminopyrimidine (5.7 g) and triethylamine (8.4 ml) in ethanol (100 ml) was refluxed for 6 hours. The reaction mixture was evaporated in vacuo. To the residue was added a mixture of water and ethyl acetate, and the resulting mixture was acidified to pH 0.5 with conc. hydrochloric acid. The separated aqueous layer was treated with charcoal and filtered. To the filtrate was added ethyl acetate and the resulting mixture was adjusted to pH 7.0 and 20% aqueous potassium carbonate. The precipitate was collected by filtration, washed successively with water, ethyl acetate and ethanol, and dried over phosphorus pentoxide to give 2-(2-amino-4-ethoxycarbonyl-5-thiazolyl)imidazo[1,2-a]pyrimidine (1.6 g). mp 282° C. (dec.)

IR (Nujol): 3300, 3230, 3120, 1710, 1620, 1540 cm$^{-1}$ NMR (DMSO-d$_6$, δ): 1.33 (3H, t, J=7 Hz), 4.32 (2H, q, J=7 Hz), 7.05 (1H, dd, J=4, 7 Hz), 7.36 (2H, s), 8.52 (1H, dd, J=2, 4 Hz), 8.63 (1H, s), 9.05 (1H, dd, J=2, 7 Hz)

EXAMPLE 76

A solution of 5-(2-bromoacetyl-2-hydroxy-4-methylthiazole (3.54 g) and 2-amino-3-methylpyridine (4.9 g) in 1,2-dimethoxyethane (100 ml) was refluxed for 2 hours. The reaction mixture was cooled and the resulting precipitate was collected by filtration.

The filtrate was evaporated in vacuo and the residue was washed with a mixture of diethyl ether and tetrahydrofuran.

The precipitate and residue were suspended in a mixture of water (200 ml) and ethyl acetate (200 ml) and the resulting suspension was acidified to pH 0.7 with 10% hydrochloric acid. The separated ethyl acetate layer was washed with brine, dried over magnesium sulfate, and evaporated in vacuo. The residue was washed with diethyl ether to give 2-(2-hydroxy-4-methyl-5-thiazolyl)-8-methylimidazo[1,2-a]-pyridine (2.48 g). mp 278° C. (dec.) (from ethyl acetate-tetrahydrofuran)

IR (Nujol): 1660 cm$^{-1}$ NMR (DMSO-d$_6$, δ): 3.25 (3H, s), 2.48 (3H, s), 6.66 (1H, dd, J=7, 7 Hz), 7.03 (1H, d, J=7 Hz), 7.96 (1H, s), 8.31 (1H, d, J=7 Hz), 11.21 (1H, br. s) Mass. 245 (M+)

EXAMPLE 77

The following compounds were obtained according to the substantially same manner as that of Example 76.
(1) 2-(2-Hydroxy-4-methyl-5-thiazolyl)imidazo[1,2-a]pyridine. mp 262° C. (dec.) (from tetrahydrofuranethyl acetate)

IR (Nujol): 3150, 1645, 1505 cm$^{-1}$ NMR (DMSO-d$_6$, δ): 2.33 (3H, s), 6.93 (1H, dq, J=2, 7 Hz), 7.30 (1H, dd, J=2, 7 Hz), 7.55 (1H, dd, J=2, 7 Hz), 8.03 (1H, s), 8.50 (1H, dd, J=2, 7 Hz), 11.25 (1H, br. s) Mass. 231 (M+)
(2) 2-(2-Hydorxy-4-methyl-5-thiazolyl)-6-chloroimidazo[1,2-a]pyridine. mp 298° C. (dec.) (from tetrahydrofuran)

IR (Nujol): 1645, 1520 cm$^{-1}$ NMR (DMSO-d$_6$, δ): 2.30 (3H, s), 7.22 (1H, dd, J=2, 9 Hz), 7.55 (1H, d, J=9 Hz), 7.93 (1H, s), 8.68 (1H, d, J=2 Hz), 11.33 (1H, br. s)
(3) 2-(2-Hydroxy-4-methyl-5-thiazolyl)imidazo[1,2-a]pyrimidine. mp<300° C. (from aqueous ethanol)

IR (Nujol): 1650, 1530, 1503 cm$^{-1}$ NMR (DMSO-d$_6$, δ): 2.37 (3H, s), 7.05 (1H, dd, J=4, 7 Hz), 7.97 (1H, s), 8.52 (1H, dd, J=2, 4 Hz), 8.90 (1H, dd, J=7 Hz)

EXAMPLE 78

A solution of ethyl 5-(2-bromoacetyl)-2-hydroxy-4-thiazolecarboxylate (2.94 g) and 2-amino-3-methylpyridine (3.24 g) in 1,2-dimethoxyethane (100 ml) was refluxed for 1.5 hours. The reaction mixture was evaporated in vacuo. To the residue was added a mixture of ethyl acetate and water, and the resulting mixture was acidified to pH 0.8 with 10% hydrochloric acid. The separated aqueous layer was adjusted to pH 7.5 with 20% potassium carbonate and extracted with ethyl acetate. The extract was washed with brine, dried over magnesium sulfate, and evaporated in vacuo. The residue was triturated and diethyl ether and recrystallized from a mixture of ethyl acetate and tetrahydrofuran to give 2-(4-ethoxycarbonyl-2-hydroxy-5-thiazolyl)-8-methylimidazo[1,2-a]pyridine (1.76 g). mp 240°–242° C. (dec.)

IR (Nujol): 3400, 3250, 3100, 1682, 1620, 1530 cm$^{-1}$ NMR (DMSO-d$_6$, δ): 1.30 (3H, t, J=7 Hz), 4.28 (2H, q, J=7 Hz), 6.80 (1H, dd, J=7, 7 Hz), 7.02 (1H, d, J=7 Hz), 7.22 (1H, s), 8.43 (1H, d, J=7 Hz), 8.60 (1H, s)

EXAMPLE 79

2-(4-Ethoxycarbonyl-2-hydroxy-5-thiazolyl)-7-methylimidazo[1,2-a]pyridine was obtained according to the substantially same manner as that of Example 78. mp 258° C. (dec.) (from ethyl acetate-tetrahydrofuran)

IR (Nujol): 3150, 1710, 1680, 1640, 1600, 1530 cm$^{-1}$ NMR (DMSO-d$_6$, δ): 1.33 (3H, t, J=7 Hz), 2.33 (3H, s), 4.33 (2H, q, J=7 Hz), 6.77 (1H, dd, J=2, 7 Hz), 7.30 (1H, d, J=2 Hz), 8.50 (1H, d, J=7 Hz), 8.60 (1H, s), 11.62 (1H, br. s)

EXAMPLE 80

To a suspension of 2-amino-4-methyl-5-acetylthiazole (4.7 g) in 30% solution of hydrogen bromide in acetic acid (50 ml) was added pyridinium hydrobromide perbromide (10.8 g) at ambient temperature and the mixture was stirred at the same temperature for 3 hours. To the reaction mixture was added diisopropyl ether and the solvent was decanted. The residue was added to a solution of 2-aminopyridine (8.5 g) and triethylamine (10 ml) in ethanol (100 ml) and the resulting mixture was refluxed for 5 hours. The reaction mixture was evaporated in vacuo. The residue was suspended in a mixture of water and ethyl acetate and the suspension was acidified to pH 1.0 with 10% hydrochloric acid. The separated aqueous layer was adjusted to pH 7.0 with 20% aqueous potassium carbonate with stirring. The precipitate was collected by filtration, washed successively with water and ethyl acetate. The crude product was recrystallized from a mixture of tetrahydrofuran and water to give 2-(2-amino-4-methyl-5-thiazolyl)imidazo[1,2-a]pyridine (1.4 g). mp 275° C. (dec.)

IR (Nujol): 3420, 3360, 3150, 1630, 1570 cm$^{-1}$ NMR (DMSO-d$_6$, δ): 2.42 (3H, s), 6.83–7.17 (3H, m), 7.73 (1H, s), 8.42 (1H, dd, J=2,5 Hz), 8.83 (1H, dd, J=2, 7 Hz) Mass. 231 (M+1)

EXAMPLE 81

2(2-Amino-4-ethoxycarbonyl-5-thiazolyl)imidazo[1,2-a]pyridine was obtained according to the substantially same manner as that of Example 80. mp 219°–220° C. (dec.) (from ethanol-water)

IR (Nujol): 3250, 3100, 1710, 1618, 1518 cm$^{-1}$ NMR (DMSO-d$_6$, δ): 1.33 (3H, t, J=8 Hz), 4.35 (2H, q, J=8 Hz), 6.73–7.17 (1H, m), 7.32 (1H, d, J=9 Hz), 7.34 (2H, s), 7.55 (1H, d, J=9 Hz), 8.70 (1H, d, J=9 Hz), 8.73 (1H, s) Mass. 288 (M+)

EXAMPLE 82

To a mixture of 2-(2-amino-4-ethoxycarbonyl-5-thiazolyl)imidazo[1,2-a]pyridine (3.0 g) in acetic acid (20 ml) was added pyridinium hydrobromide perbromide (3.5 g) at ambient temperature with stirring, which was continued under the same condition for 30 minutes. The reaction mixture was poured into a mixture of water, ethyl acetate and tetrahydrofuran and the resultant mixture was adjusted to pH 7.5 with 20% potassium carbonate. The separated organic layer was washed with brine and dried over magnesium sulfate. The solvent was removed in vacuo and the residue was recrystallized from a mixture of ethyl acetate and tetrahydrofuran to give 2-(2-amino-4-ethoxycarbonyl-5-thiazolyl)-3-bromo-7-methylimidazo[1,2-a]pyridine (3.0 g). mp 127°–129° C. (dec.)

IR (Nujol): 3350, 3250, 1715, 1610, 1535 cm$^{-1}$ NMR (CF$_3$COOH, δ): 1.48 (3H, t, J=7 Hz), 2.74 (3H, s), 4.64 (2H, q, J=7 Hz), 7.60 (1H, d, J=7 Hz), 7.92 (1H, s), 8.52 (1H, d, J=7 Hz)

EXAMPLE 83

To a solution of 2-(2-methylamino-4-methylthiazol-5-yl)-7-methylimidazo[1,2-a]pyridine (1.92 g) in a mixture of acetic acid (14 ml) and tetrahydrofuran (10 ml) was added pyridinium hydrobromide perbromide (2.6 g) at ambient temperature and the mixture was stirred for an hour. The reaction mixture was poured into water and the resultant aqueous solution was adjusted to pH 7.5 with saturated potassium carbonate. The product was extracted with chloroform and the extract was dried over magnesium sulfate. The solvent was evaporated in vacuo to afford a crystalline residue, which was recrystallized from a mixture of methylene chloride and diethyl ether to give 2-(2-methylamino-4-methylthiazol-5-yl)-3-bromo-7-methylimidazo[1,2-a]-pyridine (2.2 g).

IR (Nujol): 3190, 3110, 1710 cm$^{-1}$ NMR (DMSO-d$_6$, δ) 1.06 (3H, t, J=6 Hz), 2.4 (3H, s), 2.88 (3H, d, J=4 Hz), 4.15 (2H, q, J=7 Hz), 6.95 (1H, dd, J=2 Hz, 7 Hz), 7.38 (1H, m), 7.88 (1H, q, J=4 Hz), 8.21 (1H, d, J=7 Hz)

EXAMPLE 84

To a solution of acetonylacetone (11.4 g) in carbon tetrachloride (50 ml) was dropwise added sulfuryl chloride (27.0 g) at 15° C. to 20° C. with stirring and the mixture was stirred at ambient temperature for one hour. The reaction mixture was evaporated in vacuo below 25° C. and the residue was added to a solution of thiourea (30.0 g) in ethanol (100 ml). After being stirred at ambient temperature for 4 hours, the mixture was evaporated in vacuo. To the residue was added a mixture of ethyl acetate and water and the resulting mixture was acidified to pH 0.8 with 10% hydrochloric acid. The separated aqueous layer was adjusted to pH 8.0 with 20% aqueous potassium carbonate and extracted with ethyl acetate. The extract was washed with brine, dried over magnesium sulfate, and evaporated in vacuo. The residue was washed with diethyl ether to give 2,2'-diamino-4,4'-dimethyl-5,5'-bithiazole (4.43 g). mp 284° C. (dec.)

IR (Nujol): 3400, 3250, 3150, 1620, 1510 cm$^{-1}$ NMR (DMSO-d$_6$, δ): 2.0 (6H, s), 6.90 (4H, s) Mass. 226 (M+)

EXAMPLE 85

2,2'-Dimethylamino-4,4'-dimethyl-5,5'-bithiazole was obtained according to the substantially same manner as that of Example 84. mp>280° C.

IR (Nujol): 3200, 1600, 1520 cm$^{-1}$ NMR (D$_2$O+DCl): 2.25 (6H, s), 3.13 (6H, s)

EXAMPLE 86

A solution of ethyl 2-amino-5-(2-bromoacetyl)-4-thiazolecarboxylate (2.35 g) and thioacetamide (1.8 g) in a mixture of 1,2-dimethoxyethane (70 ml) and ethanol (70 ml) was refluxed for 7 hours and the reaction mixture was evaporated in vacuo. To the residue was added water, and the resulting mixture was adjusted to pH 8.0 with 20% aqueous potassium carbonate and extracted with a mixture of ethyl acetate and tetrahydrofuran. The extract was washed with brine, dried over magnesium sulfate, and evaported in vacuo. The residue was washed with diethyl ether and recrystallized from ethyl acetate to give ethyl 2-amino-5-(2-methyl-4-thiazolyl)-4-thiazolecarboxylate (1.4 g). mp 197°–199° C. (dec.)

IR (Nujol): 3310, 3250, 3060, 1703, 1630, 1540 cm$^{-1}$ NMR (DMSO-d$_6$, δ): 1.28 (3H, t, J=7 Hz), 2.67 (3H, s), 4.28 (2H, q, J=7 Hz), 7.35 (2H, s), 8.10 (1H, s)

EXAMPLE 87

A solution of 5-(2-bromoacetyl)-2-(N-methylformamido)-4-methylthiazole (2.77 g) and N-amidinothiourea (2.37 g) in methanol (30 ml) was stirred for 4 hours at ambient temperature and for 60 minutes under refluxing. The reaction mixture was cooled to 5° C. The resulting precipitate was collected by filtration, washed with cold methanol (5 ml×2) and dried under reduced pressure to give 5-(2-guanidinothiazol-4-yl)-2-(N-methylformamido)-4-methylthiazole (2.76 g).

mp 278° C. (dec.) IR (Nujol): 3300, 1665, 1605, 1510, 1480, 1310, 1270 cm$^{-1}$ NMR (TFA, δ): 2.83 (3H, s), 4.00 (3H, s), 7.50 (1H, s), 7.72 (4H, bs), 8.88 (1H, s) Mass. 296 (M+)

EXAMPLE 88

A mixture of ethyl 2-amino-5-(4-pyridyl)-4-thiazolecarboxylate (5.0 g) and sodium hydroxide (1.6 g) in a mixture of methanol (50 ml) and water (10 ml) was stirred at ambient temperature for an hour. The reaction mixture was evaporated in vacuo and the residue was dissolved in water. The aqueous solution was adjusted to pH 5 with 10% hydrochloric acid. The precipitate was collected by filtration and dried over phosphorus pentoxide in vacuo to afford 2-amino-5-(4-pyridyl)-4-thiazolecarboxylic acid (3.54 g).

mp 211° C. IR (Nujol): 3250, 1630, 1600, 1530, 1500 cm$^{-1}$ NMR (DMSO-d$_6$, δ): 7.26–7.36 (4H, m), 8.46 (2H, dd, J=2, 4 Hz)

EXAMPLE 89

A solution of ethyl 2-methylamino-5-(4-pyridyl)-4-thiazolecarboxylate (2.36 g) in 26% methanolic ammonia (100 ml) was allowed to stand at ambient temperature for 5 days. The reaction mixture was evaporated in vacuo and the residue was washed with tetrahydrofuran to give 4-carbamoyl-2-methylamino-5-(4-pyridyl)-thiazole (1.0 g). mp 212°–213° C. (from tetrahydrofuran-methanol).

IR (Nujol): 3440, 3300, 3110, 1660, 1570 cm$^{-1}$ NMR (DMSO-d$_6$, δ): 2.90 (3H, d, J=4 Hz), 7.48 (2H, dd, J=2, 5 Hz), 7.53 (2H, s), 8.00 (1H, q, J=4 Hz), 8.50 (2H, dd, J=2, 5 Hz) Mass. 234 (M+)

EXAMPLE 90

2-Amino-4-carbamoyl-5-(4-pyridyl)thiazole (0.4 g) was obtained according to substantially the same manner as that of Example 89 from ethyl 2-amino-5-(4-pyridyl)-4-thiazolecarboxylate (2.5 g).

IR (Nujol): 3410, 3270, 3100, 1630, 1660, 1525 cm$^{-1}$ NMR (DMSO-d$_6$, δ): 7.40 (4H, s), 7.45 (2H, dd, J=2, 5 Hz), 8.50 (2H, dd, J=2, 5 Hz)

EXAMPLE 91

A mixture of ethyl 2-methylamino-5-(4-pyridyl)-4-thiazolecarboxylate (2.63 g), 2-aminomethyl-1-ethylpyrrolidine (2.6 g) in a mixture of ethyleneglycol (10 ml) and conc. HCl (0.5 ml) was stirred at 80° C. for 6 hours. The reaction mixture was poured into water and the resultant solution was extracted with ethyl acetate. The organic extract was washed with brine and dried over magnesium sulfate. The solvent was evaporated in vacuo and the residue was subjected to column chromatography on alumina eluting with a mixture of diisopropylether and ethylacetate (1:1) and the fractions containing the desired compound were combined and evaporated in vacuo to give 2-methylamino-5-(4-pyridyl)-4-[(1-ethyl-2-pyrrolidinyl)methylcarbamoyl]thiazole (1.5 g). mp 76°-8° C.

IR (Nujol): 3460, 3330, 3200, 1650, 1575, 1555, 1525, 1500 cm$^{-1}$ NMR (DMSO-d$_6$, δ): 1.05 (3H, t, J=7 Hz), 1.33 (4H, m), 1.9-3.43 (7H, m), 2.90 (3H, d, J=4 Hz), 7.48 (2H, dd, J=2, 4 Hz), 7.95 (2H, m), 8.50 (2H, dd, J=2, 4 Hz)

EXAMPLE 92

To a mixture of 1-piperonylpiperazine (2.72 g) and phosphorous trichloride (0.49 ml) in pyridine (20 ml) was added 2-amino-5-(4-pyridyl)-4-thiazolecarboxylic acid (1.24 g) and the mixture was stirred at 80° C. for 3 hours. The reaction mixture was evaporated in vacuo and the residue was dissolved in a mixture of ethyl acetate and water. The resultant mixture was adjusted to pH 8.0 with saturated aqueous potassium carbonate. The organic extract was dried over magnesium sulfate. The solvent was evaporated in vacuo to give a crystalline residue, which was recrystallized from ethyl acetate to afford 2-amino-5-(4-pyridyl)-4-[(4-piperonyl-1-piperazinyl)carbonyl]thiazole (0.45 g). mp 216°-217° C.

IR (Nujol): 3100, 3300, 1630, 1610 cm$^{-1}$ NMR (DMSO-d$_6$, δ): 3.34 (2H, s), 3.0-3.8 (8H, m), 6.0 (2H, s), 6.6-6.9 (3H, m), 7.2 (2H, dd, J=2, 4 Hz), 7.6 (2H, s), 8.45 (2H, dd, J=2, 4 Hz)

EXAMPLE 93

2-Amino-5-(4-pyridyl)-4-[2-(3,4-dimethoxyphenyl)ethylcarbamoyl]thiazole (0.31 g) was obtained according to substantially the same manner as that of Example 92 from 2-amino-5-(4-pyridyl)-4-thiazole carboxylic acid (1.1 g), phosphorus trichloride (0.44 ml) and 1-(2-aminoethyl)-3,4-dimethoxybenzene (2.0 g). mp 167°-168° C.

IR (Nujol): 3400, 3280, 3100, 1640, 1600 cm$^{-1}$ NMR (DMSO-d$_6$, δ): 2.7 (2H, t, J=7 Hz), 3.42 (2H, m), 3.68 (6H, s), 6.7-6.9 (3H, m), 7.3-7.4 (4H, m), 8.05 (1H, t, J=6 Hz), 8.43 (2H, dd, J=2, 4 Hz)

EXAMPLE 94

To a mixture of 3-[3-(pyrrolidin-1-ylmethyl)phenoxy]propylamine (2.33 g) and phosphorus trichloride (0.44 ml) in pyridine (20 ml) was added 2-amino-5-(4-pyridyl)-4-thiazolecarboxylic acid (1.1 g) and the mixture was stirred at 80° C. for 3 hours. The reaction mixture was evaporated in vacuo and the residue was dissolved in a mixture of ethyl acetate and water. The resultant mixture was adjusted to pH 1.0 with 10% hydrochloric acid. The separated aqueous layer was adjusted to pH 8 with saturated potassium carbonate and extracted with chloroform. The solvent was dried over magnesium sulfate and evaporated in vacuo. The residue was subjected to column chromatography on alumina eluting with a mixture of ethyl acetate and tetrahydrofuran (3:7). The fractions containing the desired compound were combined and evaporated in vacuo. To the oily residue was added a solution of ethyl acetate and hydrochloric acid. The precipitate was collected by filtration and dried over phosphorus pentoxide in vacuo to afford 2-amino-5-(4-pyridyl)-4-[3-[3-(pyrrolidin-1-yl-methyl)phenoxy]propylcarbamoyl]thiazole hydrochloride (0.34 g).

IR (Nujol): 3400, 2600, 1630 cm$^{-1}$ NMR (DMSO-d$_6$, δ): 1.8-2.25 (6H, m), 3.0-3.8 (1H, m), 4.0-4.4 (2H, m), 4.33 (2H, s), 6.9-7.2 (3H, m), 7.3-7.6 (1H, m), 7.95 (2H, d, J=6 Hz), 8.6 (2H, d, J=6 Hz)

EXAMPLE 95

Trifluoroacetic acid (2.8 g) was dropwise added to a suspension of 2-methylamino-4-carbamoyl-5-(4-pyridyl)thiazole (2.1 g) and pyridine (2.8 g) in methylene chloride (60 ml) at 5° to 10° C. with stirring, which was continued under the same condition for 6 hours. The reaction mixture was poured into ice-water and the resultant mixture was acidified to pH 1.0 with 10% hydrochloric acid. The separated aqueous layer was adjusted to pH 7.5 with 20% potassium carbonate and extracted with ethyl acetate. The organic extract was washed with brine and dried over magnesium sulfate. The solvent was removed in vacuo to give a crystalline residue, which was recrystallized from a mixture of ethyl acetate and tetrahydrofuran to afford 4-cyano-2-methylamino-5-(4-pyridyl)thiazole (0.5 g). mp 192°-195° C.

IR (Nujol): 3220, 2220, 1623, 1598, 1540 cm$^{-1}$ NMR (DMSO-d$_6$): 2.9 (3H, d, J=5 Hz), 7.56 (2H, dd, J=2, 5 Hz), 8.45 (1H, m), 8.65 (2H, dd, J=2, 5 Hz) Mass. 216 (M+)

EXAMPLE 96

To a solution of ethyl 2-methylamino-5-(4-pyridyl)-4-thiazolecarboxylate (2.6 g) in dry tetrahydrofuran (120 ml) was added lithium aluminum hydride (0.38 g) at −10° C. with stirring, which was continued at −10~−3° C. for 30 minutes. The reaction mixture was poured into ice-water and the resultant solution was acidified to pH 1.0 with 10% hydrochloric acid. The insoluble material was filtered off. The filtrate was adjusted to pH 7.0 with 20% aqueous solution of potassium carbonate and extracted with a mixture of ethyl acetate and tetrahydrofuran. The organic extract was concentrated in vacuo. The precipitate was collected by filtration, washed with ethyl acetate and dried in vacuo to give 4-formyl-2-methylamino-5-(4-pyridyl)thiazole (0.8 g). mp 243°-245° C. (dec.)

IR (Nujol): 1675, 1620, 1595 cm$^{-1}$ Mass. 219 (M+)

EXAMPLE 97

2-Amino-4-formyl-5-(4-pyridyl)thiazole (1.6 g) was obtained according to substantially the same manner as that of Example 96 from ethyl 2-amino-5-(4-pyridyl)-4-thiazolecarboxylate (2.5 g).

IR (Nujol): 1670, 1590 cm$^{-1}$ NMR (DMSO-d$_6$, δ): 7.45 (2H, dd, J=2, 4 Hz), 7.60 (2H, s), 8.67 (2H, dd, J=2, 4 Hz), 9.73 (1H, s)

EXAMPLE 98

To a solution of ethyl 2-hydroxy-5-(4-pyridyl)-4-thiazolecarboxylate (2.9 g) in dry tetrahydrofuran (100 ml) was added lithium aluminum hydride (0.43 g) at 20° C. with stirring, which was continued at ambient temperature for an hour. The reaction mixture was poured into ice-water and the resultant aqueous solution was adjusted to pH 1.0 with 10% hydrochloric acid. After filtration of an insoluble material, the filtrate was adjusted to pH 7.0 with 20% potassium carbonate and extracted with a mixture of ethyl acetate and tetrahydrofuran. The organic extract was washed with brine, dried over magnesium sulfate and evaporated in vacuo to give a mixture of 2-hydroxy-4-hydroxymethyl-5-(4-pyridyl)thiazole and 4-formyl-2-hydroxy-5-(4-pyridyl)-thiazole, which was dissolved in a mixture of methanol (60 ml) and tetrahydrofuran (10 ml). To the solution was portionwise added sodium borohydride (0.1 g) at ambient temperature with stirring, which was continued under the same condition for an hour. The reaction mixture was evaporated in vacuo and the residue was dissolved in a mixture of ethyl acetate and tetrahydrofuran. The organic layer was washed with brine, dried over magnesium sulfate and evaporated in vacuo to afford 2-hydroxy-4-hydroxymethyl-5-(4-pyridyl)-thiazole (0.35 g).

mp 222°–223° C. (dec.) IR (Nujol): 3320, 1630, 1590, 1570 cm$^{-1}$ NMR (DMSO-d$_6$, δ): 4.40 (2H, s), 5.6 (1H, m), 7.40 (2H, dd, J=2, 5 Hz), 8.61 (2H, dd, J=2, 5 Hz) Mass. 208 (M$^+$)

EXAMPLE 99

4-Hydroxymethyl-2-methylamino-5-(4-pyridyl)-thiazole (0.9 g) was obtained according to substantially the same manner as that of Example 98 from ethyl 2-methylamino-5-(4-pyridyl)-4-thiazolecarboxylate (2.1 g). mp: 216°–218° C. (from tetrahydrofuran)

IR (Nujol): 3100, 1575 cm$^{-1}$ NMR (DMSO-d$_6$, δ): 2.87 (3H, d, J=4 Hz), 4.38 (2H, d, J=4 Hz), 5.33 (1H, t, J=4 Hz), 7.40 (2H, dd, J=2, 5 Hz), 7.83 (1H, q, J=4 Hz), 8.53 (2H, dd, J=2, 5 Hz) Mass. 221 (M$^+$)

EXAMPLE 100

A mixture of 2-methylamino-4-formyl-5-(4-pyridyl)-thiazole (1.1 g) and triphenylphosphinecarbomethoxymethylene (3.34 g) in tetrahydrofuran (80 ml) was stirred at 40° to 45° C. for 2.5 hours. The reaction mixture was poured into water and the resultant solution was acidified to pH 1.0 with 10% hydrochloric acid. The acidified solution was washed with ethyl acetate. The aqueous solution was adjusted to pH 7.0 with 20% aqueous potassium carbonate and extracted with ethyl acetate. The organic extract was washed with brine and dried over magnesium sulfate. The solvent was evaporated in vacuo and the residue was subjected to column chromatography on silica gel eluting with a mixture of ethyl acetate and tetrahydrofuran (8:2). The fractions containing the desired compound were combined and evaporated in vacuo to give methyl 2-methylamino-5-(4-pyridyl)-4-thiazoleacrylate (trans isomer) (0.66 g). mp 166°–167° C.

IR (Nujol): 3200, 3120, 1710, 1608, 1590, 1510 cm$^{-1}$ NMR (DMSO-d$_6$, δ): 2.93 (3H, d, J=5 Hz), 3.72 (3H, s), 6.6 (1H, d, J=17 Hz), 7.35 (2H, dd, J=2, 4 Hz), 7.43 (1H, d, J=17 Hz), 8.02 (1H, q, J=5 Hz), 8.63 (2H, dd, J=2, 4 Hz) Mass. 275 (M$^+$)

EXAMPLE 101

2-Amino-4-(2-cyanovinyl)-5-(4-pyridyl)thiazole (0.26 g) was obtained according to substantially the same manner as that of Example 100 from 2-amino-4-formyl-5-(4-pyridyl)thiazole (1.5 g). mp 290°–291° C. (dec.)

IR (Nujol): 3350, 3300, 3120, 2200, 1620, 1600, 1530 cm$^{-1}$ NMR (DMSO-d$_6$, δ): 6.2 (1H, d, J=16 Hz), 7.38 (2H, dd, J=2, 4 Hz), 7.42 (1H, d, J=16 Hz), 7.56 (2H, s), 8.60 (2H, dd, J=2, 4 Hz)

EXAMPLE 102

To a solution of 2-methylamino-4-formyl-5-(4-pyridyl)thiazole (1.1 g) in a mixture of tetrahydrofuran (40 ml) and water (40 ml) was added triphenyl (4-pyridylmethyl)phosphonium iodide hydrochloride (7.8 g). The resultant mixture was stirred at ambient temperature for 3 hours, during which time the mixture was maintained at pH 9.5 to 10 with 20% aqueous potassium carbonate. The reaction mixture was adjusted to pH 1.0 with 10% hydrochloric acid and washed with ethyl acetate. The aqueous solution was adjusted to pH 7.0 with 20% aqueous potassium carbonate and extracted with a mixture of ethyl acetate and tetrahydrofuran. The organic extract was dried over magnesium sulfate and evaporated in vacuo. The residue was subjected to column chromatography on silica gel eluting with a mixture of ethyl acetate and tetrahydrofuran (4:1). The fractions containing the desired compound were combined and evaporated in vacuo to give 2-methylamino-4-[2-(4-pyridyl)vinyl]-5-(4-pyridyl)thiazole (0.16 g).

mp 241° C. (dec.) IR (Nujol): 3210, 1590, 1550, 1510 cm$^{-1}$ NMR (DMSO-d$_6$, δ): 2.95 (3H, d, J=4 Hz), 7.33 (2H, s), 7.38 (2H, dd, J=2, 4 Hz), 7.50 (2H, dd, J=2,4 Hz), 7.92 (1H, q, J=4 Hz), 8.50 (2H, dd, J=2, 4 Hz), 8.57 (2H, dd, J=2, 4 Hz) Mass. 294 (M$^+$)

EXAMPLE 103

Potassium tert-butoxide (1.46 g) was added to a solution of 2-methylamino-5-(4-pyridyl)-4-thiazolecarbaldehyde (1.9 g) and methyltriphenylphosphonium bromide (4.66 g) in dimethyl sulfoxide (87 ml) and the mixture was stirred for 5 hours at ambient temperature. The reaction mixture was poured into ice-water (300 ml) and extracted with ethyl acetate (100 ml×2). The extract was washed with a saturated aqueous solution of sodium chloride (100 ml) and dried over magnesium sulfate. Solvent was distilled off and the residue was subjected to column chromatography on silica gel (120 g) and eluted with a mixture of chloroform and methanol (40:1). The fractions containing the object compound were combined and concentrated until the volume was about 15 ml. The resultant white needles were collected by filtration and washed with cold ethyl acetate and dried under reduced pressure to give white needles of 2-methylamino-5-(4-pyrridyl)-4-vinylthiazole (510 mg).

mp 110°–111° C. IR (Nujol): 3200, 3100, 1580, 1530, 1508, 1405, 1330, 1310, 1210 cm$^{-1}$ NMR (CDCl$_3$, δ): 3.01 (3H, s), 5.36 (1H, d d., J=10 Hz), 6.03 (1H, dd, J=3 Hz, 17 Hz), 6.76 (1H, dd, J=10 Hz), 17 Hz), 6.67 (1H, bs), 7.26 (2H, dd, J=2 Hz, 5 Hz), 8.58 (2H, d d, J=2 Hz, 5 Hz) Mass. 217 (M+)

EXAMPLE 104

A solution of 4-formyl-2-methylamino-5-(4-pyridyl)-thiazole (0.9 g) in methanol (15 ml) was added to a 1N-methanolic hydroxylamine solution (5.8 ml) at ambient temperature with stirring, which was continued under the same condition for 2 hours. The precipitate was collected by filtration and recrystallized from an aqueous tetrahydrofuran to afford 4-hydroxyiminomethyl-2-methylamino-5-(4-pyridyl)thiazole (1.02 g).

mp 266°–267° C. (dec.) TR (Nujol): 3160, 3100, 1590, 1525 cm$^{-1}$ NMR (DMSO-d$_6$, δ): 2.92 (3H, d, J=5 Hz), 7.33 (2H, dd, J=2, 5 Hz), 7.88 (1H, m), 7.98 (1H, s), 8.52 (2H, dd, J=2, 5 Hz), 11.39 (1H, s) Mass. 234 (M+)

EXAMPLE 105

A solution of thionylchloride (1.06 g) in chloroform (5 ml) was dropwise added to a solution of 2-methylamino-4-hydroxymethyl-5-(4-pyridyl)thiazole (1.0 g) in chloroform (20 ml) at ambient temperature for a period of 5 minutes with stirring, which was continued under the same condition for 90 minutes and at 50° C. for 30 minutes. The reaction mixture was evaporated in vacuo and the residue was dissolved in a mixture of water (50 ml) and ethyl acetate (30 ml). The solution was adjusted to pH 6.5 with 30% aqueous potassium carbonate and extracted with ethyl acetate. The extract was washed with a saturated aqueous solution of sodium chloride and dried over magnesium sulfate. The solvent was distilled off to give yellow powder of 2-methylamino-4-chloromethyl-5-(4-pyrridyl)thiazole (0.9 g).

mp 231°–236° C. (dec.) IR (Nujol): 3200, 3110, 1610, 1590, 1406, 1330, 1310 cm$^{-1}$ NMR (DMSO-d$_6$, δ): 2.88 (3H, d, J=4 Hz), 4.68 (2H, s), 7.40 (2H, d d, J=2 Hz, 5 Hz), 8.02 (1H, d, J=4 Hz), 8.59 (2H, d d, J=2 Hz, 5 Hz)

EXAMPLE 106

To a solution of 4-chloromethyl-3-methylamino-5-(4-pyridyl)thiazole (1.92 g) in tetrahydrofuran (80 ml) were added 30% methanol solution of methanethiol (4 ml) and sodium methanethiolate (710 mg). The mixture was stirred at ambient temperature for 15 minutes. The reaction mixture was evaporated under reduced pressure to give a residue, which was dissolved in 1N-hydrochloric acid (50 ml). The solution was adjusted to pH 7 with 20% aqueous potassium carbonate and extracted with ethyl acetate (100 ml). The extract was washed with a saturated aqueous solution of sodium chloride and dried over magnesium sulfate. Solvent was distilled off and the residue was subjected to column chromatography on silica gel (170 g) and eluted with a mixture of chloroform and methanol (30:1). The fractions containing the object compound were combined and concentrated under reduced pressure to give yellow powder of 2-methylamino-4-methylthiomethyl-5-(4-pyridyl)thiazole (1.5 g).

mp 135°–138° C. IR (Nujol): 3200, 3100, 1630, 1585, 1550, 1540, 1530, 1400, 1330, 1310, 1215 cm$^{-1}$ NMR (DMSO-d$_6$, δ): 2.16 (3H, s), 2.86 (3H, d, J=5 Hz), 3.73 (2H, s), 7.34 (2H, d d., J=2 Hz, 5 Hz), 7.86 (1H, d, J=5 Hz), 8.53 (2H, d d., J=2 Hz, 5 Hz)

EXAMPLE 107

To a mixture of 4-methyl-2-tritylamino-5-thiazolecarboxylic acid (7.2 g) and 2-(3,4-dimethoxyphenyl)ethylamine (3.26 g) in N,N-dimethylformamide (100 ml) were added 1-hydroxybenzotriazole (2.92 g) and dicyclohexylcarbodiimide (4.45 g) and the mixture was stirred at ambient temperature for 1 hour. After filteration, the filtrate was evaporated under reduced pressure. The residue was dissolved in chloroform-methanol (9:1 v/v, 20 ml), removed undissolved materials by filtration, and the filtrate was subjected to column chromatography on silica gel to give N-[2-(3,4-dimethoxyphenyl)ethyl]-4-methyl-2-tritylamino-5-thiazolecarboxamide (8.65 g).

A mixture of N-[2-(3,4-dimethoxyphenyl)ethyl]-4-methyl-2-tritylamino-5-thiazolecarboxamide (5.0 g) and polyphospholic acid (116% as H$_3$PO$_4$, 50 g) was stirred at 100° C. for 10 hours. After the reaction mixture was cooled, water (250 ml) was added and stirred for 1 hour. After removal of insoluble materials by filtration, the filtrate was neutralized with sodium carbonate. From the aqueous solution was extracted the desired compound with chloroform, and the extract was dried over magnesium sulfate. The solvent was evaporated under reduced pressure, and the residue was triturated in diisopropyl ether to afford 1-(2-amino-4-methylthiazol-5-yl)-6,7-dimethoxy-3,4-dihydroisoquinoline (0.67 g).

mp 233°–237° C. IR (Nujol): 1640, 1595 cm$^{-1}$ NMR (DMSO-d$_6$, δ): 7.06 (2H, br s), 6.95 (2H, s), 3.84 (3H, s), 3.73 (3H, s), 3.2–3.7 (2H, m), 2.5–2.9 (2H, m), 2.00 (3H, s)

EXAMPLE 108

1-(2-Methylamino-4-methylthiazol-5-yl)-6,7-dimethoxy-3,4-dihydroisoquinoline was obtained according to substantially the same manner as that of Example 107.

NMR (DMSO-d$_6$, δ): 7.6 (1H, br. d, J=4 Hz), 6.96 (2H, s), 3.85 (3H, s), 3.73 (3H, s), 3.4–3.8 (2H, m), 2.8 (3H, br d, J=4 Hz), 2.3–2.8 (2H, m), 2.04 (3H, s)

EXAMPLE 109

1-(2-Hydroxy-4-methylthiazol-5-yl)-6,7-dimethoxy-3,4-dihydroisoquinoline was obtained according to substantially the same manner as that of Example 107.

mp 114°–120° C. IR (Nujol): 1680, 1600 cm$^{-1}$ NMR (DMSO-d$_6$, δ): 6.98 (2H, d, J=2 Hz), 3.86 (3H, s), 3.76 (3H, s), 3.4–3.8 (2H, m), 2.6–2.8 (2H, m), 1.98 (3H, s)

EXAMPLE 110

To a suspension of 2-amino-4-methyl-5-(4-pyridyl)thiazole (3.84 g) in methylene chloride (600 ml) was added triethylamine (40 ml). To the resultant mixture was dropwise added a solution of acetyl chloride (3.77 g) in methylene chloride (100 ml) at 15°–20° C. and stirred at the same temperature for an hour. The reaction mixture was evaporated to dryness in vacuo and water (100 ml) was added thereto. The resulting mixture was adjusted to pH 3.0 with 10% hydrochloric acid and stirred for 10 minutes. The mixture was adjusted to pH 6.5 with a saturated aqueous solution of sodium bicarbonate. The resulting aqueous mixture was allowed to stand for 2 hours at 5° C. The precipitate was collected, washed with water (20 ml×2) and dried over phosphorus pentoxide in vacuo to give a yellow powder (3.4 g).

The powder (1.5 g) obtained above was recrystallized from ethyl acetate to afford 2-acetylamino-4-methyl-5-(4-pyridyl)thiazole (1.1 g). mp 213°–216° C. (dec.)

IR (Nujol): 3140, 1650, 1590, 1550, 1525, 1300, 1290, 1003, 815 cm$^{-1}$ NMR (D$_2$O+DCl, δ): 2.47 (3H, s), 2.30 (3H, s), 7.8–8.0 (2H, m), 8.6–8.8 (2H, m)

EXAMPLE 111

To a solution of 2-methylamino-4-methyl-5-acetylthiazole (35 g) in tetrahydrofuran (700 ml) were added a mixture of acetic anhydride (94.5 ml) and formic acid (37.7 ml) at ambient temperature and the mixture was stirred for two hours. The reaction mixture was evaporated in vacuo. The residue was added to water and the resultant precipitate was collected by filtration and dried over phosphorus pentoxide to give 2-(N-methylformamido)-4-methyl-5-acetylthiazole (39.59 g).

mp 152°–153° C.

NMR (DMSO-d$_6$, δ): 2.48 (3H, s), 2.56 (3H, s), 3.52 (3H, s), 8.78 (1H, s)

EXAMPLE 112

To a solution of 2-[2-(N-methylformamido)-4-methylthiazol-5-yl]-7-methylimidazo[1,2-a]pyridine (4.87 g) in ethanol (200 ml) was added 36% hydrochloric acid (2.6 ml) and refluxed for 1.5 hours. The reaction mixture was evaporated. The residue was dissolved in water, and the aqueous mixture was adjusted to pH 8 with saturated potassium carbonate. Extraction with chloroform, and evaporation afforded 2-(2-methylamino-4-methylthiazol-5-yl)-7-methyl-imidazo[1,2-a]pyridine (3.22 g). mp 220°–221° C.

IR (Nujol): 1580 cm$^{-1}$ NMR (DMSO-d$_6$, δ): 2.36 (6H, s), 2.85 (3H, d), 6.72 (1H, dd, J=2,7 Hz), 7.1–7.57 (2H, m), 7.87 (1H, s), 8.37 (1H, d, J=7 Hz)

EXAMPLE 113

2-(2-Methylamino-4-methylthiazol-5-yl)imidazo[1,2-a]pyridine (1.4 g) was obtained according to substantially the same manner as that of Example 112 from 2-[2-(N-methylformamido)-4-methylthiazol-5-yl]-imidazo[1,2-a]pyridine hydrochloride (2.38 g). mp 228°–229° C.

IR (Nujol): 1580 cm$^{-1}$ NMR (CF$_3$COOH, δ): 2.2 (3H, s), 3.3 (3H, br), 7.48–8.17 (1H, m), 7.97–8.23 (2H, m), 8.28 (1H, s), 8.33–8.6 (1H, m), 8.67 (1H, d, J=7 Hz)

EXAMPLE 114

2-(2-Methylamino-4-methylthiazol-5-yl)-8-methylimidazo[1,2-a]pyridine hydrochloride (0.87 g) was obtained according to substantially the same manner as that of Example 112 from 2-[2-(N-methylformamido)-4-methylthiazol-5-yl]-8 methylimidazo[1,2-a]pyridine (1.5 g). mp 255°–260° C.

EXAMPLE 115

2-(2-Methylamino-4-methylthiazol-5-yl)-6-methylimidazo[1,2-a]pyridine hydrochloride (0.93 g) was obtained according to substantially the same manner as that of Example 112 from 2-[2-(N-methylformamido)-4-methylthiazol-5-yl]-6-methylimidazo[1,2-a]pyridine (1.1 g). mp 270°–273° C.

EXAMPLE 116

2-(2-Methylamino-4-methylthiazol-5-yl)-6-chloroimidazo[1,2-a]pyridine was obtained according to substantially the same manner as that of Example 112. mp 242°–243° C.

IR (Nujol): 1600, 1575 cm$^{-1}$ NMR (DMSO-d$_6$, δ): 2.37 (3H, s), 2.85 (3H, d, J=4 Hz), 7.3 (1H, d, J=2 Hz), 7.42–7.65 (2H, m), 7.96 (1H, s), 8.72 (1H, d, J=2 Hz)

EXAMPLE 117

A solution of 5-(2-guanidinothiazol-4-yl)-2-(N-methylformamido)-4-methylthiazole (1.5 g) in a mixture of methanol (25 ml) and 10% hydrochloric acid was stirred for 2 hours under refluxing. After addition of water (100 ml), the reaction mixture was adjusted to pH 7.0 with 20% aqueous potassium carbonate. The resulting precipitate was collected by filtration, washed with water (10 ml×2) and methanol (15 ml×2) successively and dried over phosphorus pentoxide under reduced pressure to give 5-(2-guanidinothiazol-4-yl)-4-methyl-2-methylaminothiazole (1.05 g).

mp 283°–286° C. (dec.) IR (Nujol): 3350, 3300, 3200, 3150, 1660, 1630, 1590, 1580, 1520, 1330 cm$^{-1}$ NMR (D$_2$O+DCl, δ): 2.30 (3H, s), 3.08 (3H, s), 7.08 (1H, s) Mass. 268 (M$^+$)

EXAMPLE 118

A solution of 2-amino-4-methyl-5-(3-pyridyl)thiazole (2.97 g) and isoamylnitrite (2.28 g) in tetrahydrofuran (80 ml) was refluxed for one hour with stirring. To the reaction mixture was added ethyl acetate (200 ml), and the resulting mixture was washed with brine. The separated organic layer was dried over magnesium sulfate and evaporated in vacuo. The residue was subjected to column chromatography on silica gel and eluted with a mixture of diisopropyl ether and ethyl acetate (3:7). The fractions containing the desired compound were combined and evaporated in vacuo. The oily residue was dissolved in a solution of methanolic hydrogen chloride and evaporated in vacuo. The residue was crystallized from a mixture of methanol and tetrahydrofuran to give 4-methyl-5-(3-pyridyl)thiazole hydrochloride (1.15 g). mp 225° C. (dec.)

IR (Nujol): 2700–1800, 1590, 1560 cm$^{-1}$ NMR (DMSO-d$_6$, δ): 2.53 (3H, s), 8.15 (1H, dd, J=5, 8 Hz), 8.75 (1H, dd, J=2, 8 Hz), 8.95 (1H, dd, J=2, 5 Hz), 9.12 (1H, d, J=2 Hz), 9.33 (1H, s)

EXAMPLE 119

To a solution of 5-acetyl-2-amino-4-methylthiazole (15.6 g) in a mixture of tetrahydrofuran (200 ml) and dimethylformamide (50 ml) was dropwise added isoamylnitrite (14.6 g) at 50° C. to 55° C. with stirring and the mixture was stirred at 55° C. to 60° C. for 4 hours. The reaction mixture was poured into a mixture of ethyl acetate and water with stirring. The separated organic layer was washed with brine, dried over magnesium sulfate, and evaporated in vacuo. The residue was subjected to column chromatography on silica gel and eluted with a mixture of diisopropyl ether and ethyl acetate (1:1). The fractions containing the desired compound were combined and evaporated in vacuo to give 5-acetyl-4-methylthiazole (7.7 g) as an oil.

IR (Film): 1660 cm$^{-1}$ NMR (DMSO-d$_6$, δ): 2.56 (3H, s), 2.68 (3H, s), 9.16 (1H, s)

EXAMPLE 120

Ethyl 5-(4-pyridyl)-4-thiazolecarboxylate hydrochloride (1.4 g) was obtained according to substantially the same manner as that of Example 119 from Ethyl 2-amino-5-(4-pyridyl)-4-thiazolecarboxylate (3.3 g) and isoamylnitrite (2.3 ml). mp 209°–210° C.

IR (Nujol): 1720, 1630, 1605 cm$^{-1}$ NMR (DMSO-d$_6$, δ): 1.18(3H, t), 4.24(2H, q), 8.16 (2H, dd, J=2, 6 Hz), 8.96(2H, dd, J=2, 6 Hz)

EXAMPLE 121

2-Amino-4-ethyl-5-(4-pyridyl)thiazole (0.77 g) was obtained according to substantially the same manner as that of Example 6 from 1-(4-pyridyl)butan-2-one (1.5 g) and thiourea (0.91 g). mp 209°–211° C.

IR (Nujol): 3250, 3060, 1650, 1590, 1555, 1525, 1470, 1330, 1305, 995 cm$^{-1}$

NMR (D$_2$O+DCl, δ): 1.37(3H, t, J=7 Hz), 2.97(2H, q, J=7 Hz), 8.0–8.3(2H, m), 8.7–9.0(2H, m) Mass. 205 (M+)

EXAMPLE 122

4-Ethyl-2-hydroxy-5-(4-pyridyl)thiazole (1.35 g) was obtained according to substantially the same manner as that of Example 34 from 1-(4-pyridyl)butan-2-one (5.96 g) and ethyl thiocarbamate (8.41 g). mp 234°–235.5° C. (dec.)

IR (Nujol): 3150, 3050, 1670, 1595, 1500, 1000, 820 cm$^{-1}$ NMR (D$_2$O+DCl, δ): 1.38(3H, t, J=7 Hz), 2.90(2H, q, J=7 Hz), 7.96(2H, dd, J=2, 8 Hz), 8.84(2H, dd, J=2, 8 Hz) Mass. 206 (M+)

EXAMPLE 123

To a suspension of 2,2'-dimethylamino-4,4'-dimethyl-5,5'-bithiazole (1.9 g) in ethanol (100 ml) was added conc. hydrochloric acid (2 ml) and the resulting solution was evaporated in vacuo. The residue was dissolved in ethanol (100 ml) and the solution was concentrated in vacuo. The resulting precipitate was collected by filtration and washed with diethyl ether to give 2,2'-dimethylamino-4,4'-dimethyl-5,5'-bithiazole dihydrochloride (1.86 g). mp 277° C. (dec.)

IR (Nujol): 3160, 1640, 1530 cm$^{-1}$ NMR (D$_2$O, δ): 2.22 (6H, s), 3.1 (6H, s)

EXAMPLE 124

2-Guanidino-4-methyl-5-(4-methylpyridin-2-yl)thiazole (0.42 g) was obtained according to substantially the same manner as that of Example 11 from 1-(4-methylpyridin-2-yl)acetone (3.0 g) and N-amidinothiourea (2.36 g).

mp 230°–232° C. (dec.) IR (Nujol): 3300, 3120, 1690, 1610, 1595, 1550, 1495, 1220 cm$^{-1}$ NMR (D$_2$O+DCl, δ): 2.50(3H, s), 2.72(3H, s), 7.83 (1H, dd, J=2, 6 Hz), 7.96(1H, d, J=2 Hz), 8.65 (1H, d, J=6 Hz). Mass. 247 (M+)

EXAMPLE 125

2-Guanidino-4-methyl-5-(6-methylpyridin-2-yl)thiazole (0.58 g) was obtained according to substantially the same manner as that of Example 11 from 1-(6-methylpyridin-2-yl)acetone (4.5 g) and N-amidinothiourea (4.8 g).

mp 271°–273° C. (dec.) IR (Nujol): 3400, 3300, 3200, 1690, 1630, 1610, 1570, 1490, 1225 cm$^{-1}$ NMR (D$_2$O+DCl, δ): 2.48 (3H, s), 2.90(3H, s), 7.8–8.1(2H, m), 8.48(1H, d, J=8 Hz), 8.62 (1H, d, J=8 Hz) Mass. 247 (M+)

EXAMPLE 126

2-Amino-4-methyl-5-(4-methylpyridin-2-yl)thiazole (1.9 g) was obtained according to substantially the same manner as that of Example 11 from 1-(4-methylpyridin-2-yl)acetone (1.5 g) and thiourea (1.5 g).

mp 300°–305° C. (dec.) IR (Nujol): 3200, 3130, 2780, 1630, 1598, 1580 cm$^{-1}$ NMR (D$_2$O+DCl, δ): 2.35(3H, s), 2.73(3H, s), 7.98 (1H, dd, J=2, 6 Hz), 8.02(1H, bs), 8.72(1H, d, J=6 Hz) Mass. 205 (M+)

EXAMPLE 127

2-Amino-4-methyl-5-(6-methylpyridin-2-yl)thiazole (1.61 g) was obtained according to substantially the same manner as that of Example 11 from 1-(6-methylpyridin-2-yl)acetone (1.5 g) and thiourea (1.52 g).

mp 277°–280° C. (dec.) IR (Nujol): 3280, 3150, 1635, 1590, 1575, 1570, 1255 cm$^{-1}$ NMR (D$_2$O+DCl, δ): 2.38(3H, s), 2.80(3H, s), 7.92 (2H, d, J=8 Hz), 8.49(1H, d, J=8 Hz), 8.60(1H, d, J=8 Hz) Mass. 205 (M+)

EXAMPLE 128

To a solution of N,N-dimethylethylenediamine (0.59 ml) in pyridine (10 ml) were added phosphorus trichloride (1.3 g) and 2-amino-5-(4-pyridyl)-4-thiazolecarboxylic acid (1.5 g) and the mixture was stirred at 100° C. for 5 hours. The reaction mixture was poured into water (50 ml), adjusted to pH 8 with aqueous potassium carbonate and extracted with a mixture of chloroform and tetrahydrofuran. The extract was dried over magnesium sulfate and evaporated in vacuo to give 2-amino-4-[N-[2-(N,N-dimethylamino)ethyl]carbamoyl]-5-(4-pyridyl)thiazole (0.4 g).

IR (Nujol): 3360, 1650, 1600 cm$^{-1}$ NMR (D$_2$O+DCl, δ): 2.99(6H, s), 3.44(2H, t), 3.77 2H, t), 7.88(2H, dd), 8.7(2H, dd)

EXAMPLE 129

To a solution of ethyl 2-amino-5-(2-pyridyl)-4-thiazolecarboxylate (2.49 g) in ethyleneglycol (10 ml) were added N,N-dimethylethylenediamine (1.76 g) and 36% hydrochloric acid (0.5 ml) and the mixture was stirred at 80° C. for 2 hours. The reaction mixture was poured into water (50 ml), adjusted to pH 8 with aqueous potassium carbonate and extracted with chloroform. The extract was washed with brine, dried over magnesium sulfate and evaporated in vacuo. The residue was recrystallized from acetonitrile to give 2-amino-4-[N-[2-(N,N-dimethylamino)ethyl]carbamoyl]-5-(2-pyridyl)thiazole (2.0 g).

mp 143°–144° C.

IR (Nujol): 3450, 1660, 1530 cm$^{-1}$ NMR (DMSO-d$_6$, δ): 2.17(6H, s), 2.4(2H, t, J=7 Hz), 3.2–3.5(2H, m), 7.07–7.47(3H, m), 7.57–8.17 (2H, m), 8.3–8.48(2H, m)

EXAMPLE 130

2-Amino-4-[(1-ethyl-2-pyrrolidinyl)methylcarbamoyl]-5-(2-pyridyl)thiazole (1.7 g) was obtained according to substantially the same manner as that of Example 129 from ethyl 2-amino-5-(2-pyridyl)-4-thiazolecarboxylate (2.49 g) and 2-aminomethyl-1-ethylpyrrolidine (2.89 ml).

mp 171°–172° C. IR (Nujol): 3350, 1640 cm$^{-1}$ NMR (CF$_3$COOH, δ): 1.33–1.7(3H, t), 2.03–2.67(4H, m), 3.07–4.23(7H, m), 7.9–8.2(2H, m), 8.5–9.0 3H, m)

What we claim is:

1. A compound of the formula:

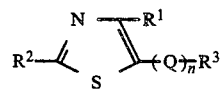

wherein $R^1$ is lower alkyl, carboxy, hydroxymethyl, halomethyl, lower alkylthiomethyl or hydroxyiminomethyl, $R^2$ is hydrogen, hydroxy, lower alkyl, pyridyl, amino, lower alkylamino, pyridylamino or guanidino optionally substituted with dimethylaminomethylene, $R^3$ is dihydroisoquinolyl which may be substituted with halogen, lower alkyl, lower alkoxy, carboxy, hydroxy, pyridyl, amino, lower alkylamino, pyridylamino or guanidino, Q is —CO—, and n is an integer of 0 or 1, and pharmaceutically acceptable salts thereof.

2. A compound of claim 1, wherein
$R^1$ is lower alkyl,
$R^2$ is hydroxy, amino or lower alkylamino,
$R^3$ is dihydroisoquinolyl which may be substituted with lower alkoxy, and
n is an integer of 0.

3. A compound of claim 2, wherein $R^1$ is methyl,
$R^2$ is amino, methylamino or hydroxy and
$R^3$ is dihydroisoquinolyl substituted with methoxy.

4. A compound of claim 3, wherein $R^3$ is [3,4-]dihydroisoquinolyl substituted with two methoxy groups.

5. A compound of claim 4, which is 1-(2-amino-4-methylthiazol-5-yl)-6,7-dimethoxy-3,4-dihydroisoquinoline.

6. A compound of claim 4, which is 1-(2-methylamino-4-methylthiazol-5-yl)-6,7-dimethoxy-3,4-dihydroisoquinoline.

7. A compound of claim 4, which is 1-(2-hydroxy-4-methylthiazol-5-yl)-6,7-dimethoxy-3,4-dihydroisoquinoline.

8. A pharmaceutical composition comprising an effective amount of a compound of claim 1 in association with a pharmaceutically acceptable, substantially non-toxic carrier or excipient.

9. A method for treatment of ulcer which comprises administering an antiulceratively effective amount of a compound of claim 1 to human beings or animals.

* * * * *